(12) United States Patent
Laderoute et al.

(10) Patent No.: US 7,964,341 B2
(45) Date of Patent: Jun. 21, 2011

(54) HUMAN ENDOGENOUS RETROVIRUS K102 WITH FOAMY-VIRUS-LIKE PROPERTIES AND USES THEREOF

(76) Inventors: Marian Laderoute, Quebec (CA); Antonio Giulivi, Ontario (CA); Francisco Diaz-Mitoma, Ontario (CA); Louise Larocque, Ontario (CA)

( * ) Notice: Subject to any disclaimer, the term of this patent is extended or adjusted under 35 U.S.C. 154(b) by 566 days.

(21) Appl. No.: 11/909,001

(22) PCT Filed: Mar. 20, 2006

(86) PCT No.: PCT/CA2006/000397
§ 371 (c)(1),
(2), (4) Date: Sep. 18, 2007

(87) PCT Pub. No.: WO2006/096985
PCT Pub. Date: Sep. 21, 2006

(65) Prior Publication Data
US 2009/0017447 A1    Jan. 15, 2009

Related U.S. Application Data

(60) Provisional application No. 60/663,263, filed on Mar. 21, 2005.

(30) Foreign Application Priority Data

Mar. 18, 2005  (CA) ..................... 2501301

(51) Int. Cl.
*C12Q 1/70* (2006.01)
*G01N 33/53* (2006.01)
(52) U.S. Cl. ....... 435/5; 435/7.1; 424/184.1; 424/185.1; 424/186.1; 424/187.1
(58) Field of Classification Search .................. None
See application file for complete search history.

(56) References Cited

OTHER PUBLICATIONS

Löwer et al. Identifi'cation of human endogenous retroviruses with complex mRNA expression and particle formation. Proceedings of the National Academy of Sciences of the United States of America 1993, vol. 90, pp. 4480-4484.*
Kleiman et al. HERV-K(HML-2) GAG/ENV Antibodies as Indicator for Therapy Effect in Patients With Germ Cell Tumors. Internal Journal of Cancer 2004, vol. 110, pp. 459-461.*
Tonjes RR et al Genome-wide screening, cloning, chromosomal assignment, and expression of full length human endogenous retrovirus type K: Journal of Virology, Nov. 1999 vol. 73, No. 11 pp. 9187-9195.
Kuhelj R. et al "Inhibition of human endogenous retrovirus K10 protease in cell free and cell based assays" The Journal of Biological Chemistry May 2001, vol. 276 No. 20 pp. 16674-16682.
Etkind PR et al "type 1 HERV-K genome is spliced into subgenomic transcripts in the human breast tumor cell line T47D" Virology Aug. 1997 vol. 234 No. 2 pp. 304-308.
Patience C et al "Human endogenous retroviral expression and reverse transcriptase activity in the T47D mammary carcinoma cell line" Journal of Virology Apr. 1996 vol. 70 No. 4 pp. 2654-2657.
Conejero-Goldberg C et al—"infectious pathogen detection arrays: viral detection in cell lines and postmortem brain tissue" Biotechniques Nov. 2005, vol. 39 No. 5 pp. 741-749.
Frank O et al—Human Endogenous retrovirus expression profiles in samples from brains of patients with schizophrinia and bipolar disorders Journal of Virology Sep. 2005 vol. 79 No. 17 pp. 10890-10901.
Ejthadi HD et al A novel multiplex RT-PCR system detects human endogenous retrovirus K in breast cancer Archives of Virology Jan. 2005 vol. 150 No. 1 pp. 177-184.
Morgan D et al "Human endogenous retrovirus (HERV-K) particles in megakaryocytes cultured from essential thrombocythemia peripheral blood stem cells" Experimental Hemtology Jun. 2004 vol. 32 No. 6 pp. 520-525.
Wang-Johanning F et al "Expression of human endogenous retrovirus K Envelope transcripts in human breast cancer" Clinical Cancer Research Jun. 2001 vol. 7 No. 6 pp. 1553-1560.
Barbulescu M et al "Many human retrovirus K (HERV-K) proviruses are unique to humans" Current Biology Aug. 1999 vol. 9 pp. 861-868.
Ono M. et al Nucleotide sequence of human endogenous retrovirus genome related to teh mouse mammary tumor virus genome Journal of Virology Nov. 1986 vol. 60 No. 2 pp. 589-598.

* cited by examiner

*Primary Examiner* — Zachariah Lucas
*Assistant Examiner* — Louise Humphrey
(74) *Attorney, Agent, or Firm* — Michael R. Williams

(57) ABSTRACT

The invention relates to the discovery of a human endogenous retrovirus (HERV) family, Type I HERV-K (HML-2) which appear to be active in vitro and in vivo, infectious, and which have the have the salient features and properties of foamy retroviruses. Based on its natural replication in humans, and that it protects the host from viral and tumor transformation, this non-pathogenic endogenous virus could be developed as a replication competent gene therapy vector. It also is expected to have much higher efficacy than other vectors as it crosses the bloodbrain barrier and infects almost all cell types in the host (proliferating or not). It may naturally lyse tumor cells or infected cells, and thus could even be used without genetic modification. Of course, this vector could be used in traditional ways with it ability to replicate genetically removed. In addition to its value as a vector, as it is reactivated with infection, its detection could also be used to monitor the safety of gene therapy (irrespective of vector type used), as well as other biological therapies including vaccination, blood transfusion, transplantation and xenotransplantation. Finally it may be used to screen for new therapeutic and prophylactic treatments for a wide variety of diseases.

3 Claims, 20 Drawing Sheets

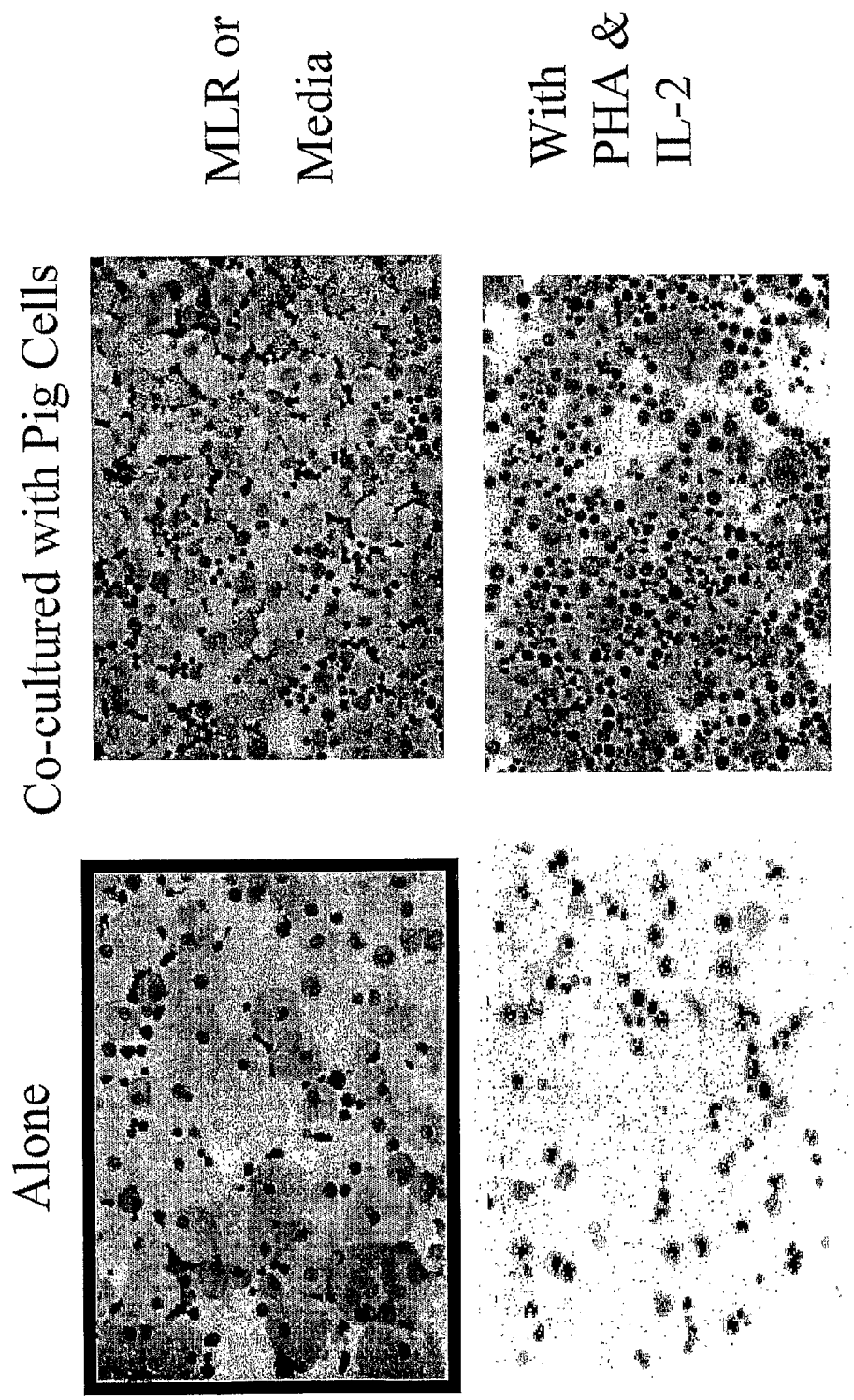
Fig. 1 Vacuolation in Cord Blood is Inducible and Blocked by IL-2/PHA Treatment

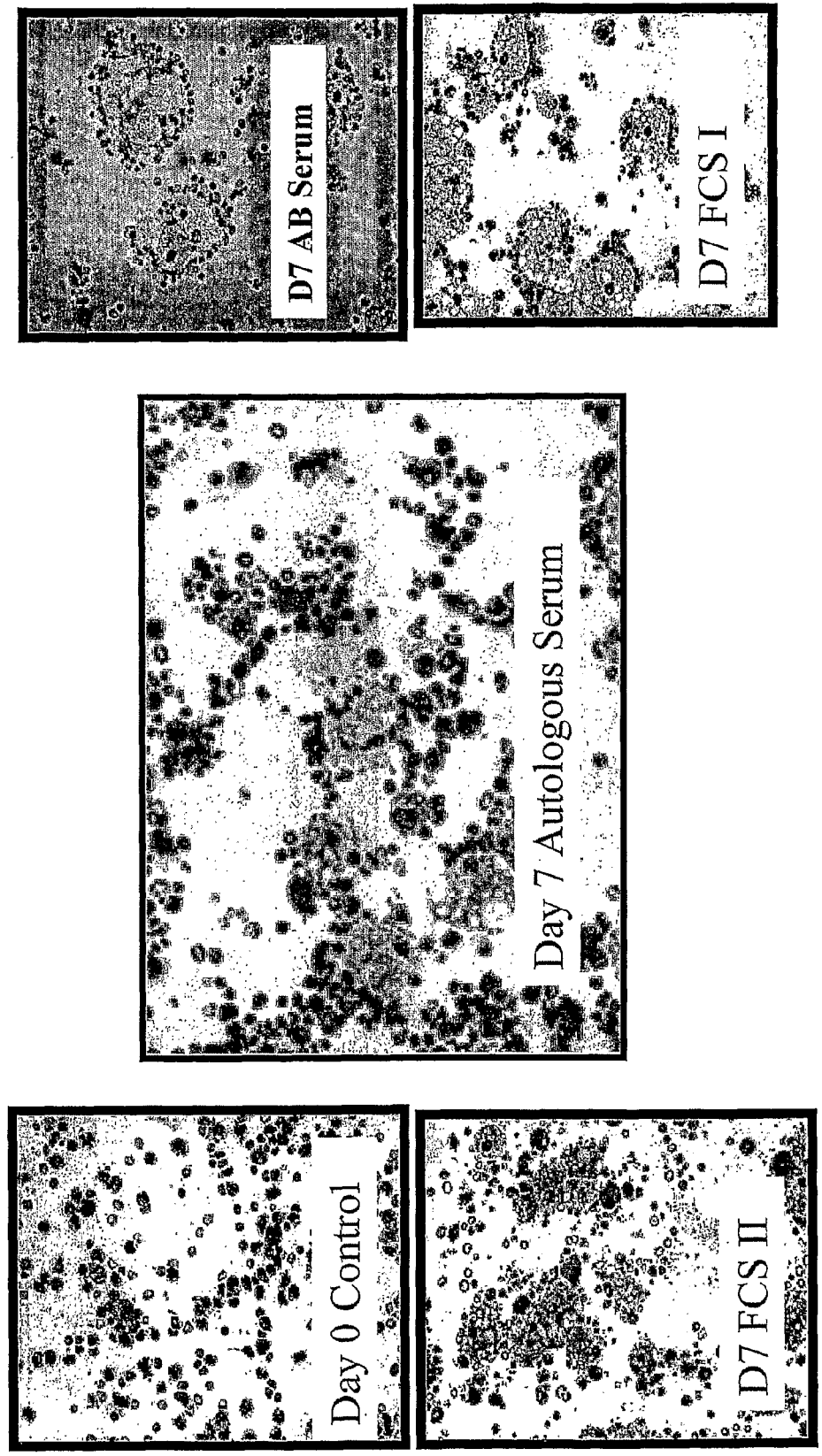
Fig. 2 Induction of Vacuolation (Day 7) was Independent of Source of Serum

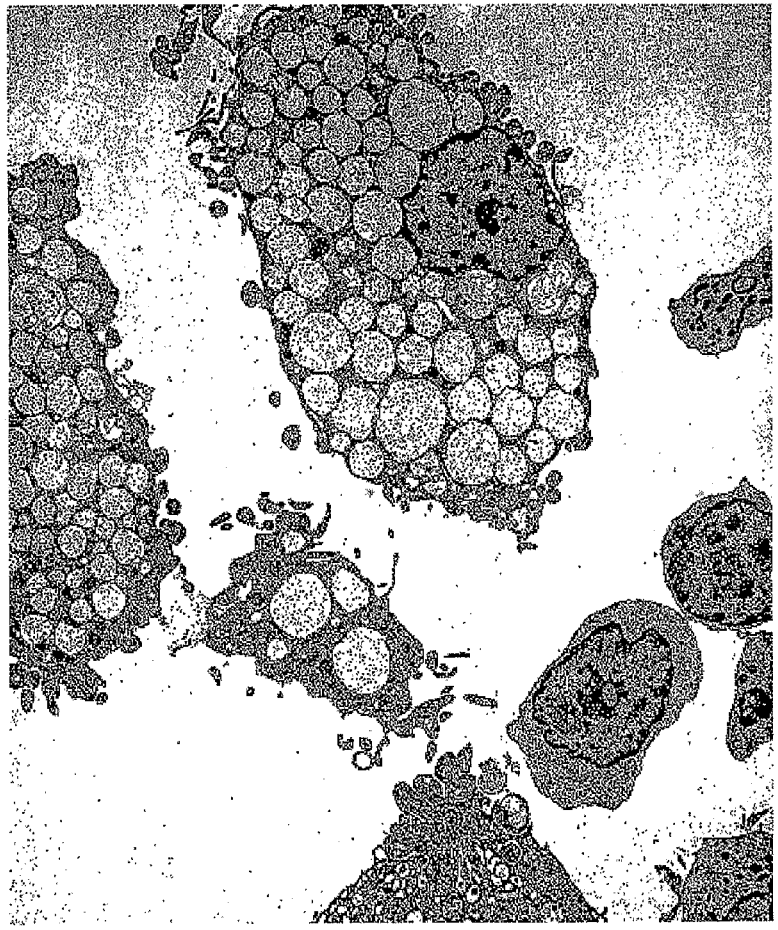
Fig. 3  Electron Microscopy

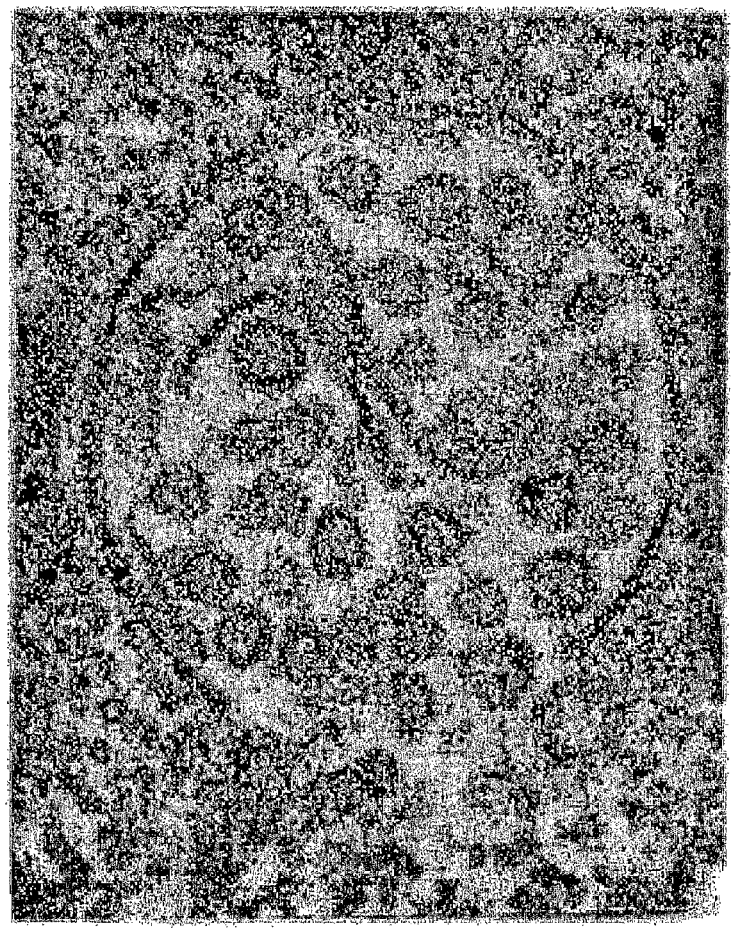
Fig. 4 Immature Particles found within the Vacuoles

Fig. 5 Primers for Regular PCR for HERV-K102 *pol*

Forward (nt 4272-4291)

5' – TGG CAG AGC AGG ATT GTG AA- 3'

Reverse (nt 4565-4546)

5' – CAG ATG CTA TTG CCA GTC CA – 3'

Primes a 295 bp product from 4272 to 4565.

Fig. 6 PCR for HERV-K Type I pol
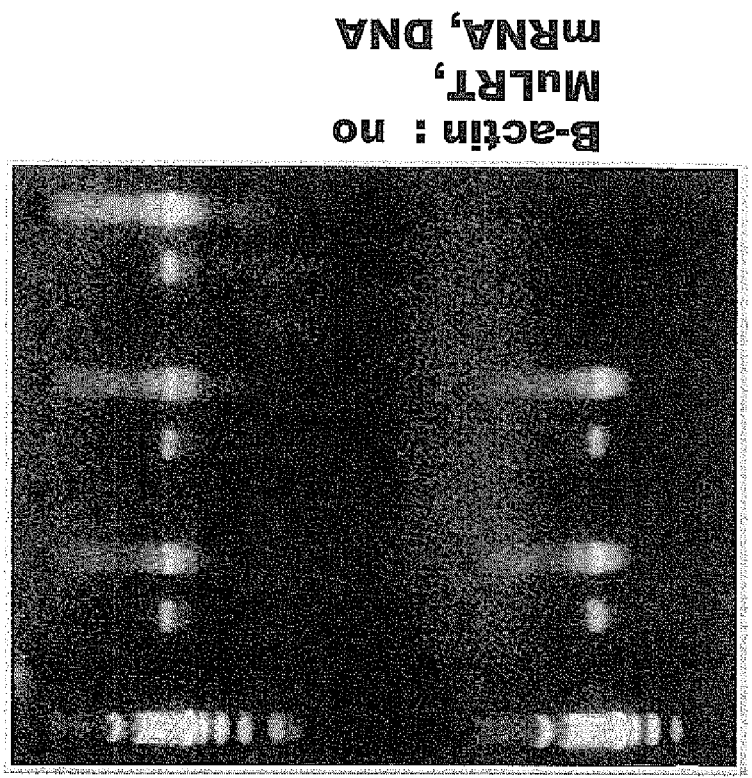
B-actin : no
MuLRT,
mRNA, DNA
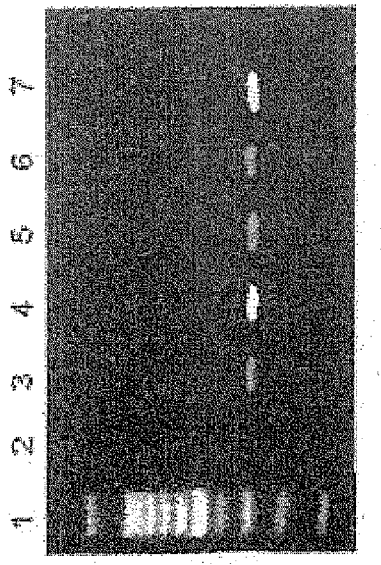
HERV-K *pol* mRNA
| Day | 0 | 3 | 5 | 7 | 11 | DNAd0 |
11 12 13 14 15 16 17

Fig. 7 Sequencing of RT-PCR Product

- ctggcagagc aggattgcga aaaatttgcc tttactatac cagccataaa
- taataaagaa ccagccacca ggtttcagtg gaaagtgtta cctcagggaa tgcttaatag
- tccaactatt tgtcagactt ttgtaggttg agctcttcaa ccagttagag aaaagttttc
- agactgttat attattcatt atattgatga tattttatgt gctgcagaaa cgagagataa
- attaattgac tgttatacat ttctgcaagc agaggttgcc aatgctggac tggcaatagc
- atctg SEQ ID No. 7

Fig. 8 HERV-K102 Peptide Sequence of Envelope

ML-4 (nt 6473-6520)   Type I HERV-K (HML-2) Specific
KRASTEMVTPVTWMDN
ML-5 (nt 7229-7279)   HERV-K102 Specific
LETRDCKPFYTIDLNSS

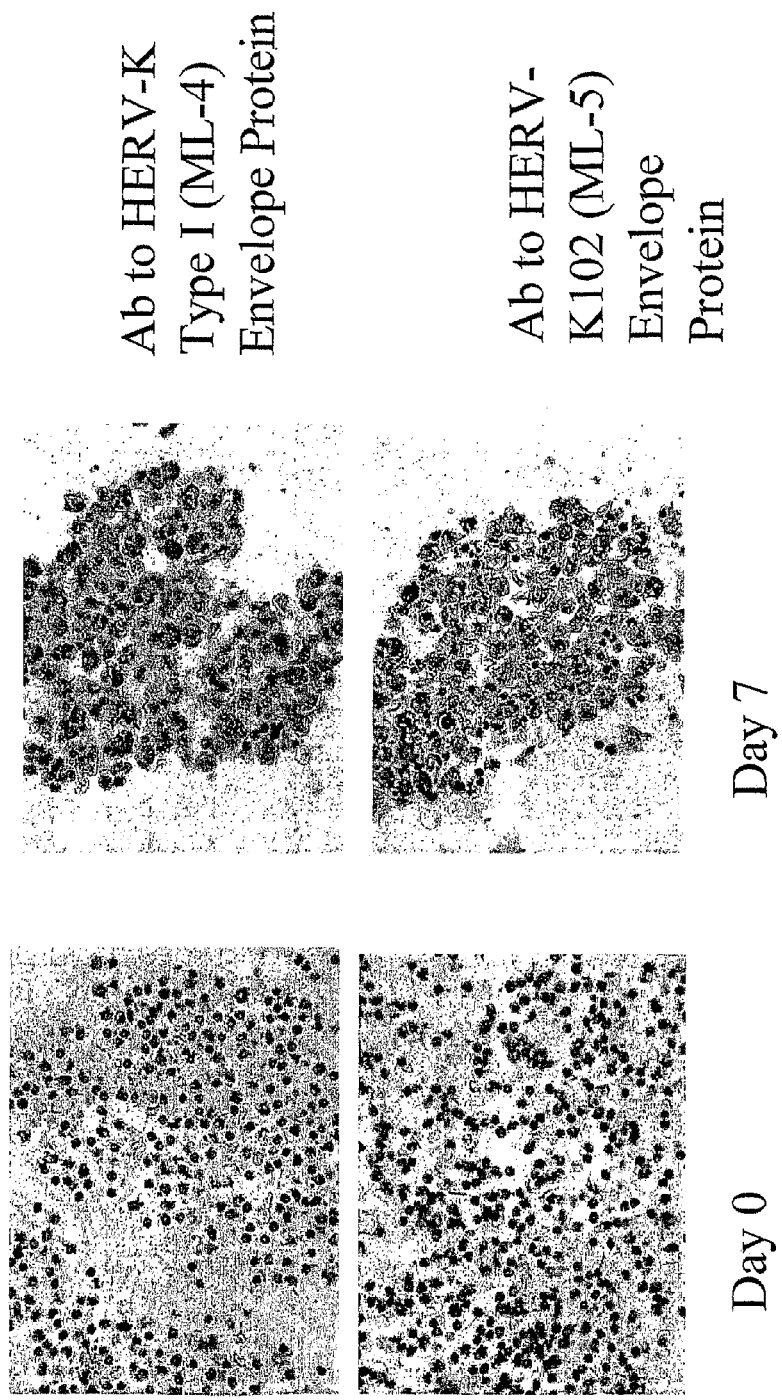
Fig. 9 Immunohistology

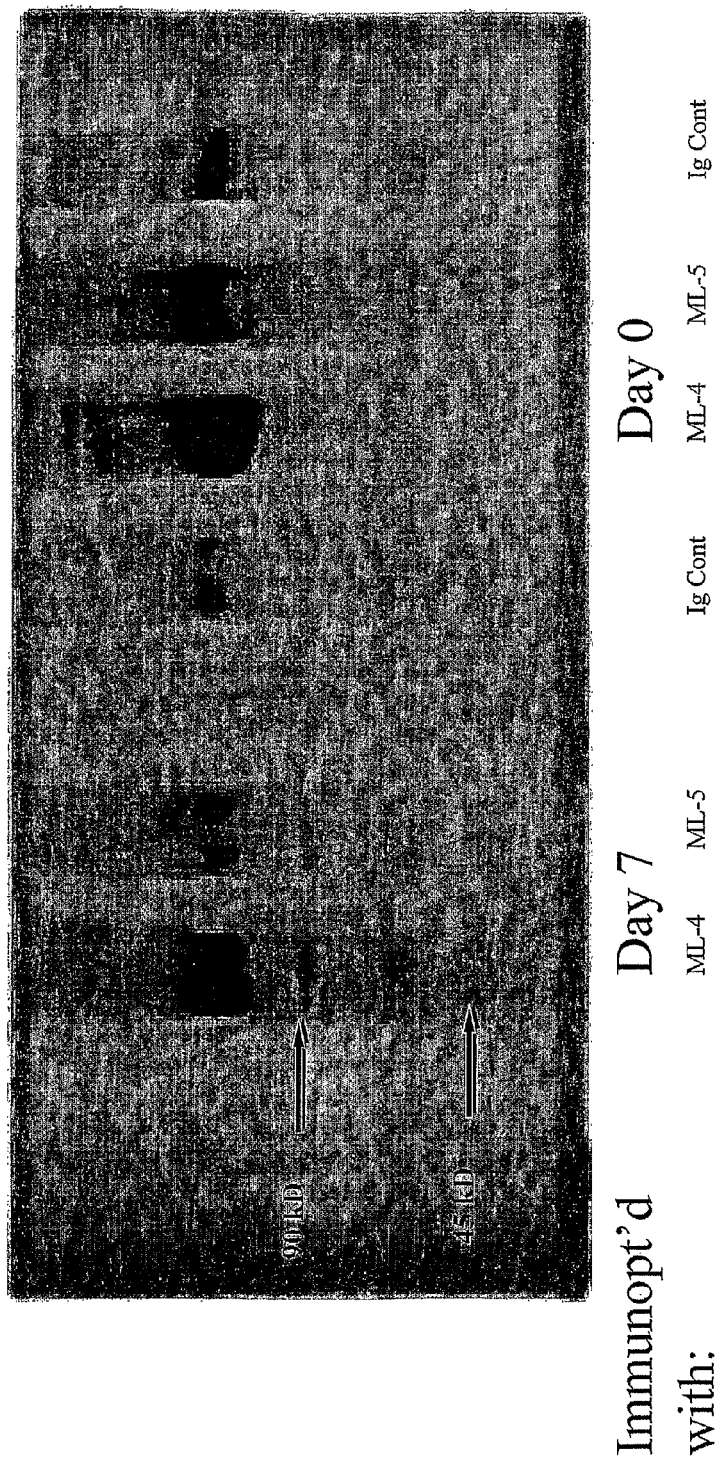
Fig. 10 Western Blot with ML-4

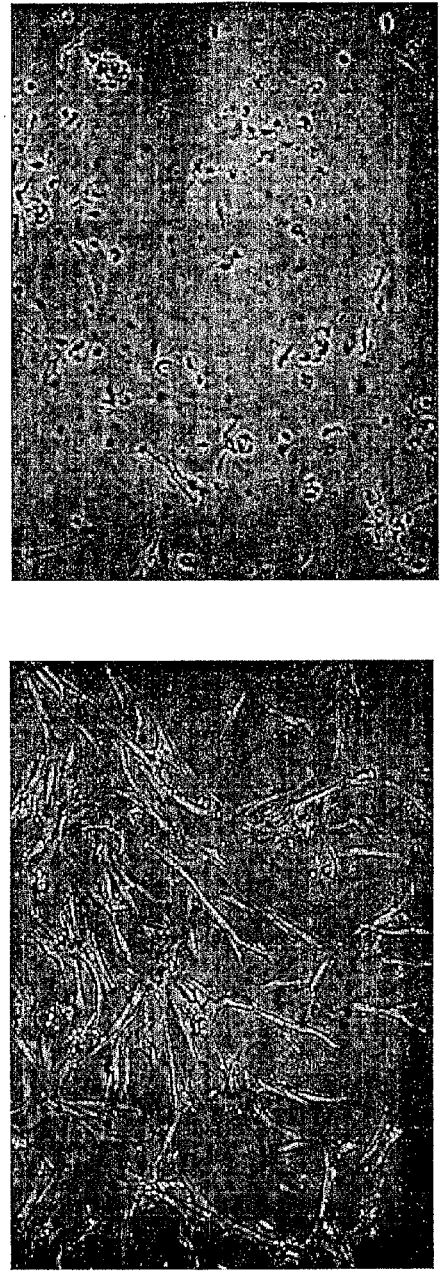
Fig. 11 Lytic Infection only seen with MRC-5 not HFL-1 or Vero Cells
Day 4
Day 0 or Media Control

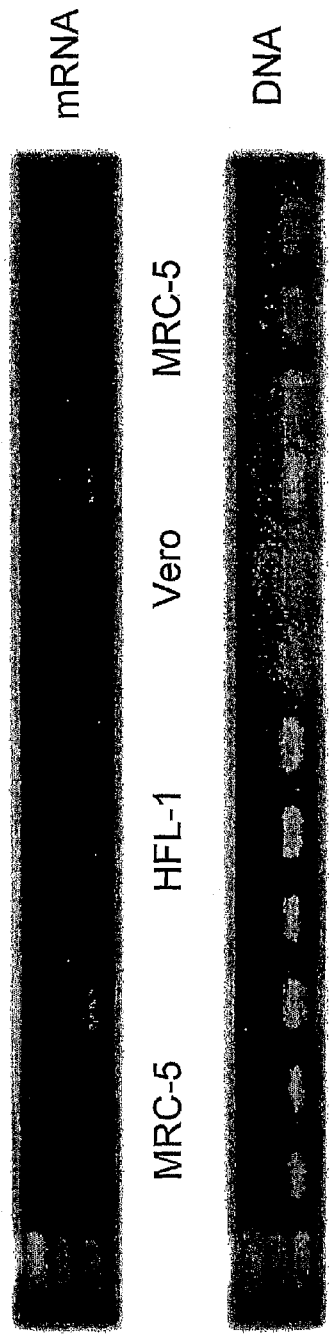
Fig. 12 RT-PCR Confirms INFECTION in both MRC-5 cells and in Vero (Green Monkey) Cells (but infectivity not transferred by supernatants)

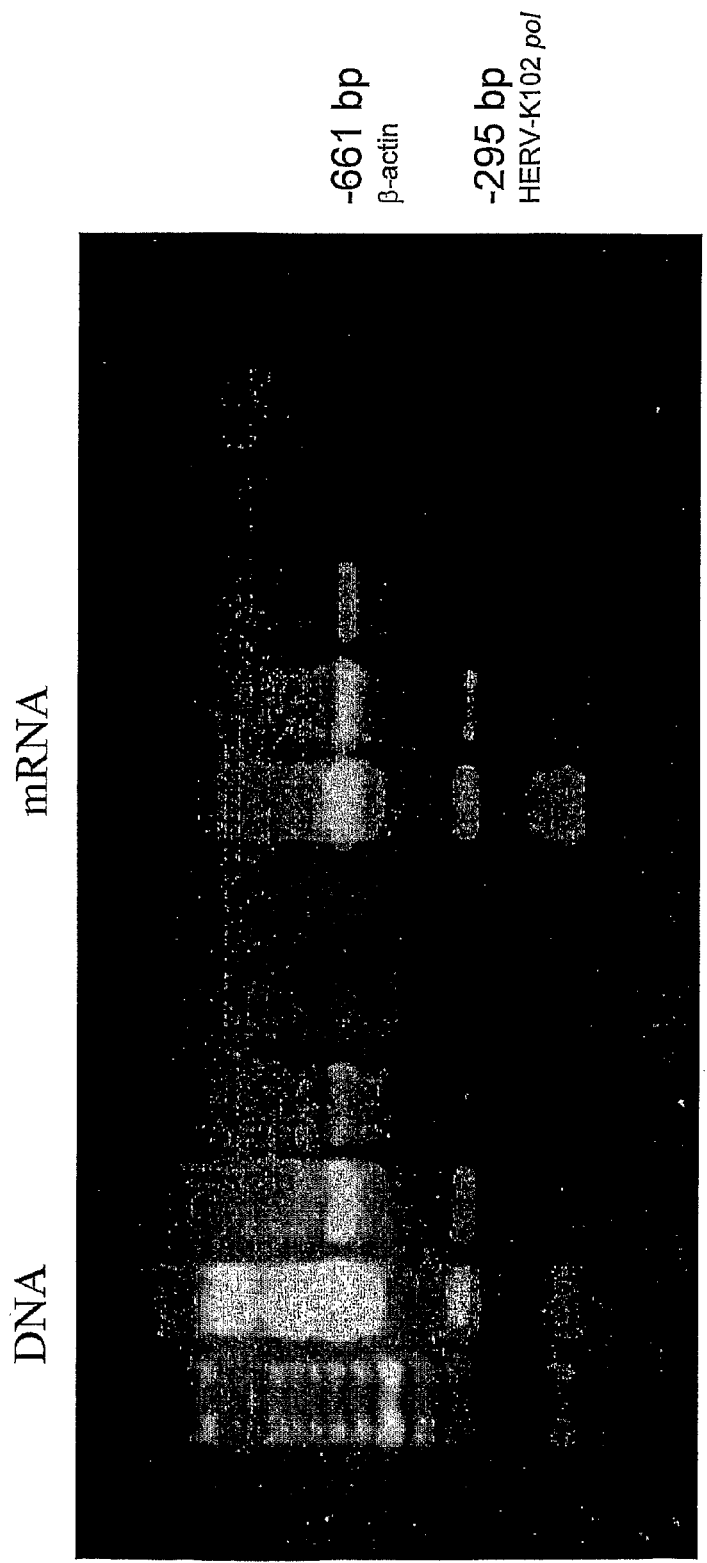
Fig. 13 Titration of the Relative Sensitivities of the β-Actin PCR vs. HERV-K102 pol PCR Methods

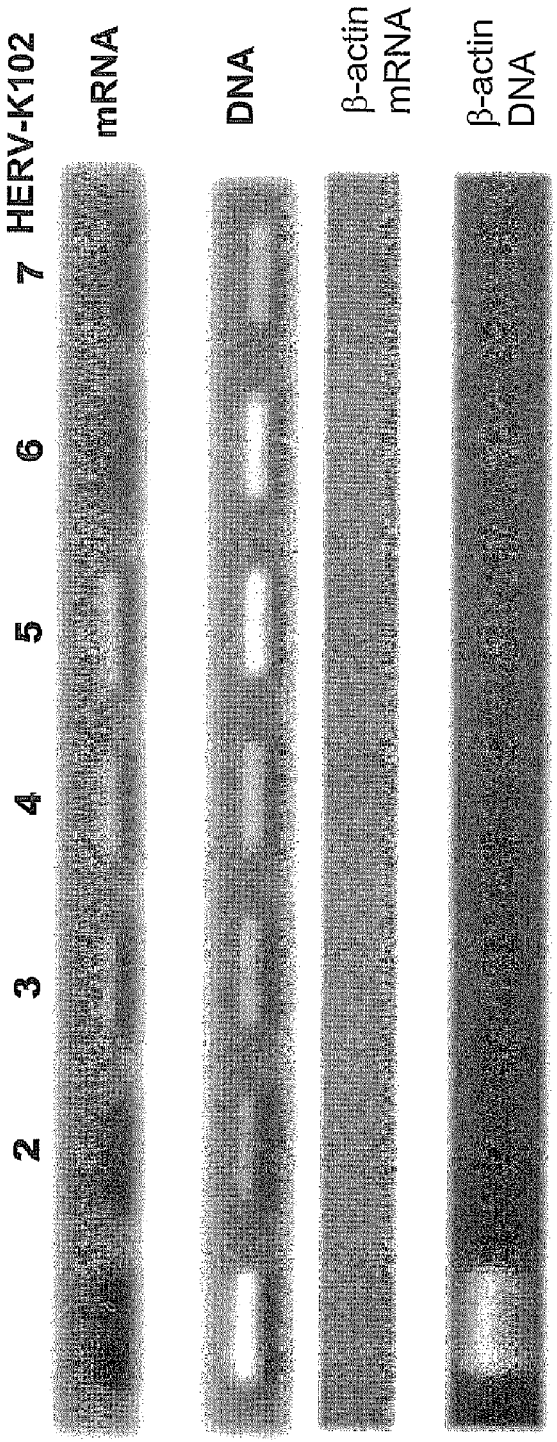
Fig. 14 *In Vivo* Evidence for Activity: Putative Particles in Human Plasma

Fig. 15 HERV-K102 Sequence, Primers and Probe are Distinct from HIV

Forward Primer [10/19 id*]                                                          Probe K102 4414  TCTTCAACCAGTTAGAGAGAAAAGTTTTCAGACTGTTATATTATTCATTATATTGATGATAT 4473
K101 4415  TCTTCAACCAGTTAGAGAGAAAAGTTTTCAGACTGTTATATTATTCATTATATTGATGATAT 4474
HIV-1 502  TTAGAGCCTTTTAGAAGA AAATATCCAGACATAGTTATCTGTCAATACGTAGATGAT TTG 561

Probe [4/21 id*]                                                  Reverse

4474  TTTATGTGCTGCAGAAACGAGAGATAAATTAATTGACTGTTATACATTTCTGCAAGCAGA 4533
4475  TTTATGTGCTGCAGAAACGAGAGATAAATTAATTGACTGTTATACATTTCTGCAAGCAGA 4534
HIV-1 TATGTAGCATCTGACTTAGAACATAGAGCAGCATAGAACAAAATAGAGGAACTGAGA 618

Primer [7/18 id*]
4534  GGTTGCCA 4541
4535  GGTTGCCA 4542
619   CAATATCT 626      *HIV to HERV-K102

HERV-K102   GenBank Entry AF164610
HERV-K101   GenBank Entry AF164609
HIV-1 (US isolate) GenBank Entry AY801210

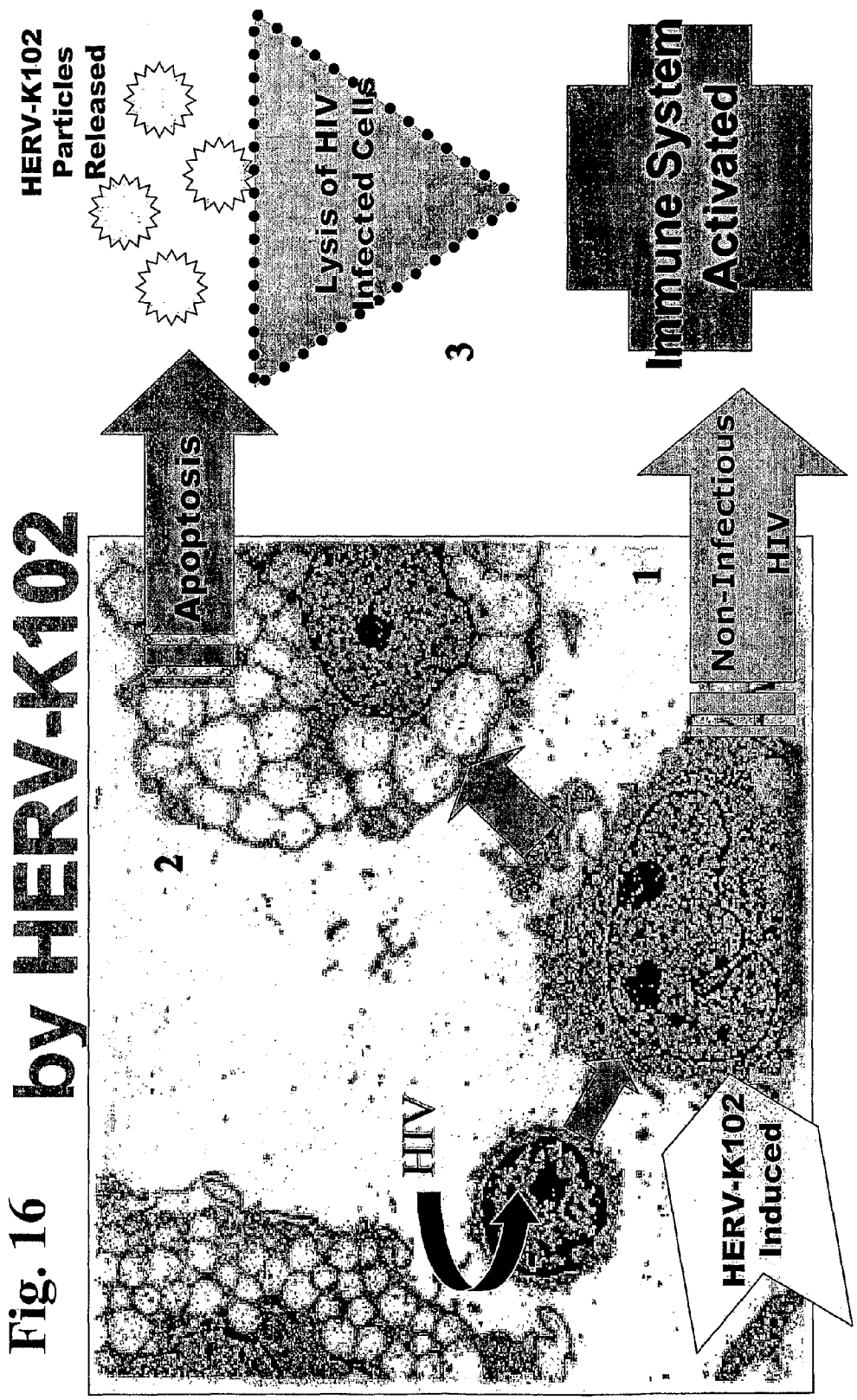
Fig. 16 Model for HIV Antagonism by HERV-K102

```
   1 tgtggggaaa agcaagagag atcagattgt tactgtgtct gtgtagaaag aagtagacat
  61 gggagactcc attttgttat gtgctaagaa aaattcttct gccttgagat tctgttaatc
 121 tatgacctta cccccaaccc cgtgctctct gaaacgtgtg ctgtgtcaac tcagggttga
 181 atggattaag ggcggtgcag gatgtgcttt gttaaacaga tgcttgaagg cagcatgctc
 241 cttaagagtc atcaccactc cctaatctca agtacccagg gacacaaaaa ctgcggaagg
 301 ccgcagggac ctctgcctag gaaagccagg tattgtccaa ggtttctccc catgtgatag
 361 tctgaaatat ggcctcgtgg gaagggaaag acctgaccgt cccccagccc gacacccgta
 421 aagggtctgt gctgaggagg attagtataa gaggaaggaa tgcctcttgc agttgagaca
 481 agaggaaggc atctgtctcc tgcctgtccc tgggcaatgg aatgtctcgg tataaaaccc
 541 gattgtatgc tccatctact gagataggga aaaaccgcct tagggctgga ggtgggacct
 601 gcgggcagca atactgcttt gtaaagcact gagatgttta tgtgtatgca tatccaaaag
 661 cacagcactt aatcctttac attgtctatg atgccaagac ctttgttcac gtgtttgtct
 721 gctgaccctc tccccacaat tgtcttgtga ccctgacaca tcccctctt tgagaaacac
 781 ccacagatga tcaataaata ctaagggaac tcagaggctg gcgggatcct ccacatgctg
 841 aacgctggtt ccccgggtcc ccttatttct ttctctatac tttgtctctg tgtcttttc
 901 ttttccaaat ctctcatccc accttacgag aaacacccac aggtgtgtag gggcaaccca
 961 ccctacatc tggtgcccaa cgtggaggct tttctctagg gtgaaggtac gctcgagcgt
1021 ggtcattgag gacaagtcga cgagagatcc cgagtacatc tacagtcagc cttacggtaa
1081 gcttgtgcgc tcggaagaag ctagggtgat aatggggcaa actaaaagta aaattaaaag
1141 taaatatgcc tcttatctca gctttattaa aattcttta aaaagagggg gagttaaagt
1201 atctacaaaa aatctaatca agctatttca aataatagaa caattttgcc catggtttcc
1261 agaacaagga actttagatc taaaagattg gaaaagaatt ggtaaggaac taaaacaagc
1321 aggtaggaag ggtaatatca ttccacttac agtatggaat gattgggcca ttattaaagc
1381 agctttagaa ccatttcaaa cagaagaaga tagcgtttca gtttctgatg cccttggaag
1441 ctgtataata gattgtaatg aaaacacaag gaaaaaatcc cagaaagaaa cggaaggttt
1501 acattgcgaa tatgtagcag agccggtaat ggctcagtca acgcaaaatg ttgactataa
1561 tcaattacag gaggtgtatat atcctgaaac gttaaaatta gaaggaaaag gtccagaatt
1621 agtggggcca tcagagtcta aaccacgagg cacaagtcat cttccagcag gtcaggtgcc
1681 cgtaacatta caacctcaaa agcaggttaa agaaaataag acccaaccgc cagtagccta
1741 tcaatactgg cctccggctg aacttcagta tcggccaccc ccagaaagtc agtatggata
1801 tccaggaatg ccccccagcac cacagggcag ggcgccatac cctcagccgc ccactaggag
1861 acttaatcct acggcaccac ctagtagaca gggtagtgaa ttcatgaaa ttattgataa
1921 atcaagaaag gaaggagata ctgaggcatg gcaattccca gtaacgttag aaccgatgcc
1981 acctggagaa ggagcccaag agggagagcc tcccacagtt gaggccagat acaagtcttt
2041 ttcgataaaa atgctaaaag atatgaaaga gggagtaaaa cagtatggac ccaactcccc
2101 ttatatgagg acattattag attccattgc tcatggacat agactcattc cttatgattg
2161 ggagattctg gcaaaatcgt ctctctcacc ctctcaattt ttacaattta agacttggtg
2221 gattgatggg gtacaagaac aggtccgaag aaatagggct gccaatcctc cagttaacat
2281 agatgcagat caactattag gaataggtca aaattggagt actattagtc aacaagcatt
2341 aatgcaaaat gaggccattg agcaagttag agctatctgc cttagagcct gggaaaaaat
2401 ccaagaccca ggaagtacct gccccctcatt taatacagta agacaaggtt caaaagagcc
2461 ctatcctgat tttgtggcaa ggctccaaga tgttgctcaa aagtcaattg ccgatgaaaa
2521 agcccgtaag gtcatagtgg agttgatggc atatgaaaac gccaatcctg atgtcaatca
2581 gccattaagc cattaaaagg aaaggttcct gcaggatcag atgtaatctc agaatatgta
2641 aaagcctgtg atggaatcgg aggagctatg cataaagcta tgcttatggc tcaagcaata
2701 acaggagttg ttttaggagg acaagttaga acatttggag gaaatgtta taattgtggt
2761 caaattggtc acttaaaaaa gaattgtcca gtcttaaata acagaatat aactattcaa
2821 gcaactacaa caggtagaga gccacctgac ttatgtccaa gatgtaaaaa aggaaaacat
2881 tgggctagtc aatgtcgttc taaatttgat aaaaatgggc aaccattgtc gggaaacgag
2941 caaaggggcc agcctcaggc cccacaacaa actggggcat tcccaattca gccatttgtt
3001 cctcagggtt tcaggaaca acaaccccca ctgtcccaag tgtttcaggg aataagccag
3061 ttaccacaat acaacaattg tccccgcca aagcggcag tgcagcagta gatttatgta
3121 ctatacaagc agtctctctg cttccagggg agcccccaca aaaaatccct acagggtat
3181 atggcccact gcctgagggg actgtaggac taatcttggg aagatcaagt ctaaatctaa
```

Figure 17-1

```
3241 aaggagttca aattcatact agtgtggttg attcagacta taaaggcgaa attcagttgg
3301 ttattagctc ttcaattcct tggagtgcca gtccaggaga caggattgct caattattac
3361 tcctgccata tattaagggt ggaaatagtg aaataaaaag aataggaggg cttggaagca
3421 ctgatccaac aggaaaggct gcatattggg caagtcaggt cacagagaac agacctgtgt
3481 gtaaggccat tattcaagga aaacagtttg aagggttggt agacactgga gcagatgtct
3541 ctatcattgc tttaaatcag tggccaaaaa attggcctaa acaaaaggct gttacaggac
3601 ttgtcggcat aggcacagcc tcagaagtgt atcaaagtac tgagatttta cattgcttag
3661 ggccagataa tcaagaaagc actgttcagc caatgattac ttcaattcct cttaatctgt
3721 ggggtcgaga tttattacaa caatggggtg cggaaatcac catgcctgcc ccattatata
3781 gccccacgag tcaaaaaatc atgaccaaga tgggatatat accaggaaag ggactaggga
3841 aaaatgaaga tggcattaaa gttccagttg aggctaaaat aaatcaagaa agagaaggaa
3901 tagggtatcc ttttttagggg cggccactgt agagcctcct aagcccatac cactaacttg
3961 gaaaacagaa aaaccggtgt gggtaaatca gtggccgcta ccaaaacaaa aactggaggc
4021 tttacattta ttagcaaatg aacagttaga aaagggtcac attgagcctt cgttctcacc
4081 ttggaattct cctgtgtttg taattcagaa gaaatcaggc aaatggcgta tgttaactga
4141 cttaagggct gtaaacgccg taattcaacc catgggggcct ctccaacctg ggttgccctc
4201 tccagccatg atcccaaaag attggccttt aattataatt gatctaaagg attgcttttt
4261 taccatccct ctggcagagc aggattgcga aaaatttgcc tttactatac cagccataaa
4321 taataaagaa ccagccacca ggtttcagtg gaaagtgtta cctcaggaa tgcttaatag
4381 tccaactatt tgtcagactt ttgtaggttg agctcttcaa ccagttagag aaaagttttc
4441 agactgttat attattcatt atattgatga tatttttatgt gctgcagaaa cgagagataa
4501 attaattgac tgttatacat ttctgcaagc agaggttgcc aatgctggac tggcaatagc
4561 atctgataag atccaaacct ctactccttt tcattattta gggatgcaga tagaaaatag
4621 aaaaattaag ccacaaaaag tagaaataag aaaagacaca ttaaaaacac taatgatttt
4681 tcaaaaatta ctaggagata ttaattggat tcggccaact ctaggcattc ctacttatgc
4741 catgtcaaat ttgttctcta tcttaagagg agactcagac ttaaatagta aagaatatt
4801 aaccccgagg gcaacaaaag aaattaaatt agtggaagaa aaaattcagt cagcgcaaat
4861 aaatagaata gatcccttag ccccactcca acttttgatt tttgccactg cacattctcc
4921 aacaggtatc attattcaaa atactgatct tgtggagtgg tcattccttc ctcacagtac
4981 agttagact tttacactgt acttggatca aatagctaca ttaattggtc agacaagatt
5041 acgaataata aaattatatg gaaatgaccc agacaaaata gttgtcccctt taaccaagga
5101 acaagttaga caagccttta tcaattctgg tgcatggcag attggtcttg ctaattttgt
5161 gggaattatt gataatcatt acccaaaaac aaagatcttc cagttcttaa aactgactac
5221 ttggattcta cctaaaatta ccagacgtga acctttagaa aatgctctaa cagtatttac
5281 tgatggttcc agcaatggaa aagcagctta cacaggaccg aaagaacgag taatcaaaac
5341 tccatatcaa tcggctcaaa gagcagagtt ggttgcagtc attacagtgt tacaagattt
5401 tgaccaacct atcaatatta tatcagattc tgcatatgta gtacaggcta caagggatgt
5461 tgagacagct ctaattaaat atagcatgga tgatcagtta accagctat tcaatttatt
5521 acaacaaact gtaagaaaaa gaaatttccc attttatatt actcatattc gagcacacac
5581 taatttacca gggcctttga ctaaagcaaa tgaacaagct gacttactgg tatcatctgc
5641 actcataaaa gcacaagaac ttcatgcttt gactcatgta aatgcagcag gattaaaaaa
5701 caaatttgat gtcacatgga acaggcaaa agatattgta caacattgca cccagtgtca
5761 aatcttacac ctgcccactc aagaggcagg agttaatccc agaggtctgt gtcctaatgc
5821 attatggcaa atggatgtca cgcatgtacc ttcatttgga agattatcat atgttcacgt
5881 aacagttgat acttattcac atttcatatg ggcaacttgc caaacaggag aaagtacttc
5941 ccatgttaaa aaacatttat tgtcttgttt tgctgtaatg ggagttccag aaaaaatcaa
6001 aactgacaat ggaccaggat attgtagtaa agcttttcaa aaattcttaa gtcagtggaa
6061 aatttcacgt acaacaggaa ttccttataa ttcccaagga caggcctag ttgaaagaac
6121 taatagaaca ctcaaaactc aattagttaa acaaaaagaa ggggagaca gtaaggagtg
6181 taccactcct cagatgcaac ttaatctagc actctatact ttaaattttt taaacattta
6241 tagaaatcag actactactt ctgcagaaca acatcttact ggtaaaaaga acagcccaca
6301 tgaaggaaaa ctaatttggt ggaaagataa taaaaataag acatgggaaa tagggaaggt
6361 gataacgtgg gggagaggtt ttgcttgtgt tcaccagga gaaaatcagc ttcctgtttg
```

Figure 17-2

```
6421 gatacccact agacatttga agttctacaa tgaacccatt ggagatgcaa agaaaagggc
6481 ctccacggag atggtaacac cagtcacatg gatggataat cctatagaaa tatatgttaa
6541 tgatagtgta tgggtacctg gacccataga tgatcgctgc cctgccaaac ctgaggaaga
6601 agggatgatg ataaatattt ccattgggta tcgttatcct cctatttgcc tagggagagc
6661 accaggatgt ttaatgcctg cagtccaaaa ttggttggta gaagtaccta ctgtcagtcc
6721 catcagtaga ttcacttatc acatggtaag cgggatgtca ctcaggccac gggtaaatta
6781 tttacaagac ttttcttatc aaagatcatt aaaatttaga cctaaaggga aaccttgccc
6841 caaggaaatt cccaaagaat caaaaaatac agaagtttta gtttgggaag aatgtgtggc
6901 caatagtgcg gtgatattac aaaacaatga atttggaact attatagatt gggcacctcg
6961 aggtcaattc taccacaatt gctcaggaca aactcagtcg tgtccaagtg cacaagtgag
7021 tccagctgtt gatagcgact taacagaaag tttagacaaa cataagcata aaaaattgca
7081 gtctttctac ccttgggaat ggggagaaaa aagaatctct accccaagac caaaaatagt
7141 aagtcctgtt tctggtcctg aacatccaga attatggagg cttactgtgg cctcacacca
7201 cattagaatt tggtctggaa atcaaacttt agaaacaaga gattgtaagc cattttatac
7261 tatcgaccta aattccagtc taacagttcc tttacaaagt tgcgtaaagc ccccttatat
7321 gctagttgta ggaaatatag ttattaaacc agactcccag actataacct gtgaaaattg
7381 tagattgctt agttgcattg attcaacttt taattggcaa caccgtattc tgctggtgag
7441 agcaagagag ggcgtgtgga tccctgtgtc catggaccga ccatgggagg cctcaccatc
7501 cgtccatatt ttgactgaag tattaaaagg tgttttaaat agatccaaaa gattcatttt
7561 tactttaatt gcagtgatta tgggattaat tgcagtcaca gctacggctg ctgtagcagg
7621 agttgcattg cactcttctg ttcagtcagt aaactttgtt aatgattggc aaaagaattc
7681 tacaagattg tggaattcac aatctagtat tgatcaaaaa ttggcaaatc aaattaatga
7741 tcttagacaa actgtcattt ggatgggaga cagactcatg agcttagaac atcgtttcca
7801 gttacaatgt gactggaata cgtcagattt ttgtattaca ccccaaattt ataatgagtc
7861 tgagcatcac tgggacatgg ttagacgcca tctacaggga agagaagata atctcacttt
7921 agacatttcc aaattaaaag aacaaatttt cgaagcatca aaagcccatt taaatttggt
7981 gccaggaact gaggcaattg caggagttgc tgatggcctc gcaaatctta accctgtcac
8041 ttgggttaag accattggaa gtactacgat tataaatctc atattaatcc ttgtgtgcct
8101 gttttgtctg ttgttagtct gcaggtgtac ccaacagctc cgaagagaca gcgaccatcg
8161 agaacgggcc atgatgacga tggcggtttt gtcgaaaaga aaggggggaa atgtgggaa
8221 aagcaagaga gatcagattg ttactgtgtc tgtgtagaaa gaagtagaca tgggagactc
8281 cattttgtta tgtgttaaga aaaattcttc tgccttgaga ttctgttaat ctatgacctt
8341 acccccaacc ccgtgctctc tgaaacgtgt gctgtgtcaa ctcagggttg aatggattaa
8401 gggcggtgca ggatgtgctt tgttaaacag atgcttgaag gcagcatgct ccttaagagt
8461 catcaccact ccctaatctc aagtacccag gacacaaaaa ctgcggaagg ccgcagggac
8521 ctctgcctag gaaagccagg tattgtccaa ggtttctccc catgtgatag tctgaaatat
8581 ggcctcgtgg gaagggaaag aacctgaccgt cccccagcct gacacccgta aagggtctgt
8641 gctgaggagg attagtataa gaggaaggaa tgcctcttgc agttgagaca agaggaaggc
8701 atctgtctcc tgcctgtccc tgggcaatgg aatgtctcgg tataaaaccc gattgtatgc
8761 tccatctact gagatagggga aaaccgcct tagggctgga ggtgggacct gcgggcagca
8821 atactgcttt gtaaagcact gagatgttta tgtgtatgca tatccaaaag cacagcactt
8881 aatcctttac attgtctatg atgccaagac ctttgttcac gtgtttgtct gctgaccctc
8941 tccccacaat tgtcttgtga ccctgacaca tcccctctt tgagaaacac ccacagatga
9001 tcaataaaata ctaagggaac tcagaggctg gcgggatcct ccatatgctg aacgctggtt
9061 ccccgggtcc ccttatttct ttctctatac tttgtctctg tgtctttttc ttttccaaat
9121 ctctcgtccc accttacgag aaacacccac aggtgtgtag gggcaaccca ccctaca
```

Figure 17-3

```
MGQTKSKIKSKYASYLSFIKILLKRGGVKVSTKNLIKLFQIIEQ

FCPWFPEQGTLDLKDWKRIGKELKQAGRKGNIIPLTVWNDWAIIKAALEPFQTEEDSV

SVSDALGSCIIDCNENTRKKSQKETEGLHCEYVAEPVMAQSTQNVDYNQLQEVIYPET

LKLEGKGPELVGPSESKPRGTSHLPAGQVPVTLQPQKQVKENKTQPPVAYQYWPPAEL

QYRPPPESQYGYPGMPPAPQGRAPYPQPPTRRLNPTAPPSRQGSELHEIIDKSRKEGD

TEAWQFPVTLEPMPPGEGAQEGEPPTVEARYKSFSIKMLKDMKEGVKQYGPNSPYMRT

LLDSIAHGHRLIPYDWEILAKSSLSPSQFLQFKTWWIDGVQEQVRRNRAANPPVNIDA

DQLLGIGQNWSTISQQALMQNEAIEQVRAICLRAWEKIQDPGSTCPSFNTVRQGSKEP

YPDFVARLQDVAQKSIADEKARKVIVELMAYENANPDVNQPLSH
```

Figure 18 – SEQ ID NO. 2

SEQUENCE LISTING

<160> NUMBER OF SEQ ID NOS: 15

<210> SEQ ID NO 1
<211> LENGTH: 9178
<212> TYPE: DNA
<213> ORGANISM: human

<400> SEQUENCE: 1

```
tgtggggaaa agcaagagag atcagattgt tactgtgtct gtgtagaaag aagtagacat      60
gggagactcc attttgttat gtgctaagaa aaattcttct gccttgagat tctgttaatc     120
tatgacctta cccccaaccc cgtgctctct gaaacgtgtg ctgtgtcaac tcagggttga     180
atggattaag ggcggtgcag gatgtgcttt gttaaacaga tgcttgaagg cagcatgctc     240
cttaagagtc atcaccactc cctaatctca gtacccagg  gacacaaaaa ctgcggaagg     300
ccgcagggac ctctgcctag gaaagccagg tattgtccaa ggtttctccc catgtgatag     360
tctgaaatat ggcctcgtgg gaagggaaag acctgaccgt cccccagccc gacacccgta     420
aagggtctgt gctgaggagg attagtataa gaggaaggaa tgccttcttgc agttgagaca    480
agaggaaggc atctgtctcc tgcctgtccc tgggcaatgg aatgtctcgg tataaaaccc     540
gattgtatgc tccatctact gagataggga aaaaccgcct tagggctgga ggtgggacct     600
gcgggcagca atactgcttt gtaaagcact gagatgttta tgtgtatgca tatccaaaag    660
cacagcactt aatcctttac attgtctatg atgccaagac cttttgttcac gtgtttgtct    720
gctgaccctc tccccacaat tgtcttgtga ccctgacaca tccccctctt tgagaaacac    780
ccacagatga tcaataaata ctaagggaac tcagaggctg gcgggatcct ccacatgctg    840
aacgctggtt ccccgggtcc ccttatttct ttctctatac tttgtctctg tgtcttttc     900
ttttccaaat ctctcatccc accttacgag aaacacccac aggtgtgtag ggcaaccca    960
cccctacatc tggtgcccaa cgtggaggct tttctctagg gtgaaggtac gctcgagcgt   1020
ggtcattgag gacaagtcga cgagagatcc cgagtacatc tacagtcagc cttacggtaa    1080
gcttgtgcgc tcggaagaag ctagggtgat aatgggggcaa actaaaagta aaattaaaag   1140
taaatatgcc tcttatctca gctttattaa aattcttta aaaagagggg gagttaaagt     1200
atctacaaaa aatctaatca agctatttca aataatagaa caattttgcc catggtttcc   1260
agaacaagga actttagatc taaaagattg gaaagaatt ggtaaggaac taaaacaagc     1320
aggtaggaag ggtaatatca ttccacttac agtatggaat gattgggcca ttattaaagc   1380
agctttagaa ccatttcaaa cagaagaaga tagcgtttca gtttctgatg cccttggaag   1440
ctgtataata gattgtaatg aaaacacaag gaaaaaatcc cagaaagaaa cggaaggttt   1500
acattgcgaa tatgtagcag agccggtaat ggctcagtca acgcaaaatg ttgactataa   1560
tcaattacag gaggtgatat atcctgaaac gttaaaatta aaggaaaaag gtccagaatt   1620
agtggggcca tcagagtcta aaccacgagg cacaagtcat cttccagcag gtcaggtgcc   1680
cgtaacatta caacctcaaa agcaggttaa agaaaataag acccaaccgc cagtagccta   1740
tcaatactgg cctccggctg aacttcagta tcggccaccc ccagaaagtc agtatggata   1800
tccaggaatg ccccccagcac cacagggcag ggcgccatac cctcagccgc ccactaggag   1860
acttaatcct acggcaccac ctagtagaca gggtagtgaa ttacatgaaa ttattgataa    1920
atcaagaaag gaaggagata ctgaggcatg gcaattccca gtaacgttag aaccgatgcc   1980
acctggagaa ggagcccaag agggagagcc tcccacagtt gaggccagat acaagtcttt   2040
```

```
ttcgataaaa atgctaaaag atatgaaaga gggagtaaaa cagtatggac ccaactcccc    2100
ttatatgagg acattattag attccattgc tcatggacat agactcattc cttatgattg    2160
ggagattctg gcaaaatcgt ctctctcacc ctctcaattt ttacaattta agacttggtg    2220
gattgatggg gtacaagaac aggtccgaag aaatagggct gccaatcctc cagttaacat    2280
agatgcagat caactattag gaataggtca aaattggagt actattagtc aacaagcatt    2340
aatgcaaaat gaggccattg agcaagttag agctatctgc cttagagcct gggaaaaaat    2400
ccaagaccca ggaagtacct gcccctcatt taatacagta agacaaggtt caaaagagcc    2460
ctatcctgat tttgtggcaa ggctccaaga tgttgctcaa aagtcaattg ccgatgaaaa    2520
agcccgtaag gtcatagtgg agttgatggc atatgaaaac gccaatcctg atgtcaatca    2580
gccattaagc cattaaaagg aaaggttcct gcaggatcag atgtaatctc agaatatgta    2640
aaagcctgtg atggaatcgg aggagctatg cataaagcta tgcttatggc tcaagcaata    2700
acaggagttg ttttaggagg acaagttaga acatttggag aaaatgttta taattgtggt    2760
caaattggtc acttaaaaaa gaattgtcca gtcttaaata aacagaatat aactattcaa    2820
gcaactacaa caggtagaga gccacctgac ttatgtccaa gatgtaaaaa aggaaaacat    2880
tgggctagtc aatgtcgttc taaatttgat aaaaatgggc aaccattgtc gggaaacgag    2940
caaaggggcc agcctcaggc cccacaacaa actgggcat tcccaattca gccatttgtt    3000
cctcagggtt tcaggaaca acaaccccca ctgtcccaag tgtttcaggg aataagccag    3060
ttaccacaat acaacaattg tccccgcca caagcgcag tgcagcagta gatttatgta    3120
ctatacaagc agtctctctg cttccagggg agccccaca aaaaatccct acaggggtat    3180
atggcccact gcctgagggg actgtaggac taatcttggg aagatcaagt ctaaatctaa    3240
aaggagttca aattcatact agtgtggttg attcagacta taaaggcgaa attcagttgg    3300
ttattagctc ttcaattcct tggagtgcca gtccaggaga caggattgct caattattac    3360
tcctgccata tattaagggt ggaaatagtg aaataaaaag aataggaggg cttggaagca    3420
ctgatccaac aggaaaggct gcatattggg caagtcaggt cacagagaac agacctgtgt    3480
gtaaggccat tattcaagga aaacagtttg aagggttggt agacactgga gcagatgtct    3540
ctatcattgc tttaaatcag tggccaaaaa attggcctaa acaaaaggct gttacaggac    3600
ttgtcggcat aggcacagcc tcagaagtgt atcaaagtac tgagatttta cattgcttag    3660
ggccagataa tcaagaaagc actgttcagc caatgattac ttcaattcct cttaatctgt    3720
ggggtcgaga tttattacaa caatgggtg cggaaatcac catgcctgcc ccattatata    3780
gccccacgag tcaaaaaatc atgaccaaga tgggatatat accaggaaag ggactaggga    3840
aaaatgaaga tggcattaaa gttccagttg aggctaaaat aaatcaagaa agagaaggaa    3900
tagggtatcc ttttaggggg cggccactgt agagcctcct aagcccatac cactaacttg    3960
gaaaacagaa aaaccggtgt gggtaaatca gtggccgcta ccaaaacaaa aactggaggc    4020
tttacattta ttagcaaatg aacagttaga aaagggtcac attgagcctt cgttctcacc    4080
ttggaattct cctgtgtttg taattcagaa gaaatcaggc aaatggcgta tgttaactga    4140
cttaagggct gtaaacgccg taattcaacc catggggcct ctccaacctg ggttgccctc    4200
tccagccatg atcccaaaag attggcctt aattataatt gatctaaagg attgcttttt    4260
taccatccct ctggcagagc aggattgcga aaaatttgcc tttactatac cagccataaa    4320
taataaagaa ccagccacca ggtttcagtg gaaagtgtta cctcagggaa tgcttaatag    4380
tccaactatt tgtcagactt ttgtaggttg agctcttcaa ccagttagag aaaagttttc    4440
```

```
agactgttat attattcatt atattgatga tattttatgt gctgcagaaa cgagagataa    4500
attaattgac tgttatacat ttctgcaagc agaggttgcc aatgctggac tggcaatagc    4560
atctgataag atccaaacct ctactccttt tcattattta gggatgcaga tagaaaatag    4620
aaaaattaag ccacaaaaag tagaaataag aaaagacaca ttaaaaacac taaatgattt    4680
tcaaaaatta ctaggagata ttaattggat tcggccaact ctaggcattc ctacttatgc    4740
catgtcaaat ttgttctcta tcttaagagg agactcagac ttaaatagta aaagaatatt    4800
aaccccagag gcaacaaaag aaattaaatt agtggaagaa aaaattcagt cagcgcaaat    4860
aaatagaata gatcccttag ccccactcca acttttgatt tttgccactg cacattctcc    4920
aacaggtatc attattcaaa atactgatct tgtggagtgg tcattccttc ctcacagtac    4980
agttaagact tttacactgt acttggatca aatagctaca ttaattggtc agacaagatt    5040
acgaataata aaattatatg gaaatgaccc agacaaaata gttgtccctt taaccaagga    5100
acaagttaga caagccttta tcaattctgg tgcatggcag attggtcttg ctaattttgt    5160
gggaattatt gataatcatt acccaaaaac aaagatcttc cagttcttaa aactgactac    5220
ttggattcta cctaaaatta ccagacgtga acctttagaa aatgctctaa cagtatttac    5280
tgatggttcc agcaatggaa aagcagctta cacaggaccg aaagaacgag taatcaaaac    5340
tccatatcaa tcggctcaaa gagcagagtt ggttgcagtc attacagtgt tacaagattt    5400
tgaccaacct atcaatatta tatcagattc tgcatatgta gtacaggcta caagggatgt    5460
tgagacagct ctaattaaat atagcatgga tgatcagtta aaccagctat tcaatttatt    5520
acaacaaact gtaagaaaaa gaaatttccc attttatatt actcatattc gagcacacac    5580
taatttacca gggcctttga ctaaagcaaa tgaacaagct gacttactgg tatcatctgc    5640
actcataaaa gcacaagaac ttcatgcttt gactcatgta aatgcagcag gattaaaaaa    5700
caaatttgat gtcacatgga acaggcaaa agatattgta caacattgca cccagtgtca    5760
aatcttacac ctgcccactc aagaggcagg agttaatccc agaggtctgt gtcctaatgc    5820
attatggcaa atggatgtca cgcatgtacc ttcatttgga agattatcat atgttcacgt    5880
aacagttgat acttattcac atttcatatg ggcaacttgc caaacaggag aaagtacttc    5940
ccatgttaaa aaacatttat tgtcttgttt tgctgtaatg ggagttccag aaaaaatcaa    6000
aactgacaat ggaccaggat attgtagtaa agctttccaa aaattcttaa gtcagtggaa    6060
aatttcacgt acaacaggaa ttccttataa ttcccaagga caggccatag ttgaaagaac    6120
taatagaaca ctcaaaactc aattagttaa acaaaaagaa gggggagaca gtaaggagtg    6180
taccactcct cagatgcaac ttaatctagc actctatact ttaaattttt taaacattta    6240
tagaaatcag actactactt ctgcagaaca acatcttact ggtaaaaaga acagcccaca    6300
tgaaggaaaa ctaatttggt ggaaagataa taaaaataag acatgggaaa tagggaaggt    6360
gataacgtgg gggagaggtt ttgcttgtgt ttcaccagga gaaaatcagc ttcctgtttg    6420 gataccact agacatttga agttctacaa tgaacccatt ggagatgcaa agaaaagggc    6480
ctccacggag atggtaacac cagtcacatg gatggataat cctatagaaa tatatgttaa    6540
tgatagtgta tgggtacctg gacccataga tgatcgctgc cctgccaaac ctgaggaaga    6600
agggatgatg ataaatattt ccattgggta tcgttatcct cctatttgcc tagggagagc    6660
accaggatgt ttaatgcctg cagtccaaaa ttggttggta gaagtaccta ctgtcagtcc    6720
catcagtaga ttcacttatc acatggtaag cgggatgtca ctcaggccac gggtaaatta    6780
tttacaagac ttttcttatc aaagatcatt aaaatttaga cctaaaggga aaccttgccc    6840
```

```
caaggaaatt cccaaagaat caaaaaatac agaagtttta gtttgggaag aatgtgtggc    6900
caatagtgcg gtgatattac aaaacaatga atttggaact attatagatt gggcacctcg    6960
aggtcaattc taccacaatt gctcaggaca aactcagtcg tgtccaagtg cacaagtgag    7020
tccagctgtt gatagcgact taacagaaag tttagacaaa cataagcata aaaaattgca    7080
gtctttctac ccttgggaat ggggagaaaa aagaatctct accccaagac caaaaatagt    7140
aagtcctgtt tctggtcctg aacatccaga attatggagg cttactgtgg cctcacacca    7200
cattagaatt tggtctggaa atcaaacttt agaaacaaga gattgtaagc cattttatac    7260
tatcgaccta aattccagtc taacagttcc tttacaaagt tgcgtaaagc ccccttatat    7320
gctagttgta ggaaatatag ttattaaacc agactcccag actataacct gtgaaaattg    7380
tagattgctt agttgcattg attcaacttt taattggcaa caccgtattc tgctggtgag    7440
agcaagagag ggcgtgtgga tccctgtgtc catggaccga ccatgggagg cctcaccatc    7500
cgtccatatt ttgactgaag tattaaaagg tgttttaaat agatccaaaa gattcatttt    7560
tactttaatt gcagtgatta tgggattaat tgcagtcaca gctacggctg ctgtagcagg    7620
agttgcattg cactcttctg ttcagtcagt aaactttgtt aatgattggc aaaagaattc    7680
tacaagattg tggaattcac aatctagtat tgatcaaaaa ttggcaaatc aaattaatga    7740
tcttagacaa actgtcattt ggatgggaga cagactcatg agcttagaac atcgtttcca    7800
gttacaatgt gactggaata cgtcagattt ttgtattaca ccccaaattt ataatgagtc    7860
tgagcatcac tgggacatgg ttagacgcca tctacaggga agagaagata atctcacttt    7920
agacatttcc aaattaaaag aacaaatttt cgaagcatca aaagcccatt taaatttggt    7980
gccaggaact gaggcaattg caggagttgc tgatggcctc gcaaatctta accctgtcac    8040
ttgggttaag accattggaa gtactacgat tataaatctc atattaatcc ttgtgtgcct    8100
gttttgtctg ttgttagtct gcaggtgtac ccaacagctc cgaagagaca gcgaccatcg    8160
agaacgggcc atgatgacga tggcggtttt gtcgaaaaga aaaggggggaa atgtgggaa    8220 aagcaagaga gatcagattg ttactgtgtc tgtgtagaaa aagtagaca tgggagactc    8280 cattttgtta tgtgttaaga aaaattcttc tgccttgaga ttctgttaat ctatgaccttt   8340 accccccaacc ccgtgctctc tgaaacgtgt gctgtgtcaa ctcagggttg aatggattaa    8400
gggcggtgca ggatgtgctt tgttaaacag atgcttgaag gcagcatgct ccttaagagt    8460
catcaccact ccctaatctc aagtacccag gacacaaaaa ctgcggaagg ccgcagggac    8520
ctctgcctag gaaagccagg tattgtccaa ggtttctccc catgtgatag tctgaaatat    8580
ggcctcgtgg gaagggaaag acctgaccgt cccccagccc gacacccgta aagggtctgt    8640
gctgaggagg attagtataa gaggaaggaa tgcctcttgc agttgagaca agaggaaggc    8700
atctgtctcc tgcctgtccc tgggcaatgg aatgtctcgg tataaaaccc gattgtatgc    8760
tccatctact gagataggga aaaaccgcct tagggctgga ggtgggacct gcgggcagca    8820
atactgcttt gtaaagcact gagatgttta tgtgtatgca tatccaaaag cacagcactt    8880
aatcctttac attgtctatg atgccaagac ctttgttcac gtgtttgtct gctgaccctc    8940
tccccacaat tgtcttgtga ccctgacaca tccccctctt tgagaaacac ccacagatga    9000
tcaataaata ctaagggaac tcagaggctg gcgggatcct ccatatgctg aacgctggtt    9060
ccccgggtcc ccttatttct ttctctatac tttgtctctg tgtctttttc ttttccaaat    9120
ctctcgtccc accttacgag aaacacccac aggtgtgtag gggcaaccca cccctaca    9178

<210> SEQ ID NO 2
```

<211> LENGTH: 494
<212> TYPE: PRT
<213> ORGANISM: human

<400> SEQUENCE: 2

```
Met Gly Gln Thr Lys Ser Lys Ile Lys Ser Lys Tyr Ala Ser Tyr Leu
1               5                   10                  15

Ser Phe Ile Lys Ile Leu Leu Lys Arg Gly Val Lys Val Ser Thr
                20                  25                  30

Lys Asn Leu Ile Lys Leu Phe Gln Ile Glu Gln Phe Cys Pro Trp
                35                  40                  45

Phe Pro Glu Gln Gly Thr Leu Asp Leu Lys Asp Trp Lys Arg Ile Gly
50                  55                  60

Lys Glu Leu Lys Gln Ala Gly Arg Lys Gly Asn Ile Ile Pro Leu Thr
65                  70                  75                  80

Val Trp Asn Asp Trp Ala Ile Ile Lys Ala Ala Leu Glu Pro Phe Gln
                85                  90                  95

Thr Glu Glu Asp Ser Val Ser Val Ser Asp Ala Leu Gly Ser Cys Ile
                100                 105                 110

Ile Asp Cys Asn Glu Asn Thr Arg Lys Lys Ser Gln Lys Glu Thr Glu
            115                 120                 125

Gly Leu His Cys Glu Tyr Val Ala Glu Pro Val Met Ala Gln Ser Thr
            130                 135                 140

Gln Asn Val Asp Tyr Asn Gln Leu Gln Glu Val Ile Tyr Pro Glu Thr
145                 150                 155                 160

Leu Lys Leu Glu Gly Lys Gly Pro Glu Leu Val Gly Pro Ser Glu Ser
                165                 170                 175

Lys Pro Arg Gly Thr Ser His Leu Pro Ala Gly Gln Val Pro Val Thr
                180                 185                 190

Leu Gln Pro Gln Lys Gln Val Lys Glu Asn Lys Thr Gln Pro Pro Val
                195                 200                 205

Ala Tyr Gln Tyr Trp Pro Pro Ala Glu Leu Gln Tyr Arg Pro Pro Pro
                210                 215                 220

Glu Ser Gln Tyr Gly Tyr Pro Gly Met Pro Pro Ala Pro Gln Gly Arg
225                 230                 235                 240

Ala Pro Tyr Pro Gln Pro Pro Thr Arg Arg Leu Asn Pro Thr Ala Pro
                245                 250                 255

Pro Ser Arg Gln Gly Ser Glu Leu His Glu Ile Ile Asp Lys Ser Arg
                260                 265                 270

Lys Glu Gly Asp Thr Glu Ala Trp Gln Phe Pro Val Thr Leu Glu Pro
                275                 280                 285

Met Pro Pro Gly Glu Gly Ala Gln Glu Gly Glu Pro Pro Thr Val Glu
290                 295                 300

Ala Arg Tyr Lys Ser Phe Ser Ile Lys Met Leu Lys Asp Met Lys Glu
305                 310                 315                 320

Gly Val Lys Gln Tyr Gly Pro Asn Ser Pro Tyr Met Arg Thr Leu Leu
                325                 330                 335

Asp Ser Ile Ala His Gly His Arg Leu Ile Pro Tyr Asp Trp Glu Ile
                340                 345                 350

Leu Ala Lys Ser Ser Leu Ser Pro Ser Gln Phe Leu Gln Phe Lys Thr
                355                 360                 365

Trp Trp Ile Asp Gly Val Gln Glu Gln Val Arg Arg Asn Arg Ala Ala
                370                 375                 380

Asn Pro Pro Val Asn Ile Asp Ala Asp Gln Leu Leu Gly Ile Gly Gln
385                 390                 395                 400
```

```
Asn Trp Ser Thr Ile Ser Gln Gln Ala Leu Met Gln Asn Glu Ala Ile
            405                 410                 415

Glu Gln Val Arg Ala Ile Cys Leu Arg Ala Trp Glu Lys Ile Gln Asp
        420                 425                 430

Pro Gly Ser Thr Cys Pro Ser Phe Asn Thr Val Arg Gln Gly Ser Lys
            435                 440                 445

Glu Pro Tyr Pro Asp Phe Val Ala Arg Leu Gln Asp Val Ala Gln Lys
        450                 455                 460

Ser Ile Ala Asp Glu Lys Ala Arg Lys Val Ile Val Glu Leu Met Ala
465                 470                 475                 480

Tyr Glu Asn Ala Asn Pro Asp Val Asn Gln Pro Leu Ser His
                485                 490

<210> SEQ ID NO 3
<211> LENGTH: 20
<212> TYPE: DNA
<213> ORGANISM: artificial
<220> FEATURE:
<223> OTHER INFORMATION: forward primer corresponding to nucleotides
      4272-4291 of HERV-K102

<400> SEQUENCE: 3
tggcagagca ggattgtgaa                                              20

<210> SEQ ID NO 4
<211> LENGTH: 20
<212> TYPE: DNA
<213> ORGANISM: artificial
<220> FEATURE:
<223> OTHER INFORMATION: reverse pcr primer corresponding to nucleotides
      4565-4546 of HERV-K102

<400> SEQUENCE: 4
cagatgctat tgccagtcca                                              20

<210> SEQ ID NO 5
<211> LENGTH: 16
<212> TYPE: PRT
<213> ORGANISM: artificial
<220> FEATURE:
<223> OTHER INFORMATION: epitope corresponding to nucleotides 6473-6520
      of HERV-K102

<400> SEQUENCE: 5

Lys Arg Ala Ser Thr Glu Met Val Thr Pro Val Thr Trp Met Asp Asn
1               5                   10                  15

<210> SEQ ID NO 6
<211> LENGTH: 17
<212> TYPE: PRT
<213> ORGANISM: artificial
<220> FEATURE:
<223> OTHER INFORMATION: epitope corresponding to nulceotides 7229-7279
      of HERVK-102

<400> SEQUENCE: 6

Leu Glu Thr Arg Asp Cys Lys Pro Phe Tyr Thr Ile Asp Leu Asn Ser
1               5                   10                  15
Ser

<210> SEQ ID NO 7
<211> LENGTH: 295
<212> TYPE: DNA
<213> ORGANISM: human
```

<400> SEQUENCE: 7

```
ctggcagagc aggattgcga aaaatttgcc tttactatac cagccataaa taataaagaa      60
ccagccacca ggtttcagtg gaaagtgtta cctcagggaa tgcttaatag tccaactatt     120
tgtcagactt ttgtaggttg agctcttcaa ccagttagag aaaagttttc agactgttat     180
attattcatt atattgatga tattttatgt gctgcagaaa cgagagataa attaattgac     240
tgttatacat ttctgcaagc agaggttgcc aatgctggac tggcaatagc atctg          295
```

<210> SEQ ID NO 8
<211> LENGTH: 30
<212> TYPE: DNA
<213> ORGANISM: human

<400> SEQUENCE: 8

```
tgacggggtc acccacactg tgcccatcta                                        30
```

<210> SEQ ID NO 9
<211> LENGTH: 30
<212> TYPE: DNA
<213> ORGANISM: human

<400> SEQUENCE: 9

```
ctagaagcat ttgcggtgga cgatggaggg                                        30
```

<210> SEQ ID NO 10
<211> LENGTH: 128
<212> TYPE: DNA
<213> ORGANISM: human

<400> SEQUENCE: 10

```
tcttcaacca gttagagaaa agttttcaga ctgttatatt attcattata ttgatgatat      60
tttatgtgct gcagaaacga gagataaatt aattgactgt tatacatttc tgcaagcaga     120
ggttgcca                                                              128
```

<210> SEQ ID NO 11
<211> LENGTH: 120
<212> TYPE: DNA
<213> ORGANISM: human

<400> SEQUENCE: 11

```
tcttcaacca gttagagaaa agttttcaga ctgttatatt attcattata ttgatgatat      60
tttatgtgct gcagaaacga agataaatt aattgactgt tatacatttc tgcaagcaga     120
```

<210> SEQ ID NO 12
<211> LENGTH: 120
<212> TYPE: DNA
<213> ORGANISM: Human immunodeficiency virus

<400> SEQUENCE: 12

```
ttagagcctt ttagaagaaa atatccagac atagttatct gtcaatacgt agatgatttg      60
tatgtagcat ctgacttaga aatagagcag cagcatagaa caaaaataga ggaactgaga     120
```

<210> SEQ ID NO 13
<211> LENGTH: 28
<212> TYPE: DNA
<213> ORGANISM: artificial sequence
<220> FEATURE:
<223> OTHER INFORMATION: Forward primer for RT PCR

<400> SEQUENCE: 13

```
tcttcaacca gttagagaaa agttttca                                         28

<210> SEQ ID NO 14
<211> LENGTH: 18
<212> TYPE: DNA
<213> ORGANISM: artificial sequence
<220> FEATURE:
<223> OTHER INFORMATION: Reverse primer for RT PCR

<400> SEQUENCE: 14
tggcaacctc tgcttgca                                                    18

<210> SEQ ID NO 15
<211> LENGTH: 23
<212> TYPE: DNA
<213> ORGANISM: artificial sequence
<220> FEATURE:
<223> OTHER INFORMATION: Probe for RT PCR

<400> SEQUENCE: 15
gcagcacata aaatatcatc aat                                              23
```

HUMAN ENDOGENOUS RETROVIRUS K102 WITH FOAMY-VIRUS-LIKE PROPERTIES AND USES THEREOF

PRIOR APPLICATION INFORMATION

This application claims the benefit of Canadian Patent Application 2,501,301, filed Mar. 18, 2005 and U.S. Provisional Patent Application 60/663,263, filed Mar. 21, 2005.

FIELD OF THE INVENTION

The present invention relates to the preparation of novel vector systems, new diagnostics and prognostics, and new screening procedures for identification of therapeutic agents.

BACKGROUND OF THE INVENTION

The notion of gene therapy to insert novel genes or corrected genes into cells of humans as a form of medical therapy has been a dream since at least the 70's. This dream was spurred on by the many advances made in molecular biology, with the ability to analyze and change segments of DNA. One such advance arguably has to include the technique of polymerase chain reaction (PCR). This technique involves repeated amplification cycles of copying the sequence identified by primer sets, each new round beginning with the dissociation of the newly transcribed double stranded cDNA, reannealing of primers, and 'primer extension'. Once this was adapted to gene sequencing, it reduced the amount of time to sequence several hundred based pairs from about a week to a matter of hours or minutes. And so the Human Genome project was completed many years ahead of predictions.

With the completion of the sequencing of the genome, it was discovered the human genome contains many forms of repetitive elements one of these being endogenous retroviruses, or remnants of endogenous retroviruses. By far, most of these are not much more than a set of no longer related left and right long terminal repeats (LTRs). Perhaps as much as 5 to 8% of the human genome contains bits and pieces of endogenous retroviruses. The more complete forms are fewer in number and constitute about 0.2% of the human genome. When one considers how big the genome is (3.4 trillion base pairs), that is a lot of DNA taken up by invading "retroelements'.

This saturation of the genome by once mobile elements and the passing on from generation to generation, has caused many to wonder what are they doing there. There is growing evidence that these endogenous retroviruses may play important biological roles. These roles include the formation of syncytiotrophoblast in the development of the human placenta. For human endogenous retroviruses of the L type (HERV-L), interference with exogenous viral replication through expression of antisense mRNA, is another proposed role. Many postulate these once mobile elements may have contributed to genomic diversity and thus, evolution of the species. The expression of endogenous retroviruses (and partial forms) has been linked to disease, particularly chronic diseases, and is more frequent with aging. Many of these illnesses may be characterized by autoimmune activity (diabetes, multiple sclerosis, arthritis etc.) and in others, neurodegeneration (Alzheimer's, Parkinson's, and dementia associated with aging).

To date no gene therapy has received marketing approval in Canada or in the United States despite the fact the first gene therapy was performed on Sep. 14, 1990. There are many problems, not the least of which concerns immunogenicity issues. This term refers to the notion that vectors used for gene transfer are foreign to humans and this enables humans to mount immunological responses both antibody based and cell mediated. This means after the first exposure there is a risk of an immunological reaction with each subsequent injection. Sometimes these reactions are manageable, other times they are not and can be deadly. Gene therapy clinical trials were halted in 1998 in the US upon death of a young male adult following an anaphylactic reaction to an adenovirus vector.

Other untoward side effects of gene therapy even when performed ex vivo (cells are transfected in the laboratory and then re-injected back to the same individual) concerns leukemia. In 2002, a first then second case of leukemia occurred in clinical trials in France using the murine leukemia virus as a vector, and gene therapy clinical trials were halted. Here the retrovirus vector, genetically devoid of transforming sequences, nevertheless led to cancer due to insertional mutation (first case) and insertional activation (second case) of a normal gene LMO-2, an oncogene responsible for childhood leukemias. The safety and efficacy of gene therapies is yet to be shown particularly for retroviral vectors derived from retroviruses that are known to naturally induce leukemias.

Additional protective strategies are usually employed in the construction of gene therapy vectors to ensure only one round of replication occurs. This is because to date, the vectors chosen have been derived from disease associated animal viruses and one would not want to start a new epidemic if fully functional infectious vectors were instead used. They are usually built in two or more pieces, so that the functional genes required for packaging the cDNA are provided on a separate element from those genes needed for integration into the host genome. Because these various parts are on different strips of cDNA, this only permits one round of replication and one chance for integration if derived from the "packaging cell" where both elements have been transfected.

Restricting replication to a single round helps to prevent the establishment of a viremia (which thereby decreases the chance of adverse effects such as a leukemia for a leukemic retrovirus, or immune deficiency for an AIDS like lentivirus). However, this has the disadvantage that most host cells will not be transfected by the vector and thus the gene is not delivered to sufficient number of cells in the host for the therapy to have value. This intrinsic limitation of retroviral vectors injected in vivo, is why for blood related disorders, usually bone marrow stem cells are isolated, transfected in vitro, and tested and enumerated before being re-implanted back into the host.

Human endogenous retroviruses (HERVs) constitute about 0.5% of the human genome, but the only HERV family known to express virus-like particles is HERV-K (1-3). None of the HERVs described so far has been shown to be infectious (3), but genetic evidence suggests some members of HERV-K, such as HERV-K102, K107-K109, K113 13, might be either infectious or at least recently active in reintegrating within the genome (4). Up to 50 different copies of HERV-K are present in the human genome, but few of these contain full-length genes encoding viral structural proteins (reviewed in 1). According to a more recent paper, 41/59 of long viral open reading frames (vORFs) are HERV-K betaretroviral and the human genome contains "intact" 17 gag, 13 pol and 29 envelope genes. Five of 29 envelope genes carry a specific 292 by deletion and are Type I HERV-K (*human mouse mammary tumor virus-like group* 2 (HML-2)) (Villensen et al., 2004).

The prototype HERV-K10 was first identified in the human genome by virtue of its homology to the exogenous mouse mammary tumor virus (MMTV) (5), although HERV-K10 is thought to be defective (5). Subsequently 6 groups with homology to the mouse mammary tumor virus were identified and were named HML-1 through HML-6 (where HML refers to Human Mammary tumor virus Like) (6, 7). More recently 25 HERV-K10-like elements related to HERV-K102 (belonging to the HML-2 subfamily) have been described (7). Many HERV-K proviruses have been mapped and cloned (8,9) through the human genome project. These analyses have further revealed there are two types of HERV-K (HML-2) proviral genomes differing by the presence (Type II) or absence (Type I) of a 292 bp segment at the pol-env boundary (10). HERV-K102 (GenBank AF164610), a member of the Type I family, has been mapped to chromosome 1 and is closely related to K10 (M14123, Type I), K101 (AF164609 Type I), K103 (AF164611, Type I) K107 (AF164613, Type I), K108 (AF164614, AF074086, Type II at 7p22.1), K109 AF164615 Type II, and as well as K113 (GenBank AY037928, Type II) at about 98% homology at the nucleotide level when one excludes the gap at the pol-env boundary in Type I (10, 11). For the remainder of this disclosure, HERV-BZU will refer to both Type I and Type II HERV-K (HML-2) as they are related at about 98% homology.

No HERV has been shown to be infective nor has an infectious foamy retrovirus (spumavirus) originating from humans yet been found. (Heinkelein et al., 2005).

Since Type I HERV-K (HML-2) particles are expressed in the placenta (Simpson et al., 1996), and become reactivated in the adult under certain conditions, most likely this means humans would be immunologically tolerant to these particles and associated proteins. Thus, the vector would be less likely to cause disease. This would provide a distinct advantage over current gene therapy vectors as there would be little risk of immunological or other adverse reactions using HERV-BZU as the vector. Thus, HERV-BZU could be repeatedly injected for one purpose, or could be subsequently used for a different purpose with minimal risk of anaphylactic shock or other immunological adverse reactions. Additionally, HERV-BZU lacks the immunosuppressive domain located within the transmembrane region of most retroviral envelope antigens, and thus, this again reduces the risk of pathological events.

Current retroviral vectors such as Murine Leukemia Virus (MLV) vectors have additional limitations in that cells must be replicating in order for infection and integration to occur. It is possible that a HERV-BZU type vector in analogy to foamy virus vectors, may infect both non-replicating and replicating cells, indicating a broader usefulness to target many cell types. In this regard it would be particularly suited to stem cell gene therapy, as many stem cells exist in non-replicative phases. It is recognized that the combination of gene therapy with autologous stem cell therapy is one area of medicine expected to grow significantly over the next few years. This is expected to have the most potential for more immediate clinical applications as the transfection occurs in vitro, is more easily controlled, and can be tested for any unexpected alterations before injection back into the host.

Overall foamy virus or foamy-virus-like vectors have many advantages over other retroviral vectors (Trobridge et al, 2002, Hill et al, 1999, Mergia & Heinkelein, 2003). Indeed when replication competent, they can and do infect many cell types in the body, and can cross the blood brain barrier (important for therapy of neurological disorders) (Heinkelein et al, 2005. They do not and have not been associated with disease whether naturally or experimentally transmitted. But there are three main concerns about using replication competent virus vectors: 1) integration could lead to insertional mutagenesis, 2) integration could lead to activation of oncogenes and thus tumor formation, 3) recombination could lead to a new epidemic, for example like HIV. The integration sites of foamy viruses starts with "TGTG" and is evidence of an asymmetric integration process. This type of integration appears to be common to HERV-BZU, as all family members also contain the "TGTG" sequence motif at the 5 end of the provirus but not other HERVs (except HERV-L which lacks env and thus cannot be active). According to a recent investigation, the preferred integration site for foamy viruses appear to be CpG islands rather than expressed genes, making foamy virus vectors the least likely to be associated with insertional mutations of genes (Trobridge et al, 2006). As well, foamy virus was recently found to be naturally oncolytic (Heinkelein et al, 2005), a unique feature which would safeguard the host from inadvertent tumor formation. Apparently foamy viruses cannot be pseudotyped by Env from other types of retroviruses (Meirering & Linial, 2001) making recombinants with exogenous retroviruses significantly more difficult. Along this same line Patience et al, 1998 have already shown Type I HERV-K particles do not package sequences from exogenous retroviruses, indicating HERV-BZU based vectors would be less likely than most to generate recombinants.

Finally, HERV-K102 based foamy like viral vectors, are not expected to increase the risks associated with its use over and above normal, as this virus naturally replicates in humans (see below) and has existed in the human genome since the divergence of man from apes, some 5 million years ago. To the best of our knowledge, there is no other existing or proposed virus gene therapy vector which has this proven track record. As also elucidated below, we provide evidence that HERV-K102 expression is directly antagonistic to HIV infectivity (see model and explanation), and we additionally propose may be a newly described host defense system against viral and tumor transformation. Thus, we suggest if gene therapy is to move forward for the cure of various diseases or for the prevention and control of intractable infectious diseases (like HIV and prion diseases), we predict only HERV-BZU will be able to safety and effectively transfect genes or gene products.

SUMMARY OF THE INVENTION

According to a first aspect of the invention, there is provided a vector system comprising a nucleic acid molecule encoding a functional HERV Type I pol polypeptide.

According to a second aspect of the invention, there is provided a method of recovering HERV particles comprising:
(a) providing a quantity of cells comprising a functional HERV Type I;
(b) incubating the cells under conditions inducing HERV Type I expression; and
(c) recovering HERV-like particles.

According to a third aspect of the invention, there is provided a method of detecting Type I HERV-element expression in a sample comprising:
providing a sample of interest suspected of containing HERV Type I expression products;
adding an HERV Type I-specific reagent to the sample;
incubating the sample and the reagent under conditions promoting interaction between the reagent and the expression products if present, and
detecting interaction between the reagent and the expression products, wherein a positive signal indicates that the expression products are present in the sample and a negative signal indicates that the expression products are not present in the sample.

According to a fourth aspect of the invention, there is provided a method of identifying an agent capable of modulating HERV Type I activation comprising:

adding a test agent to a sample comprising at least one HERV Type I element; and determining if the test agent 1) activates HERV Type I as indicated by expression of HERV Type I wherein said expression is greater than HERV Type I expression in a HERV Type I expression control or 2) inhibits HERV Type I as indicated by a lower HERV Type I expression compared to a control.

BRIEF DESCRIPTION OF THE FIGURES AND TABLES

FIG. 1. Vacuolation in Cord Blood (CB) is Inducible and Blocked by IL-2/PHA Treatment FIG. 2. Induction of Vacuolation (Day 7) was Independent of Source of Serum FIG. 3. Electron Microscopy Showing Extreme Vacuolation FIG. 4. Immature Particles of about 100 nm Found by EM FIG. 5. Forward (SEQ ID No 3) and Reverse (SEQ ID No. 4) Primer Set for HERV-K102 poi for Regular PCR.

FIG. 6. Time Course for induction of HERV-K pol mRNA by regular PCR

FIG. 7. Sequence of mRNA for HERV-K pal from PCR Product of CB (SEQ ID No. 7).

FIG. 8. HERV-K102 Envelope Sequences for Synthetic Peptides ML-4 (SEQ ID No. 5) and ML-5 (SEQ ID No. 6).

FIG. 9. Immunohistology With Rabbit Antibodies to ML-4 and ML-5 Peptides Shows Induction of HERV-K102 Envelope Protein by Day 7

FIG. 10. Western Blot with ML-4 on Proteins Immunoprecipitated with ML-4 or ML-5 Comparing Day 0 to Day 7

FIG. 11. Lytic Infection Only seen with MRC-5 not HFL-1 or Vero Cells

FIG. 12. RT-PCR Confirms Infection in both MRC-5 cells and in Vero (Green Monkey) Cells (but infectivity not transferred by supernatants to MRC-5 cells.

FIG. 13. Titration and Comparison of the Relative Sensitivities of β-actin vs. HERV-K102 pol FIG. 14. In Vivo Evidence for Activity: Putative Particles in Human Plasma FIG. 15. HERV-K102 Sequence, Primers and Probe for Real Time PCR (Quantitative and Relative ddCt Ratios) Are Unlikely to Amplify HIV Sequences. K102 is SEQ ID No. 10; K101 is SEQ ID No. 11; and HIV-1 is SEQ ID No. 12.

FIG. 16. Model for HIV Antagonism by HERV-K102

FIG. 17. HERV-K102 nucleotide sequence (SEQ ID NO. 1)

FIG. 18. HERV-K102 pol peptide sequence (SEQ ID NO. 2)

Table 1. Cultured Cord Blood Acquires HERV-K102 cDNA During Culture

Table 2. HERV-K102 (DNA) Relative Levels are Increased in MS Patient's PBMC and Increases when Cultured in Vitro by Real Time (Quantitative) PCR.

Table 3 Summary of HERV-K102 ddCt Ratios in Plasma

Table 4. Study of 22 HIV Viremic Samples for HERV-K102 ddCt Levels

Table 5. Excess HERV-K102 DNA Templates are Also Detected in Plasma Samples from Patients with Other Blood-borne Viruses Table 6. Serology for HERV-k102 Envelope Reactivity by ELISA with Synthetic Peptides Table 7. Screening for Agents able to Modulate HERV-K102 Replication (cDNA Production) in Cultured Cord Blood Cells Table 8. Increase in HERV-K102 cDNA Induced is induced in Cultured Cord Blood but Does NOT Occur in Cultured PBMC Depleted of Monocytes Table 9. Summary of Similarities of HERV-K102 with Prototypic Foamy Virus

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

This invention pertains to the discovery of vacuolation-associated HERV-K102 or HERV-K102 like provirus expression correlated with particle formation in and infectivity from normal Cord Blood (CB) (blood drawn from the expelled placenta) and Peripheral Blood Mononuclear Cells (PBMCs) (purified from adult blood). This provirus is induced upon in vitro culture of these mononuclear cells in the notable absence of exogenous cytokines or activators and occurs when cultured in IMDM media rather than RPMI which is normally used.

As will be appreciated by one of skill in the art and as described herein, these results indicate that the HERV-K102 has several useful properties which may be used advantageously, as described below.

In a preferred embodiment, human endogenous retroviral element or HERV-element refers to HERV-K102, GenBank Accession Number AF164610, also shown in FIG. 17 (SEQ ID No. 1). In other embodiments, HERV-element refers to an HERV-K (HML-2) Type I element having at least 90% homology at the nucleotide level to SEQ ID NO 1, or having at least 91% homology, at least 92% homology, at least 93%, at least 94%, at least 95%, at least 96%, at least 97%, at lest 98% or at least 99% homology to HERV K102 (SEQ ID NO. 1) over the entire length of the HERV-K102 sequence or over a specific region thereof as discussed below. As will be appreciated by one of skill in the art, regions of the HERV-element sequence likely to tolerate alterations in sequence can be determined experimentally or can be determined by comparison of known HERV Type I sequences for regions of non-homology. It is noted that programs capable of such comparisons are well-known in the art.

As discussed above, it is noted that Type II HERV-elements differ from Type I HERV elements in that Type II elements include a 292 bp insert at the pol/env boundary. As such, it is noted that a Type II HERV-element may be converted to a Type I element by deletion of this 292 bp region.

In yet other embodiments, there is provided a polypeptide or a nucleic acid molecule encoding a polypeptide which is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homologous to the HERV-K102 polypeptide as shown in FIG. 18 (SEQ ID No. 2) over the entire length of the HERV-K102 polypeptide or over a specific region thereof as discussed below. As will be appreciated by one of skill in the art, regions of the HERV-K102 polypeptide likely to tolerate alterations in sequence can be determined experimentally or can be determined by comparison of known HERV sequences (examples of which are provided above, see specifically SEQ ID Nos 3 and 4 as well as SEQ ID NO. 4 and 5) for regions of non-homology or non-conservation. It is noted that programs capable of such comparisons are well-known in the art. In some embodiments, expression of the polypeptide may be driven by an HERV LTR as described herein or may be driven by a non-native promoter, also as discussed herein.

In a preferred embodiment, the HERV-element as discussed above is used in the construction of a vector system comprising a nucleic acid molecule encoding a functional HERV-K Type I (HML-2) pol polypeptide, for example, as described above, that is, having at least 80% homology to SEQ ID NO. 2. In some embodiments, the homology is to the entire pol polyprotein as discussed above. As discussed below, such systems are well-known for other retroviruses and retroelements, including foamy viruses. As such, a wide variety of suitable vector systems may be designed as discussed in detail below. In some embodiments, the vector system comprises a single vector element which comprises a nucleic acid molecule encoding the Type I HERV-K nucleotide sequences and including sufficient Type I HERV-K (HML-2) LTR sequences to drive expression of said vector and expression of functional proteins from said LTR. In these embodiments, the nucleic acid molecule may be as discussed above, that is, for example, at least 90% homologous to SEQ ID NO. 1. In some embodiments, the HERV Type I nucleic acid molecule may be a chimeric molecule comprised of sequences from more than one specific HERV-K (HML-2). Indeed, we know HERV-K102 exists as quasi-species in that during replication the resulting nucleotides can differ by several percentages and often stop codons are eliminated (Wang-Johanning et al, 2003, 2001, Muster et al, 2003). In other embodiments, the Type I HERV-K (HML-2) vector may be further engineered to include a multiple cloning site or insertion site for the insertion of foreign (non-HERV) nucleic acid molecules as discussed below or may have inserted therein a therapeutic insert, for example, a viral or bacterial antigen, an siRNA, an antisense RNA, a therapeutic gene for gene replacement or a lytic or otherwise 'killer' gene as discussed below. As will be apparent to one of skill in the art and as discussed below, a variety of insertion sites within the retroelement are known in the art and can easily be determined.

In other embodiments, the vector system comprises a first vector element which comprises a nucleic acid molecule encoding a functional HERV-K polypeptide sequence as discussed above. A second vector element comprises a therapeutic insert as discussed herein and sufficient HERV-BZU sequence that the therapeutic insert will be packaged into particles, as discussed below. Specifically, in these embodiments, expression of the HERV-K may be driven by a non-native promoter such that replicative or infective particles are not produced. As a consequence, the elements for particle formation are produced in trans from separately cloned sequences and both clones for the particle and the engineered sequence are then packaged together when expressed in the same "packaging" cell.

It is of note that either of the above-described vector systems can be used in a variety of means as discussed below. It is further noted that it was previously believed that the Type I HERV-K (HML-2) proviral elements were non-infectious because they lack the REC/REV/REX domain, and so it was thought, the RNA genome could not be exported from the nucleus to the endoplasmic reticulum where the particles form.

For example, the above vector systems can be used to transform suitable cells in vitro for the generation of infectious particles, (which could be replication competent or replication incompetent) as discussed below. In accordance with an aspect of the invention, there is provided a method of HERV particle production comprising: transforming or transfecting cells with a vector system comprising a nucleic acid molecule or incubating the cells under conditions inducing HERV-K Type I expression; and recovering HERV-K like particles.

It is noted that as used above, 'HERV-like' refers to the fact that the particle may be composed of HERV-K sequences but additional foreign sequences may also be present with or without deleting some of the HERV-K sequences.

It is further noted that the recovery, isolation and purification of such particles is well-known in the art, such as the Qiagen Ultrasensitive Virus (DNA+RNA) Isolation kit which can be used to extract particles from plasma, by isolation on 20% sucrose, or by using other materials.

As discussed herein, natural expression of Type I HERV-K (HML-2) elements is linked to the presence in a cell of an infectious agent. As will be appreciated by one of skill in the art, 'infection' as used herein refers to viral infections, such as HIV and CMV, HHV7, EBV, Hepatitis C, Hepatitis and other bloodborne infections potentially including prions, as well as to autoimmune diseases such as multiple sclerosis, or as we also demonstrate Chronic Fatigue Syndrome (CFS) which may also have a suspected viral etiology. It is further noted that in many tissues, Type II HERV-K (HML-2) expression is constitutive and therefore detection of HERV-K Type I (HML-2) expression must rely on reagents, for example, at least one primer(s) and or at least one epitope, that are unique to Type I. As will be appreciated by one of skill in the art, such regions may be determined by comparison of Type I and Type II sequences as discussed above. In a preferred embodiment, at least one of the primers and/or epitopes could be derived from the pol/env boundary region of the Type I HERV-element, that is, the region of Type I HERV-K corresponding to the region flanking the 292 bp insert at the pol/env boundary found in Type II HERVs but absent in Type I. Exemplary sequences are also described below.

Thus, in a preferred embodiment, there is provided a method of detecting Type I HERV-K (HML-2) element expression in a sample comprising providing a sample of interest suspected of containing HERV-K Type I expression products; adding an HERV Type I-specific reagent to the sample; incubating the sample and the reagent under conditions promoting interaction between the reagent and the expression products if present; and detecting interaction between the reagent and the expression products, wherein a positive signal indicates that the expression products are present in the sample and a negative signal indicates that the expression products are not present in the sample. For example, the expression products may be HERV-K Type I RNA, non-integrated or infectious DNA, polypeptide, peptides or particles. The polypeptide, peptides or particles may be detected using antibodies which interact with a HERV-K Type I-specific region of the HERV-element (for example ML-4 (SEQ ID No. 5) and ML-5 (SEQ ID No. 6) as discussed below), as discussed above and the interaction may be detected using means known in the art, for example, secondary antibodies coupled with a detectable marker. In other embodiments, wherein HERV-K Type I RNA or non-integrated or infectious DNA is detected, at least one primer derived from an HERV-K Type I unique region may be used in combination with a second primer derived from HERV-K Type I which may also be unique but not necessarily so (see for example FIG. 5). In these embodiments, the primers bind to HERV-K Type I RNA or DNA and are then detected by subjecting the sample to conditions (including reagents) suitable for nucleotide amplification and the amplification product is detected using any of a variety of means known in the art.

As discussed below, this method may be used to detect the presence of an active infection, for example, an unknown viremia in a sample of interest, or to detect the remission or recession or elimination of a known infection in a sample and therefore in a patient (ie to monitor if a therapy is working in vivo).

In another embodiment of the invention, there is provided a method of identifying an agent capable of modulating HERV-K Type I activation comprising: adding a test agent to a sample comprising at least one HERV-K Type I element; and determining if the test agent 1) activates HERV-K Type I as indicated by expression of HERV Type I wherein said expression is greater than HERV Type I expression in a HERV Type I expression control or 2) inhibits HERV Type I as indicated by a lower HERV Type I expression compared to a control. The agent may be for example a peptide or peptide fragment, a protein, a small molecule, chemical, drug, natural product, hormone, or may otherwise induce a change in the cellular environment. As will be appreciated by one of skill in the art, in some embodiments, such an assay may be used to determine the effect of new or existing pharmaceutical treatments, for example, medicaments for other diseases or disorders, on HERV-K Type I expression, as discussed below.

As will be appreciated by one of skill in the art, such agents may be used for a variety of purposes, for example, for treating diseases where it may be advantageous to quieten HERV-K102 such as in Chronic Fatigue, Critical to this invention of a new provirus vector and its usefulness to humans, are the notions of the natural infectivity of the endogenous human retrovirus(es), the enhanced safety and utility of such a derived vector bestowed by immunological tolerance within the human population, the natural repressed state which occurs upon integration into human cells, the natural induction when cells become virally or tumor transformed and its non-pathogenicity due in part to co-evolution with the human species over 5 million years or so.

In addition, because the described provirus appears to functionally resemble spumaviruses or foamy retroviruses, there are additional advantages over existing gene therapy vectors including: inferred lack of capability for disease causation in any host species, wide host range, and wide range of cell types which may be infected, importantly including non-replicating and replicating cells. Foamy retrovirus also cross the blood-brain barrier, a distinct advantage for the treatment of neurological disease. As well of the retroviruses which stably integrate into genomes, the integration of FV is less likely to cause problems.

As discussed herein, the novel retrovirus can be used in a number of applications. For example, in some embodiments, HERV-BZU or an element derived therefrom is used as a human foamy virus vector. In these embodiments, HERV-BZU and/or genetically modified derivatives thereof are used as a new and improved gene therapy vector in general, as described below, or alternatively as a shuttle vector for traditional vaccination examples include but are by no means limited to foreign proteins of viruses such as HIV, HTLV, hepatitis B, hepatitis C, human papilloma virus, cytomegalovirus, HSV or influenza virus; bacterial proteins, such as outer membrane proteins of *Campylobacter, E. coli, Salmonella* and the like; or bacterial toxins. Here dendritic cells could be transfected in vitro and injected into humans or the vector itself injected.

As will be appreciated by one of skill in the art and as discussed below, the HERV-BZU vector may include an inducible promoter for driving expression of the HERV construct under certain conditions, a cell-specific promoter for expression in certain types of cells or a constitutive promoter. It is of note that examples of such promoters are well known in the art.

The HERV-BZU vector may include an intact copy of HERV-K102 or other HERV-K Type I (HML-2) element or fragments thereof as discussed above sufficient for autonomous insertion and replication of the retroelement. As discussed herein, the vector may also include suitable insertion sites for insertion of non-HERV sequences, that is, the therapeutic insert, for example, but by no means limited to antisense RNA, mRNA encoding peptides, and/or small interfering RNAs, examples of which are provided herein and are also well known in the art.

In another embodiment of the invention, the construction of vectors suitable for gene replacement therapy or similar processes are herein described wherein suitable promoters are combined with sequences derived from HERV-BZU and therapeutic inserts, examples of which are provided herein and are also well known in the art. As will be appreciated by one of skill in the art, these therapeutic inserts may include genetic sequences which correct genetic defects, act as antigens, act as protectants or induce apoptosis, as discussed herein. As well, the unmodified HERV-BZU vector may be naturally oncolytic in analogy to foamy virus vectors (Heinkelein et al., 2005) and thus may be useful for cancer prevention and therapy in its natural or native state.

There are 5 basic applications of gene therapy vectors (Cannon & Anderson, 2004), 1) gene replacement (ADA deficiency, cystic fibrosis), 2) suicide or toxin modifying genes for gene therapy in cancer or in autoimmune conditions (Heppner et al, 2005, 3) Protective genes to render cells resistant to viral attack (siRNAs, intracellular antibodies, antisense nucleotides), 4) immune stimulation (eg. Tumor antigens or viral or microbe antigens for vaccines or adding cytokines to promote immunity), 5) cell marking for autologous bone marrow transplantation (eg neomycin). Foamy virus vectors have been used to transduce siRNAs that target lentivirus "rev" (Park et al, 2005), although there are many other ways to stop HIV replication from within the cell such as suicide genes, dominant negative viral proteins, intracellular antibodies, intrakines, interfering peptides or proteins (Wolkowicz & Nolan, 2005). Collectively these gene therapy protocols are referred to as "intracellular immunization", because they like vaccines, control the replication of viruses but operate inside the cell. As mentioned above, there is a growing interest in generating or using naturally oncolytic viral vectors (Heinkelein et al, 2005, Everts & van der Poel, 2005) although most investigators feel cancer therapies will undoubtedly require replication competent vectors (Solly et al, 2003). Somewhat surprisingly Heinkelein et al, 2005 although succeeded in eliminating a growing tumor in a SCID mouse model, with modified or not modified foamy virus vector, recommended not proceeding with the use of replication-competent "primate" foamy virus vectors in humans. Two important arguments were made. One is the issue of spread to all tissues examined (although efforts were not made to determine if this was due to blood contamination or not). However, integration and expression are not the same and his work only looked at integration. So far integrated FV sequences have not been linked to disease causation, nor have expressed virions as occurs in the salivary glands. The second issue is that of starting the next AIDs epidemic if human exogenous viruses recombined with the primate Prototypic Foamy Virus. Again, as alluded to above, such a problem has not been observed between orthoviridae and spumaviridae, as they do not pseudotype each other nor package each others sequences. Furthermore, if HERV-BZU has remained active for the past 5 million years or so, and has not yet started an AIDS epidemic, then this might be taken as evidence against the likelihood of this happening in the future. One may easily appreciate the risks of using replication-competent HERV-BZU as a vector would not be significantly different from its replication that naturally occurs in humans (see below), for which we have shown may occur with various bloodborne infections or other diseases (see below).

In other embodiments, the detection of HERV-BZU in blood (or other bodily fluids) is used as a means to screen individuals for a concomitant viremia. For example, presence of HERV-BZU may be used for: confirming a viral associated disease in an individual such as chronic fatigue or Multiple Sclerosis; for detecting the exposure to a novel or unknown infectious agent such as during a new epidemic; for the screening of blood donors to eliminate those harboring an unknown or known but not tested viremia or potentially incubating a prion disease or Transmissible Spongiform Encephalopathies (TSEs); for xenotransplantation, to monitor xenograft recipients for infectious episodes and the emergence of a novel xenozoonotic agent; during and after transplantation and transfusion, to monitor for the inadvertent transmission of infectious agents; and for determining if a therapy (such as antiviral drugs or cancer therapy) is clearing the causative agent of disease (such as a virus or tumor). In vitro, one could also induce HERV-BZU particle production in cultured CB or PBMC and screen for agents able to enhance or inhibit its activity as a means to identify new agents for therapies. In some embodiments, one may wish to inhibit HERV-K activity (perhaps chronic fatigue and multiple sclerosis) whereas for tumors and viremias it may be important to enhance its activities.

Thus, in these embodiments, detection of activated HERV-BZU within a sample, that is, the activation of HERV-BZU in vivo, can be used as a marker for the potential presence of a number of diseases or disorders, examples of which are given above. Detection of HERV-BZU may be carried out by a number of ways, for example, transcription may be detected using primers or probes based upon the HERV-BZU sequence; translation of HERV-BZU elements may be detected using antibodies or other ligands that bind specifically to HERV-BZU peptides or regions thereof.

The reason why certain HERV-K (HML-2) provirus sequences show constitutive expression in many tissues (Seifarth et al, 2005, Stauffer et al, 2004) while Type I generally do not (Armbruester et al, 2002, Wang-Johanning et al, 2001, 2003) in part may relate to their integration site(s) in the human genome. However, in general the expression of HERVs is repressed and the mechanisms for this have not been fully elucidated. However various exogenous factors can activate HERVs and include UV, chemicals, other viruses especially retroviruses but also herpes viruses, hormones, and cytokines (Muster et al, 2003). It is well known that various elements become active when the cells become stressed or are placed under adverse conditions and HERVs are just one of these many retroelements. For example the HERV-K LTR contains a glucocorticoid response element (GRE), allowing for induction in response to the stress hormone, glucocorticosteroid. As this GRE is also used by the progesterone receptor, it is not surprising HERV-K induction has been shown following estrogen and then progesterone treatment (Etkind et al, 1997). Others have identified particular viral proteins which directly transactivate HERV-K such as the EBV LMP-2A or alpha interferons (Sutkowski et al, 2004). In our experience, some T cell activators such as PHA with IL-2 appear to block HERV-BZU activation, and Tuftsin, a small peptide cytokine with effects on monocytes, can enhance or inhibit HERV-BZU activation depending on its concentration (see Table 7).

In other embodiments, HERV-BZU is cultured in vitro from human lymphocytes to, for example, generate HERV-K102 particles. The autologous blood could be used to generate the patient's own HERV-K102 particles within PBMC which are then transferred bulk into the patient (autologous blood donation) before the cells have a chance to apoptose on Day 7. Subsequently, the cells apoptose in vivo and HERV-K102 particles are released in the blood. This thereby increases the circulating levels of HERV-K particles or HERV-like particles for potential therapeutic or prophylactic benefit such as against a virus, tumor, or some other chronic condition.

HERV-BZU particles would be able to lytically infect virally or tumor transformed cells. This would eliminate these cells, and thereby would control the spread of the tumor or virus. However for the latter if it is cancer (ie. A malignant tumor), in order to get lysis, the apoptosis resistance of the tumor would have to be extinguished such as with agents able to convert malignant tumors to benign. Genistein, a natural product of soy beans, is a tyrosine kinase inhibitor, has effects similar to antiestrogens, appears to block carcinogenesis (like tamoxifen, also an estrogen antagonist), and also may convert malignant tumors to benign. That antiestrogens can significantly prolong survival irrespective of tumor type has been shown in a large randomized clinical trial (Fisher B et al, JNCI, September 1998), suggesting anti-estrogens may convert malignant tumors to benign.

In other embodiments, HERV-BZU is isolated from plasma, cultured cells or saliva, as discussed above, for example, for isolating and generating a gene therapy vector.

The following is a list of attributes of primate foamy viruses, some rendering foamy viruses more suitable as vectors for gene therapies than other retroviruses or viruses (Linial M L, 1999, J. Virol. 73: 1747-1755; Linial M L. Foamy virus replication: implications for interaction with other retroviruses and host cellular sequences. In: Brown F, Lewis A M, Peden K, Krause P (eds), Evolving Scientific and Regulatory Perspectives on Cell Substrates for Vaccine Development, Dev. Biol. Basel, Karger 2001, Vol 106, pp 231-236).

As discussed in Park et al., 2005, Virology (in press), the major problem in gene therapy is the low transduction efficiency in target tissues. FV offer the following advantages: can be propagated efficiently in various cell types of several species; isolates easily cross species barriers and virus can be recovered from many organs; no disease found in naturally infected or experimentally infected animals; humans are not natural hosts for foamy viruses; Humans infected with FV do not show any disease even after many years and no secondary human to human transmission reported; reverse transcription occurs late in cycle and at least 20% of released virions contain fully reverse transcribed infectious DNA—may be an advantage as barrier for other vectors is at the point of reverse transcription; high transduction in non-dividing cells, and transduced CD34+human hematopoietic cells express the vector-encoded transgene in all hematopoietic cell lineages analysed (range is 64 to 92%) under the control of murine stem cell virus promoter; studied short hairpin siRNAs that target the SIV rev gene (3 different sequences); and lentivirus Retroviral vectors are a public concern, 2/11 children developed leukemia.

1. Vacuolation or cytopathic (lytic) effects in certain cells in vitro but not found in vivo, which is consistent with lack of pathogenicity. This may relate to lysis of tumor or virally transformed cells.
2. Budding of infectious particles into endoplasmic reticulum vesicles rather than from cell surface.
3. Envelope contains endoplasmic reticulum sorting signal (ERS) and most infectious particles are not released by cell surface budding.
4. Most infectious particles are cell associated which can be released by multiple rounds of freeze-thawing or by apoptosis.
5. Highly cytopathic in many types of cells in tissue culture, leading to rapid vacuolization of cells and cell death.
6. Human diploid fibroblast cells and baby hamster kidney cells can be particularly sensitive to FV-induced cytopathic effects.
7. Persistent infection occurs in human hematopoietic cells where fairly high titers of replication-competent virus are made. This reflects in part that multiple insertions into the genome (multiple integrations) are made and this can then allow for high expression (also replication). This is important in terms of i) making the vector for therapy, ii) efficacy of vector expression, and iii) that the cells are presumably not killed when vector is expressed in these type of cells. Also this is very relevant for the transfection of bone marrow cells, a "stem cell" commonly used for gene therapy purposes.
8. Infective genomes are DNA and not RNA. This is significant because it denotes a probable foamy virus rather than a regular retrovirus. Furthermore, integration occurs in non-dividing cells as well as dividing as the reverse transcription has already taken place. Also, entry into cells is less likely to initiate RNA antiviral responses.
9. There are two promoters: one in the LTR and one is internal. There are temporal activities of these promoters whereby the internal promoter leads to synthesis of Tas, and Tas then can activate the LTR promoter.
10. FV-infected cells have high levels of unintegrated DNA likely to be found in particles (hundreds to thousands of copy numbers). This is useful for making the gene therapy vector.
11. Persistently infected cells contain large amounts of integrated DNA.
12. Cleavage of gag does not lead to separate matrix, capsid and nucleocapsid proteins, consequently infectious foamy viruses have an immature phenotype (referred to as infectious particles rather than virions).
13. The nucleocapsid region (which usually protects retroviral genomes from degradation by histone like binding proteins and preferentially binds RNA for most retroviruses) has affinity for DNA and to a lesser extent RNA.
14. A feature of FV is that Gag localizes to the nucleus of the cell.
15. Viral budding requires Gag and Env (whereas most retroviruses only require gag). This may in part be why other retroviruses cannot pseudotype foamy viruses making them less likely targets for recombination by exogenous retroviruses.
16. Viral life cycle is a unique hybrid between complex RNA retroviruses and DNA retroviruses (Hepatitis B Virus) but where integration is an obligate event in the life cycle. This opposing life cycle probably also impedes recombination leading to a functioning new hybrid retrovirus.
17. No evidence that FV's are pathogenic in either naturally or accidentally infected hosts which is why there is interest of foamy-type viruses as a vector for gene therapy.
18. Based on polymerase sequences, SFV-cpz (hu) is closely related to HERV-L, but not to HERV-K. However, SFV-cpz (hu) uses a Lysine (K) tRNA primer (like HERV-K) for reverse transcription. Indeed, Type I HERV-K's have 19 of 23 distinguishing or hallmark features of foamy viruses, where 4/23 have not yet been tested or reported on (see Table 9).
19. Foamy viruses have a very broad host range. All vertebrate cells tested, including all tested human cell types are infectable.
20. Natural infection is believed to be via saliva and/or biting.
21. The integration process of foamy viruses are uniquely asymmetric and result in a "TGTG" at the 5' end of the provirus. HERV-K (HML-2) also contains this sequence but not any of the other HERVs except HERV-L, but which are incomplete and non-functional. The integration sites of foamy viruses are less likely to result in insertional mutagenesis than other retroviruses (Jaretzek et al, 2004). As well their preference has been mapped to CpG islands which does not include normal cellular genes (Trobridge et al, 2006), thus making foamy retroviruses the lowest risk in terms of its integration sites.

As will be appreciated by one of skill in the art, it can be difficult to comprehend that a virus which kills the cells in which it replicates in vitro does not have pathogenicity in vivo. However, this paradox has been partially resolved recently by the demonstration in vivo that foamy viruses are naturally oncolytic (Heinkelein et al., 2005). Thus the observed lytic activity for some but not all fibroblasts by foamy retroviruses may pertain to the adventitious contamination of the fibroblast cell line by viruses, and/or tumor transformation associated with prolonged cell culture. While not wishing to be bound to a particular theory or hypothesis, for HERV-BZU this could be one way by which it is able to curtail the replication/invasiveness of incoming exogenous viruses (i.e. lytic infections). As well any cell producing HERV-BZU particles would eventually undergo apoptosis (cell death) due to the high levels of vacuolation and that HERV-BZU does not bud through the cell surface membrane and requires apoptosis for viral particle release. Thus HERV-BZU kills the cell making the virus. On the other hand, it is believed that if HERV-BZU was injected by a transfusion to a human, that this would be taken up by host cells both replicating and non-replicating cells. In some of these host cells integration may be blocked such as in non-replicating or non-transformed cells. For example we have detected dUTP containing genomes which may in some cells, get degraded upon entry to the nucleus (normal quiescent/inactive) cells. In transformed cells (or possibly active cells) it is possible the DNA repair enzymes might be active and correct the sequence allowing integration and subsequently expression and further activity. On the other hand it is possible, in normal but active cells, expression would be repressed and HERV-BZU would enter a latent state, due to these naturally occurring repressors. Foamy viruses are known to be integrated but non-active for the most part in humans infected with primate foamy viruses.

One way to circumvent at least one of the problems which has emerged during gene therapy clinical trials, namely the immunogenicity issue, is to use vectors which are based on infectious proviruses endogenous to humans, and which are expressed in the neonate and the adult, such as the HERV-K102-like HERV-BZU provirus described here. Accordingly, humans would be expected to be immunologically tolerant of the proteins encoded by HERV-BZU. This means the risk of an immunological reaction would be far less than current vectors, due to natural T-cell tolerance of the host to the vector. Note that the temporal presence of antibodies when HERV-BZU becomes activated probably reflects a T cell independent B cell response. These antibodies are unlikely to signify a loss of tolerance, in part because Env probably does not ever get expressed at the cell surface. However, antibodies to Env might help clear particles from the circulation upon their release as the Env is expressed on the outside of the particles (spikes). This may be a natural mechanism for the control of HERV-K particle production in vivo.

Another added advantage of HERV-K102 based vectors involves the issue of lack of pathogenicity in the natural host. These HERVs even if expressed (or in the case of infectious HERV, viremic in the natural host), would not generally be expected to be associated with disease due to co-evolution and selection for non-pathogenicity in humans over the 5 million or so years that HERV-K102 has been with humans (Belshaw et al, 2004 and 2005). In this regard it is interesting that 12 members of the HERV-K (HML-2) family (Belshaw et al., 2004) unlike other HERVs appears to have emerged more recently after the split of old world monkeys from new world monkeys. Indeed, in our model due to the known interference of HERV-K protease with HIV infectivity (Padow et al, 2000) we suggest HERV-K activation may be a newly discovered host protection mechanism against HIV (see Model in FIG. 16.). If it is also naturally oncolytic as expected based on all the other properties it has of foamy viruses, HERV-K may be a natural host protection mechanism against some of the pathology already seen in clinical trials with other retroviral vectors (retroviral recombination and cancer induction). As an example of co-evolution, think of HIV which naturally occurs in chimpanzees and causes no harm despite viremia (detectable levels of infective virus in the blood). One of the cross-species transfer to humans has led to the current AIDS pandemic. Interestingly, HERV-K's align phylogenetically away from all other HERVs but with HIV and to a lesser extent (based on pol) to HTLV (Benit et al., 2001). However, these HERV-Ks have little contiguous nucleotide sequence homology to HIV except a single 18 nucleotide sequence in Gag.

Initially the vector would be dormant once integrated. When a herpes or retrovirus enters the cell, this would trans-activate the vector to express the antiviral gene or gene product. Anti-viral mechanisms would ensue, diminishing the levels of invading virus produced. In doing so, this would 'extinguish' the levels of invading virus, which in turn no longer can activate the integrated vector. Thus, the vector would be self-regulating and is in an off position when there is no co-infection by an exogenous or endemic virus. This possibility offers unique advantages over existing vaccines and gene therapy strategies in that it naturally becomes active but only when needed.

Similarly, in cancer cells, an environment particularly favourable to HERV-K Type I expression, the vector might be manipulated for a lytic infection and/or for the expression of apoptosis-inducing genes. As normal cells are not normally permissive for expression, this would provide a means to target gene expression specifically to tumor tissue. If the vector is purposefully made infectious by the design of the construct, local and distant infections would make it more likely to target all the tumor. To date a means to target all tumor cells has not been clinically demonstrated. However, one has to bear in mind that the use of a replication-competent vector except in the case of replication competent foamy virus (Heinkelein et al., 2005) could also lead to transmission to third parties, and should not be undertaken without the co-development of control strategies such as an inducible cis element designed into the vector which can stop the expression or replication of the vector, if needed. It should be noted that certain viruses such as reovirus naturally causes a lytic infection in transformed tissues, and is being pursued in early clinical trials for the treatment of some cancers.

Additional protective strategies are commonly employed in the construction of the vectors to ensure only one round of replication occurs. This is because to date, the vectors chosen have been derived from disease associated animal viruses and one would not want to start a new epidemic if fully functional infectious vectors were instead used. They are usually built in two or more pieces, so that the functional genes required for packaging the cDNA are provided on a separate element from those genes needed for integration into the host genome. Because these various parts are on different strands of cDNA, this only permits one round of replication and one chance for integration if derived from the "packaging cell" where both elements have been transfected. Geneticists say that the functional genes are provided in "trans" (on another genetic element) not on a contiguous genetic element or not in "cis". It is presently not clear if such safety requirements would be absolutely needed for a vector based on HERV-K, given viremia may naturally and commonly occur in normal humans and appears generally not to be pathogenic. However one cannot presently discount the notion, should the transgene in the construct be "foreign" and immunogenic in the host, and a low but persistent level of viremia occurs, there may be associated signs and symptoms of an ongoing infection or adverse events in the host. This may not be desirable or acceptable if for example, this leads to chronic fatigue, or through a chronic wounding model of carcinogenesis, leads to cancer. However, for the latter, if HERV-K102 is naturally oncolytic, this would be less of a problem.

For example, one skilled in the art, such as discussed by Mergia and Heinkelein, 2003: could produce a foamy virus like vector using HERV-BZU. For replication competent foamy virus vectors only Bet is removed and a small marker gene inserted. For replication incompetent vectors the gag, pol and env proteins are provided in trans in the packaging cells while the viral genome containing plasmid is produced in other cells or microbes. When vectors are made independent of Tas, often the exogenous CMV promoter is used.

Summary of Advantages of New Vector

In summary the following is a list of distinct potential advantages of a vector based on an infectious HERV-K102 or K102-like provirus over those currently available or in clinical use (listed in no particular order of significance). These advantages relate to the novel finding that HERV-K102 unlike any other HERV described before, 1) has the hallmark features of a foamy virus and as well 2) appears to be induced in humans as a host protection mechanism against viral and tumor transformation. Furthermore, unlike foamy viruses of other species, HERV-K102 is specific to humans, and humans are tolerant to this or a very closely related provirus as it is expressed in the placenta, and can be recovered from CB plasma. Finally, this provirus naturally replicates in humans and as such (based on 5 million years of co-existance) is highly unlikely to result (at least in most cases) in significant pathology due to the use of a replication-competent vector. (ie. The risk of using this as a replication competent vector is no higher than what naturally occurs.)

1. Efficiencies in both replicating and non-replicating cells because functionally it appears to resemble foamy viruses (i.e. vacuolating retrovirus with DNA genomes). HERV-L is the most homologous to known foamy viruses but these genomes are incomplete. Genetically there is very little homology to prototypic foamy virus (PFV), except that it is a retrovirus and therefore functionally seems to resemble foamy viruses. Note that since infection and lysis occurred in almost all MRC-5 cells (i.e. 100% by 24 hours) and perhaps only 5 to 10% of these cells would be in S phase, this provides evidence that infection and expression does not depend on DNA replication which is consistent with the properties of a foamy virus.

2. May be particularly suitable for transfection of non-replicating stem cells. Foamy viruses can integrate into non-dividing cells and thus replication can be independent of phase of the cell. This is very important for transfections of stem cells, the most logical target for gene therapy.

3. Anticipated higher ability to infect a wider range of cell types in analogy to foamy viruses.

4. Anticipated ability to reach most tissues in the body, for example brain and the CNS, gonads, bone marrow and other immunologically privileged sites.

5. Evidence suggests high efficiency of transfection approaching 100% in vitro within 24 hours. Most other vectors only transfect a few percentage of the target population and often after considerable time (21 to 60 days). This enables quick transfections of autologous cells for almost same day treatment of patients.

6. A means to target genes directly to tumor tissues or infected cells as further replication and activity is anticipated only in these cells.

7. Due to the known preferential expression of the provirus in cancer cells (as normal cells may naturally limit activities of the vector), this provides a natural type of cellular targeting of activities to abnormal cells (either virally transformed or tumor tissue) without the need for additional proteins which might prove to be immunogenic in humans. Thus, exploiting these natural mechanisms may be a safer vector with the possibility of significantly less immunogenicity and longer continued or repeated use. Suitable inserted factors for cancer therapy include but are by no means limited to antisense or interfering factors as against such proteins as alpha-fetoprotein and any other protein commonly involved in apoptosis resistance of cancer cells.

8. The vector could be manipulated to go to early lytic infection (for example to kill cancer cells), integration mode (for viral silencing), replication mode, or inducible promoter mode depending on the desired outcome. For example, it may be possible to target to specific cell types by enclosure in liposomes (with antibodies for targeting).

9. There are probably decreased risks of immunologic clearance as humans would be immunologically tolerant (T cell tolerance). For example while antibodies are made when HERV-K is active, they also quickly disappear (over the course of several months, Boller et al, 1997, Kleinman et al, 2004). In contrast, antibodies to foreign entities can remain very high over many decades and will exhibit an amnestic response. The antibody response (which seems to be primarily low avidity antibodies) would also serve to control infectivity of HERV-K and to downmodulate it s activity which would be a safety feature This lack of high avidity high levels of antibody would improve efficiency in vivo when compared with foreign vectors.

10. Much better safety profile due to T cell tolerance. Thus the risk of inflammatory adverse events are greatly diminished. Specifically, vectors which are immunogenic may have such a short half-life that they are ineffective or could alternatively cause adverse events like anaphylactic shock leading to death.

11. Vectors based on infectious HERVs are expected to be inherently non-pathogenic for humans when compared to foreign vectors or vectors based on viruses which have already been linked to diseases. HERV-BZU like FVs lacks the CS17 immunosuppressive domain in the TM of Env. Thus, it is not immunosuppressive like other retroviral vectors.

12. Vaccines delivered by a HERV-K102 vector may naturally or preferentially replicate in monocytes, dendritic cells and other non-replicating antigen presentation cells improving efficacy of immunization.

13. Immunization in situ would probably produce both cellular and humoral immunity which generally is more desirable than just humoral which tends to be the focus of traditional vaccines. An antiviral response is both antibody (clears and inactivates free particles) and $T_{CTL}$ (kills cells producing virus).

14. One might expect far less problems with insertional mutation or activation of oncogenes with vectors based on HERV-K probably since the provirus is probably naturally down-regulated for the most part, in normal cells in the immunocompetent adult and because due to its similarity with FV, it would be less likely to integrate into active sites, or to cause insertional mutations.

15. With less inflammatory reactions (by the immune system) there may be less chance for an accidental creation of mutations in transfected tissues. Attacking immune cells produce reactive oxygen species which causes genetic mutations and which is known to lead to cancer over time (through the chronic wounding model of carcinogenesis).

16. For therapies requiring active, repetitive therapy and not just single administrations such as for vaccines, it would be straightforward to overcome any natural down-regulation in humans by the co-transfection of an inducible promoter if needed or desired.

This invention also covers the detection of the natural expression of the provirus or particle which can be associated with underlying diseases inclusive of tumors (malignant or benign), with infectious agents (particularly exogenous retroviruses and herpes viruses), and in some instances may relate to vacuolation seen in situ associated with a number of neurodegenerative diseases. This detection may assist with the diagnosis and prognosis of diseases. It may also help in the selection of suitable treatments of underlying diseases although the HERV-K102 provirus itself may not be the causative agents of such diseases. For example, you could monitor the patient for HERV-BZU levels even when you do not know what exogenous virus is causing the disease and then try various agents in vivo (such as natural products) and see which ones shut down HERV-BZU. Note this assumes you first test the agent against HERV-K102 in vitro to ensure it is not itself affected by the drug. You could then wait for resolution of the pathology with continued agent administration.

In our efforts to identify potential xenozoonotic infectious agents relevant to clinical xenotransplantation, we employed human cord blood as bloodborne indicator cells for co-cultures with pig spleen cells. We were quite surprised to observe a distinctive cytopathic effect consisting of vacuolation and particle formation in cells not co-cultured with pig cells (see FIG. 1). Vacuolation was not found in freshly isolated cord blood cells nor in peripheral blood mononuclear cells (PBMC), FIG. 2 but developed by day 3 in a few cells and appeared to spread to other cells such as by day 5 about 80% of the cells seemed vacuolated. This process occurred in both single donor CB cells where cells do not proliferate and in mixed lymphocyte cultures where T cells become induce to proliferate and enter S phase on day 3. Thus, activation and induction of the foamy virus can occur associated with quiescent cells and in proliferating cells. By day 7 it seemed the cells were beginning to die in culture and this progressed during culture out to day 12. It is notable that activation schemes used for the culture of retroviruses or for herpes viruses abolished vacuolation (FIG. 1) when not co-cultured with pig cells. These employed PHA and IL-2 which are known activators of T cells. The vacuolation was not related to the serum used in the culture media (FIG. 2) and we could rule out other non-specific toxic mechanisms such as toxicity or inherited lipid storage diseases. By EM we noted the extensive vacuolation (FIG. 3), and by higher power found uniform immature particles budded into the endoplasmic reticulum (FIG. 4). We searched for evidence of cell surface budding but found none. The particles were about 100 nm (typical of a retrovirus) and had translucent cores. Translucent cores are what gives it its immature particle phenotype, and is due to a lack of processing of Gag. This feature is typical of foamy retroviruses and some HERV-K associated particles in teratocarcinoma cell lines (Bieda et al, 2001). These results strongly suggested to us that an endogenous human retrovirus with foamy-like qualities and sequences similar to HERV-K might be implicated. We developed novel PCR polymerase primer sets to HERV-k pol (FIG. 5) and tested for induction of Type I HERV-K (HML-2) pol (FIG. 6). We found the levels of mRNA correlated with particle formation and vacuolation such as they were not apparent at the start of culture, increased, peaked on day 5 and on day 7 (associated with apoptosis) started to diminish. Sequencing of the cDNA PCR products from Cord Blood (FIG. 7), has identified Human Endogenous Retrovirus K102 (HERV-K102) pol sequences (AF164610). However, there may be 3 morphologically distinguishable types of particles (Bieda et al., 2001) and ours may resemble the classical ones which are associated with very minimal Gag processing.

3 Types of particles observed in teratocarcinoma cell lines
  a. Classical HTDV immature particles without spikes (no cleaved gag, cleaved env.)
  b. Immature particles with prominent spikes in 2102 Ep (cleaved gag, 30 kD but Env not cleaved)
  c. Mature particles without spikes (cleaved gag 30 kD, no envelope)

The expression of HERV-K102 in health and in disease is complicated by virtue of the fact that primers used in PCR may detect HERV-K (HML-2) Type I or Type II or both, but very limited information exists about HERV-K102 specific expression. Type I HERV-K can express an alternatively spliced product called np9 whereas Type II expresses instead, cORF (12). Recent studies have shown np9 is expressed more frequently than cORF in human cancer cell lines and tumor tissue, but is not found in normal tissues including freshly isolated lymphocytes and fibroblasts (12). This is in keeping with our finding that HERV-K102, a Type I HERV-K, is not expressed in freshly isolated PBMC (see below for more data consistent with this such as in FIG. 9, FIG. 10, FIG. 14, Table 1, Table 3, Table 6 and Table 8). Thus, reports of HERV-K expression in freshly isolated PBMC (13, 14) most likely relates to Type II HERV-K transcripts.

Primers for Regular PCR for HERV-K102 pol

```
Forward (nt 4272-4291)
5'-TGG CAG AGC AGG ATT GTG AA-3'    (SEQ ID NO. 3)

Reverse (nt 4565-4546)
5'-CAG ATG CTA TTG CCA GTC CA-3'    (SEQ ID NO. 4)
```

Type II can be detected in freshly isolated PBMC, indicating it cannot be specifically induced by the presence of an incoming infection. Thus, detection of HERV-K Type II is not likely to offer informative data for detecting the presence of an active infection with a bloodborne viremia, for example, to be used to screen blood donors for the presence of an unknown viremia. Similarly, for gene therapy, one prefers a construct which could be specifically induced under defined conditions, not a constitutive expression. Constitutive expression may instead interfere with the process of gene therapy (directed expression).

To date the only disease association specifically involving HERV-K102 concerns the expression of envelope protein mRNA in 45% of breast cancers (15) but not in normal tissues. Of interest, Type II HERV K expression was not at all detected in these samples (15). It has been suggested that female hormones (estrogen followed by progesterone) can induce HERV-K as it has a hormone response element in its LTR (promoter/enhancer) (see Patience et al, 1996). They cloned and sequenced the envelope and found quasispecies with the same and slightly different sequence of HERV-K102. They also found np9 expression and np9 is specific to Type I HERV-K (HML-2). More generally, activation of monocytes or U937 monocytoid cells is known to increase the expression of HERV-K (16). Additionally HERV-K expression is increased in brain tissues from patients with multiple sclerosis or human immunodeficiency virus infection but not in Alzheimer's dementia (16). By serology, HERV-K expression has been linked to a number of other chronic diseases such as various forms of autoimmunity (17, 18) as well as germ cell tumors (19) although no causal connection has been established for pathogenesis. Thus, HERV-K102 expression potentially may be associated with a variety of chronic diseases in humans.

Vacuolation is a common in vitro property of foamy retroviruses (20). However, in general vacuolation, like apoptosis, is rarely observed in situ except for neurodegenerative disorders (21). Of interest, neurodegenerative diseases as studied in animal models typically involve prions or retroviruses (22), although some neurodegenerative diseases are known to be genetic. It is also known toxic substances can induce vacuolation associated with cell death, albeit this usually occurs within a matter of hours (23) and thus is unlikely to play a role in our cultures or in chronic diseases. In some clinical cases such as ovarian cancers, infective particles associated with vacuolation in vitro have also been demonstrated (24). A recent entry to GenBank (Nov. 23, 2002, AY186778 GenBank) purports to the existence of a HERV expressed in human melanoma cells which can be passaged in bovine cells (25) but seems to be primarily Type II (HERV-K108 (Muster et al., 2003).

U.S. Pat. No. 5,756,281 includes an electron micrograph showing vacuolation of a PBMC is provided which is similar to our FIG. 3. In this patent it is purported that the vacuolation of the PBMC related to a severe encephalopathy in a single patient. However, this blood sample had been stored at room temperature for 48 hours before being examined by electron microscopy, and no control blood samples similarly stored were provided or analyzed, indicating this observation cannot be interpreted. Attempts to identify a virus resulted in the provision of a small piece of sequence apparently related to human CMV herpes virus. Our HERV-BZU does not have homology to CMV.

U.S. Pat. No. 5,882,912 claims an infectious Simian Foamy Virus (SFV) was isolated from a human. Previous patents had not established any evidence for primate foamy viruses to productively infect humans, and the infectious ability is a key attribute of a vector for gene therapy. This foamy virus was derived from monkeys and thus, humans are not expected to be tolerant to its viral antigens. Thus, as argued below, the HERV-K102 provirus, which appears to share many attributes with primate foamy viruses, is a significant advance over the SFV as a vector, due to its origin within the human genome and that it naturally replicates in humans under certain conditions.

As mentioned above, we observed vacuolation in cultured single donor or mixed donor blood cells whether derived from Cord Blood (CB) or adult peripheral blood mononuclear cell (PBMC) samples. Within these vacuoles, particles about 100 nm could be visualized (FIG. 4). This could not reflect an inborn error of metabolism as it developed in all CB and PBMC tested but was not apparent in uncultured, freshly isolated cells (FIG. 2). Thus, it was not rare, and was inducible. Furthermore activation schemes involving PHA and IL-2 commonly used in clinical virology laboratories to isolate herpes and retroviruses, blocked vacuolation (FIG. 1), indicating not only was the vacuolation inducible but it was subject to regulation. (see later in Table 7 for other regulators of HERV-K102 activity in cultured cells.)

This along with the visualization of particles in the vacuoles, indicated an endogenous retrovirus with foamy-like properties was likely involved.

The vacuolation initially started in few cells and appeared to spread with time to other cells in the cultures. As this was shown for both CB and PBMC, as well as single donor (non-proliferating cells) and for mixed lymphocyte reaction (a mix of non-proliferating and proliferating), these results suggest the infectious agent can replicate in non-proliferating and proliferating cells.

Given that all cultures used fetal calf serum (FCS), we had to determine if the FCS was the source of the apparent foamy-like virus. Upon testing various sources of serum, and showing vacuolation occurred in all cultures including normal human AB serum and autologous serum, this clearly demonstrated FCS was not the source of the vacuolation (FIG. 2). This indicated to us that an endogenous human retrovirus might be involved.

As reviewed in the background, only HERV-K has been associated with particle formation so we devised a novel primer set based on the detection of polymerase (pol) to allow us to detect members of the HERV-K family. The sequence of the novel primer set is provided in FIG. 5. The size of the PCR product is 295 base pairs. We determined the sequence of the RT-PCR product amplified with the primer set (encoding mRNA induced in day 4 CB cells (single donor)) and surprisingly it gave a single clear sequence signal (FIG. 7). The sequence of the PCR product was identical to HERV-K102 (AF164610), although this sequence was still 98% related to a number of close family members, such as K101, K103, K10, and others.

By using PCR for the pol, we were able to show the induction of mRNA corresponding to the pol of HERV-K102 (FIG. 6) correlated with vacuolation which was induced by about 48 hours, peaked at about 5 days and seemed to decrease thereafter due to cell death.

We sought to provide further evidence of HERV-K102 expression and translation, and thus, potential for particle formation. In foamy viruses, the expression of the envelope is required for particle formation and for infectivity. As well, the envelope protein of retroviruses tends to contain most of the heterogeneity of retroviral sequences, moreso than gag which often shows cross-reactivity between similar types of retroviruses but for different species. Accordingly, antibodies specific to "antigenic" peptides of HERV-K102 envelope were made through a commercial company, Washington Biotechnologies, Inc. The company was given the full sequence of the envelope antigen of HERV-K102, and provided us with the most antigenic/immunogenic short peptides based on an algorithim they had developed. We then selected two peptides for further study and immunization based on their sequence specificity for Type I HERV-K (HML-2), the ML-4 peptide (SEQ ID No. 5), and HERV-K102 (ML-5 peptide (SEQ ID No. 6)) (FIG. 8). A blast of Peptide ML-4 in GenBank showed it was identical not only to HERV-K102, but also K101, K103, K10 and K, but not at all to Type II family members such as K107, K109, K113 or K115. ML-5 was found to be specific to HERV-K102 only.

Using the rabbit antisera, we looked for the induction of HERV-K102 envelope protein expression in cultured versus non-cultured, freshly isolated cells (referred to as Day 0) by immunohistology. These results are shown in FIG. 9 While no detection of HERV-K102 envelope was found on day 0 using this very sensitive method, day 7 cells in which vacuolation and HERV-K102 pol expression could also be demonstrated, had clearly detectable expression when compared to the pre-immunization sera of the rabbits. The images in FIG. 9 clearly show cytoplasmic staining, we could not differentiate whether some Env is available at the cell surface (no membrane accentuation noted, FIG. 9). Our results might suggest Env even when expressed does not localize to the cell surface at least on normal cells. So antibodies to Env probably do not react with normal cells in vivo. However, we do not know if the Env can become cell surface expressed in pathological conditions, such as with HIV infection. If so, these antibodies may also lead to killing and clearing of HIV infected cells.

This possible lack of Env cell surface expression may have consequences; more than one particle may enter the cells as not subject to receptor interference, which may help explain the known multiple integrations of foamy viruses.

The finding of the expression of envelope protein corresponding to HERV-K102 strongly suggested the likelihood that the particles seen by electron microscopy and which formed in the vesicles, might be infectious, since for foamy viruses, the envelope is an absolute requirement for particle formation and infectivity. By immunoprecipitation followed by Western blotting with ML4 antisera we found evidence for a 90 kD and ~45 kD proteins (FIG. 10). We speculate the 90 kD is the precursor while the 45 kD is probably the cleaved surface fragment which still contains ML4 (SEQ ID No. 5) and ML5 (SEQ ID No. 6) peptides. The cleavage suggested that these particles may be infective. Also the fact that they resolved in SDS-PAGE without reducing agents indicates like PFV Env, the surface unit probably lacks the C-X-X-C domain of most other retroviruses and does not require reduction by 2-ME or DTT which is usually needed in order for the cleaved precursor to fall apart and be resolved by SDS-PAGE.

So we tested infectivity of frozen-thawed CB cell lysates, where single verses mixed lymphocyte combination donors had been cultured and compared this to media controls and to freshly isolated and non-cultured (Day 0) cells. For these experiments we tested 3 fibroblast cell lines. These results are shown in FIGS. 11 and 12. Since we expected the infectivity to be analogous to foamy viruses, we froze-thaw the cells, and then placed the cellular material onto indicator cells overnight. Samples were tested in duplicate for both single and mixed donors. At 16 hours we washed away non-adherent materials from the adherent monolayer fibroblast cells. In none of the cases did we notice any cytopathic effects at 16 hours. We then incubated the cells an additional 8 hours, and then observed the monolayers. For MRC-5 cells, virtually all the cells had apoptosed and detached from the monolayers at 24 hours, when day 4 induced CB cells (frozen-thawed) had been laid on top (FIG. 11). In contrast, media and day 0 did not show this obvious and pronounced cytopathic effect. No alterations in the HFL-1 cells were observed. In the Vero cells which are African green monkey cells, it appeared that there may have been some granulation but no other obvious cytopathic effect occurred. Thus, the controls indicated the cytopathic effects were not due to some nonspecific toxic effect. This was also suggested by the absence of cytopathic effects at 16 hours. We concluded that the particles seen by EM associated with vacuolation were indeed infective.

By using RT-PCR for HERV-K102 pol mRNA in the indicator (fibroblast) cells we were able to confirm expression in the day 4 MRC-5 cells and in VERO cells and not in the HFL-1 cells (FIG. 12). As expected media and day 0 controls were negative (FIG. 12).

We then used the QIAamp Ultra-Sensitive Kits to isolate DNA or RNA containing "particles" or nucleotides from 1 ml of plasma. For a control for genomic contamination we used β-actin. We looked for DNA and mRNA (since for foamy retroviruses, the infective genome is DNA [15]). Our B actin PCR is more sensitive than our HERV-BZU pol (FIG. 13), which provides us with some assurance that when HERV-BZU is detected it is not due to genomic contamination The results on plasma are shown in FIG. 14. While no sequences were found in 30 of 30 normal healthy control samples, we observed HERV-K102 DNA pol sequences in 2 of 4 CB plasma samples (lanes 6 and 7). We also observed DNA only in a chronic fatigue patient (lane 2). In a bad case of EBV viremia (lane 3) we observed both DNA and RNA. In an Multiple Sclerosis (MS) patient (lanes 4 and 5) we observed DNA and RNA. Lane 4 is a sample taken from this MS patient at initial diagnosis, while lane 5 is another sample taken 5 months later when she started to progress and where the HERV-K102 pol levels seemed to increase. When this patient went into remission when placed on interferon therapy we could no longer detect HERV-K102 sequences in her plasma. In lane 1 is a normal plasma (1 ml) spiked with 100,000 PBMC (uncultured), showing the detection of the control PCR, β-actin. We had to confirm that the control would be positive if sufficient cells contaminated the specimens so that we could interpret the DNA results. We found the regular PCR, a less sensitive method, did not amplify genomic DNA due to its sensitivity and did not amplify mRNA as this is not isolated with the special virus isolation kit we employed. Overall, these results show putative particles are not found in the plasma of normal healthy adult s but can be detected in disease states. Furthermore they show DNA+/−RNA sequences in particles corresponding to HERV-K102, as would be expected for a foamy type retrovirus but not for other types of retroviruses.

In order to obtain further substantiation of HERV-K102 activity we used new primer sets and probe which we designed as given in FIG. 15 and used this to look for the presence of HERV-K102 cDNA in cultured lymphocytes (Table 1). The principle of real time PCR is such that the probe is labelled with a non-fluorescent quenched molecule which becomes released and fluorescent when the polymerase attempts to elongate the sequence to which it binds. This activity is due to endonuclease activity of polymerase. The released signal is thus proportional to the amount of template present in a given same. Another advantage of this method is that it has a built in way to confirm the correct sequence is being amplified (ie the probe) and sequencing is not needed to confirm the results. The best advantage of the real time PCR assay is that it is ultra sensitive and due to an internal label in the buffer for standardization, it is able to reliably detect molecules to the 0.1 picomolar range. At the same time in the same assay due to its inherent design, real time PCR has an incredible range ($10^9$) so that on the same plate 0.1 picomolar grams of material can be detected as well as milligrams.

First we wished to show in normal lymphocytes that there are increased levels of HERV-K102 pol DNA over and above genomic when HERV-K102 associated particles are made. For this we extracted DNA and then performed the HERV-K102 ddCt ratio. Please see FIG. 15 for the sequences and location of the forward and reverse primers and the probe used for the real time PCR. Please note FIG. 15 also demonstrates these primers and probe would not amplify HIV sequences. We developed a ddCt ratio real time PCR method (relative quantitation) which takes the difference between HERV-K102 pol and 18 s RNA Ct's (delta Ct), and subtracts this from the same performed on commercial normal adult genomic DNA (male) (the delta delta Ct). Then we use the algorithm 2−(ddCt) to calculate the relative ratio of HERV-K102 to genomic DNA. This index when elevated above normal ratios (see Table 3 for these ratios) for fluids with contaminating cells (eg plasma and saliva) indicates an excess of non-genomic DNA templates and could be taken as a surrogate marker for putative particles in the sample. This method would not be suitable however, for directly testing cancer samples, as it would not be interpretable due to gene amplification and aneuploidy. Since real time PCR is so sensitive, and we were only interested in the DNA copy number of HERV-K102 pol, we subsequently used the Qiagen DNA Mini kit for DNA extractions of plasma. We found this kit reliably isolated approximately equivalent amounts of cells from each sample or sample type tested and was simpler to use than the Qiagen Ultrasensitive Virus (DNA & RNA) kit.

As shown in Table 1 no excess DNA above normal genomic levels of HERV-K102 pol could be detected in uncultured cells. The value of 0.74 ratio falls within the normal range which we established on 24 samples to be 0.88+/− 0.39, RANGE 0.41 to 1.42 (see Table 3). On day 4 there are detectable excesses of HERV-K102 pol DNA as shown by the ratio 3.68 which cannot be due to cellular reproduction of its DNA as the CB cells under these conditions (single donor) do not proliferate. By day 7 however when cells apoptose due to excessive vacuolation and particle production, cells overproducing the particles die, and release their particles to the supernatant. Since we only extract cells, on day 7 we found the ratio dropped consistent with the loss of particles. Thus, a value above 1.42 is considered to be outside of the normal range.

We devised a means to prove that the excess DNA was due to production of HERV-K102 pol containing cDNA within particles. Commercially available master mix buffer can be purchased with or without Amperase-UNG a highly purified enzyme Uracil-N-Glycosylase, which when included in the buffer for the real time PCR will digest any DNA or cDNA templates containing uracil. Genomic human DNA does not contain UTP instead of TTP as it has many repair mechanisms (see Priet et al, 2005 for full discussion). Thus, if any isolated DNA becomes digested it must be non-genomic. As well the reverse transcription enzyme of retroviruses does not distinguish dUTP from dTTP, so if replication occurs in non-proliferating cells like monocytes, the excess levels of dUTP to dTTP will ensure some dUTP is incorporated. As shown in Table 1 a significant proportion of the excess DNA contains UTP as shown by the digestion of 52% of the Day 4 sample by UNG in the master mix buffer. This finding suggests the initial cell which produces HERV-K102 particles are probably monocytes, a fact confirmed also in Table 1 as monocyte-depleted lymphocytes do not activate their HERV-K102 and no excess HERV-K102 DNA is detected over the 7 days of culture. With time however, and particularly as evident on day 7 when about 30% of the cells, the highly vacuolated cells die, far less of the cDNA contains dUTP as shown by the fact only 15% can now be digested with UNG. These results are consistent with our observations on the cultures where initially few cells make vacuoles, and over time by day 3 to 4, many cells are starting to produce vacuoles. As 80% of the cultures are T cells, this means either induction or spreading of the provirus is also occurring within or to T cells.

We next decided to study what happens in disease states, such as multiple sclerosis (MS). As shown in Table 2, by using a quantitative method for detection of HERV-K102 (the same method as the ddCt but here we run standard curves to actually quantitate the levels rather than internally standardize to a single point reference), and comparing it to levels of DNA encoding 18 sRNA as a control for genomic equivalents. First, we found elevated levels of HERV-K102 DNA in uncultured PBMC from MS (see Table 2, compare 0.71 for the control and 2.53 for MS Day 0 where the range for normals is 0.41 to 1.42 as shown in Table 3). This ratio further increased when the MS patient's PBMCs were cultured in IMDM, to 3.78. However at day 7 when the vacuolated cells apoptosed (about 33%), the relative levels dropped to about ⅔s of the levels at culture initiation (to 1.67). These results provide strong evidence for HERV-K102 activity both in vivo and in vitro on the same patient by simply measuring relative DNA excess which probably represents cDNA found in particles (see above and below). That the particles contain cDNA is expected for a foamy-like retrovirus.

Using the ddCt relative quantitation method we tested plasma samples from different groups for evidence of HERV-K102 dDNA or excesses above expected genomic levels. These results are provided in Table 3. We were able to evaluate that normal human DNA as extracted from plasma, PBMC or saliva has a relative ratio of HERV-K102 DNA to "18s RNA" DNA of about 0.88+/−0.39 (n=24). In CB plasma samples (2/4), these values are mildly elevated (2.22; 2.04 or 2.39). In MS samples (n=11), we found 73% of the samples had activated HERV-K102 (presumptive particles) where the levels were slightly higher than that found in cord blood plasma (3.19+/−1.71) In contrast in HIV viremias, 81% of the samples appear to be grossly elevated (14.88+/−32.27 with a range of 1.45 to 152.22, N=32). We had the HIV viral loads and therapy status on 22 of these samples (see Table 4). Interestingly, of the 4/22 negative samples, ¾ were found in patients on antiviral therapy and who had low viral loads (i.e. under 3000). The fourth case where HERV-K102 was negative (BZU ID #19 (0.67 ratio)), the HIV VL was moderate (27,717) but interesting had the highest CD4 level of all the HIV samples tested (1010). Thus, this sample could be considered a favourable instance of HIV viremia, perhaps relating to a less virulent strain. Alternatively, it is possible if re-extracted for RNA, this sample could have HERV-K102 pol containing particles which are exclusively RNA. In all our studies we only found one MS sample appeared to have exclusively RNA genomes.

Perhaps more striking was the apparent ability to differentiate particle associated DNA in HIV plasma from genomic based on its increased sensitivity to uracil-N-glycosylase (UNG) contained in one of the master mixes supplied by Applied Biosystems. Here 16/18 positive samples tested (see UNG digested ratios in Table 4) reverted to normal genomic levels (0.76=/−0.37,) indicating for the most part the particle associate DNA (cDNA) in HIV samples contains significant dUTP. Most probably here a primary producer of the HERV-K102 particles is a cell which has high levels of dUTP to dTTP ratios like monocytes. In 2 of the 18 samples (BZU ID #8 and #4) UNG exposure only partially digested the excess HERV-K102 suggesting HERV-K102 in these samples might be derived from both monocytes and T cells or simply that HIV is infecting at least two cell types. It is important to realize although there seems to be a correlation of HERV-K102 reactivation in HIV viremia (Table 4), this relationship is not so perfect to suspect our primers and probe mistakenly amplify HIV (Table 4). As well there is insufficient sequence homology (see FIG. 15) to enable this to happen.

We also tested other bloodborne pathogens for reactivation of HERV-K102 particles in vivo. These results are shown in Table 5. The EBV sample shown in FIG. 14 was found to be positive by the HERV-K102 ddCt method (4.56). We also found ¾ samples from HHV-7 viremic samples to be positive. In CMV we noted some individuals (2/7) had extremely high levels of HERV-K102 cDNA/particles while only 2/7 could be classified as negative. CMV is not normally a problem for normal healthy adults, but can be imminently life-threatening in transplant recipients who are purposefully immunosuppressed. Perhaps these high positives relate to the occurrence of acute rather than chronic infections. Similarly, we found one HCV sample negative and one excessively positive (Table 5). Again, without patient history and a larger study we do not know if this relates to a successful treatment of HCV in the first instance or to an acute infection in the second instance, or if for the latter it reflects the induction of liver cancer (hepatoma also known as hepatocellular carcinoma). Nevertheless the results provided in Table 5 strongly indicate HERV-K102 is also activated in other bloodborne infections, in addition to its activation in HIV and MS.

We also performed serology on the two HERV-K peptides, ML-4 specific for Type I HERV-K (HML-2) and ML-5 specific for HERV-K102. The results are shown in Table 6. Type I HERV-K reactivation or HERV-K102 reactivation is not commonly seen in normal healthy adults. The finding of 1/51 samples positive for either peptide (both were only marginally positive) may relate to the fact while these samples came from apparently normal healthy adults, one was a laboratory worker and one was a farmer, and are probably at higher risk for exposure to infectious agents and/or zoonotic agents. In MS we saw 15 of 24 samples (62.5%) positive for Type I HERV-K HML-2 sequences whereas far fewer samples (4/24 or 17%) were positive for the ML-5 peptide. These results might imply other Type I HERV-K (HML-2) family members are frequently activated in MS, more so than HERV-K102. Alternatively it may mean HERV-K102 may be more sensitive to downmodulation by the beta interferons used to treat MS patients as most of these patients were on therapy. We also observed positive serologies for both peptides frequently in HIV viremic patients (about 70 to 80%) which is substantiated by the ddCt results in Table 3 and 4 also showing 81% reactivation. The serology for herpes viremia was somewhat unusually low (17.6%) in that the ddCt ratios suggested 71 to 100% of herpes infections might be associated with HERV-K102 reactivation. However, one should remember that these are acute infections and while the induction of HERV-K102 may take a few days, it may be 2 weeks or longer before the antibodies are circulating. Alternatively, the drugs used to mitigate the herpes viremia might also immunosuppress the host.

With HIV or herpes viruses, it is expected that this positive reaction is not a cross-reaction but reflects reactivation of HERV-K102 with underlying infection. These results appear to suggest that during active acute viremias, at least temporary production of antibodies to HERV-K102 envelope antigens can be detected. However most normal individuals do not have antibodies to HERV-K102 or K102 like envelope antigens. That antibodies to HERV-K can be temporarily produced with underlying disease, has been previously demonstrated in cases of germ cell tumors, where the antibodies disappeared upon complete removal of the tumor (Boller et al, 1997). In other cases when the tumor returned, the antibodies reappeared. (Boller et al, 1997, Kleinman et al, 2004). Thus, for 67% of germ cell tumors, HERV-K antibodies can be used as a prognosticator. It may also be a prognosticator for these other diseases, infection with a bloodborne pathogen, multiple sclerosis, chronic fatigue and possibly other diseases where a viral or even environmental contaminant is involved such as in other chronic diseases.

Our work corroborates the notion that humans are generally tolerant of HERV-K102 antigens. This result was expected since Cord Blood and adult blood can naturally express HERV-K102 particles. On the other hand this work shows the potential for reactivation when there is underlying diseases.

Finally we investigated certain natural products, drugs and peptide cytokines for their ability to regulate HERV-K replication such as measured in CB cells (Table 7). These agents were tested at approximately $10^{-6}$ M or equivalent. We harvested the study on day 5. As shown in Table 7, two natural products which a chronic fatigue patient uses to enable her to reach deep restorative sleep, St. John's Wort and Oncolyn, appear to inhibit HERV-K102 replication in vitro. This patient plasma sample is positive when off these natural products for more than 3 days (see Lane 2 in FIG. 14) and by the same method her sample is negative when she takes these natural products at bed time. When off the natural products even as evident on the first day, the patient reports drowsiness and the inability to concentrate. Using the more sensitive method ddCt, we observed her ratio to be 2.00 when on the St. John's Wort and Oncolyn, representing a definite but marginal positive, but when off this regime after 3 days her HERV-K102 ddCt ratios were greatly elevated measuring $2.5 \times 10^8$. This correlation of in vitro results with clinical utility suggests this method could be used to screen for new agents which may have therapeutic benefits for a number of diseases. For one substance, Tuftsin, a 4 amino acid peptide cytokine with selective effects only on monocytes, at low levels (1/5000) it enhanced HERV-K102 replication and at high levels (1/500) it inhibited HERV-K102 replication. Tuftsin is naturally cleaved from the FC region of IgG and is considered an immunoenhancing substance and the 1/5000 concentration is usually employed to show its enhancing effects on the activation of monocytes. Many cytokines exhibit both immune inhibiting and enhancing properties depending on their concentration.

We also found the hormone like agents (E2=estradiol, DHEA=dihydroepiandrosterone, EM652 a proprietary DHEA like molecule, and tamoxifen, which is an estrogen antagonist but which also has estrogenic activity) enhanced HERV-K102 replication in the cultured CB cells. DHEA is thought to be immune enhancing and decreases in both sexes as we age, and is thought to leave us more susceptible to chronic diseases as we age. Here we are first to imply this may also concern the replicative capacity of HERV-K102. Estrogen and female sex hormones have been reported to enhance HERV-K activity, and here we show for the first time, that it may also directly enhance HERV-K102 replication. It is known for some time that several autoimmune diseases are more prevalent in females than males, and many believe it may be due to estrogen, although its direct involvement has not been shown. While we are not saying HERV-K102 activation causes disease, in autoimmune conditions, where presumably some other agent or chemical induces HERV-K102, it is possible through apoptosis or lysis (see FIG. 16 for model for HIV), that this could lead to permanent damage for example if the infected cell involves terminally differentiated cells such as neurons in MS. Loosing a few neurons would probably be inconsequential, but a massive loss of neurons could be clinically evident.

Thus, the results in Table 7 indicate testing for new pharmaceutical agents useful for a number of diseases could be based on the activity of HERV-K102. It also provides an important means to be able to screen agents able to shut down HERV-K102 replication such as might be necessary in emergency conditions when the modified vector is injected into humans.

In Table 9 we provide a summary of the similarities of the properties of HERV-K102 with the primate foamy virus now known as Prototypic Foamy Virus, but previously referred to in the literature as Human Foamy Virus. The name was changed when they realized the foamy virus isolated initially from a tumor in an African, subsequently was determined to originate in chimpanzees. Now the closest thing to a foamy virus unique to and originating in humans, is HERV-K102, despite it not having sequence homology with primate foamy viruses. On this basis we cannot presently refer to HERV-K102 as being the elusive foamy virus of humans, but instead, for the sake of taxonomy, we can only call it a foamy-like virus or an endogenous retrovirus with the salient features of a foamy retrovirus. HERV-K102 has 19 of 19 tested foamy virus properties, but we do not know yet about the other 4 as they have not yet been tested. In Appendix B we provide more detail on the properties and the references for the findings.

Finally in FIG. 16 we provide a model for how HERV-K102 activation can prevent and/or control the spread of HIV within the host. This model probably applies to all retroviral infections in humans (except those which are foamy retroviruses). Our novel work suggests that vacuolation-associated immature particles induced in cultured CB may contain HERV-K102 pol, may contain DNA genomes, may be infective and might mediate lytic infections. Aside from spumaretroviruses which have vacuolation associated (abundant) immature particles, DNA-containing infectious genomes, and the ability to mediate lytic infections in select fibroblasts (Delelis et al, 2004), these properties are unusual for retroviruses generally, and for HERVs in particular. Since HERV-K protease activity has been reported to diminish HIV infectivity by inappropriately cleaving Gag (Padow et al, 2000), we propose the unusual, foamy-like properties of Type I HERV-K (HML-2) may facilitate its interference with HIV replication. As well, since foamy viruses induce a lytic infection in HIV-1 and HLTV-1 infected cells and lymphocytes (Mikovits et al, 1996) as well as upon select fibroblasts, we propose HERV-K102 pol containing particles may also lytically infect HIV-1 infected cells A model is presented in which the mechanisms by which HERV-K102 may antagonize HIV are shown as: 1) interference with HIV infectivity, 2) vacuolation associated apoptosis of HIV infected cells, and 3) lytic infections of HIV infected cells by HERV-K102 particles. In summary, our work suggests the reactivation of HERV-K102 with HIV infection may represent a novel host defense system against exogenous retroviruses.

Given that HERV-K and/or HERV-K102 is known to be reactivated with certain tumors such as germ cell (Boller et al, 1997, Kleinman et al, 2004), breast cancers (Wang-Johanning et al, 2001, 2003 and others) and in melanomas (Muster et al, 2003), we additionally propose that HERV-K102/HERV-BZU reactivation in the adult may be a novel host protection system against viral and tumor transformation, not previously appreciated or anticipated. Thus, HERV-K102 or HERV-BZU has the unusual and proprietary advantage over other gene therapy vectors, viral or not, that it actually would protect the host from some of the major side effects already known to occur with gene therapy and which until now has prevented its widespread use in the clinic.

In summary, we have not only discovered an infectious HERV, HERV-K102 or K102-like provirus, but have provided evidence this infectious HERV-K102 to which humans appear to be generally tolerant, appears to be functionally similar to primate foamy viruses by the following criteria:
1. Acute vacuolation in susceptible cells in vitro associated with high copy numbers or particles.
2. Probably productive infection in both dividing and non-dividing cells.
3. Budding of infectious particles (immature virions) into endoplasmic reticulum vesicles.
4. Infectious particles (100 nm) of the size and morphology of foamy retroviruses.
5. Highly cytopathic for human fibroblast cells in vitro.
6. Infectious particles are cell associated, liberated by freeze-thawing.
7. Virtually 100% of cells infected (MRC-5 cells) and human diploid fibroblasts are particularly sensitive to FV-induced cytopathic effects.
8. Fairly high titres of replication-competent virus in human hematopoietic cells.
9. Uses a lysine (K) tRNA primer for reverse transcription.

While the preferred embodiments of the invention have been described above, it will be recognized and understood that various modifications may be made therein, and the appended claims are intended to cover all such modifications which may fall within the spirit and scope of the invention.

Methods

Informed consent. The work was performed at the Regional Virus Laboratory within the Research Unit at the Children's Hospital of Eastern Ontario, which is part of the Ottawa Hospital organization. Accordingly, the Ottawa Hospital Research Ethics Board approved the collection of anonymous blood samples with medical histories and included consent to store samples for the research and development of testing methods for new viruses by the Blood Zoonotics Unit. The Ottawa Hospital Research Ethics Board also approved our informed consent for the collection of anonymous cord blood samples from the Ottawa Hospital for use as naïve, recipient blood cells for the study of transmission of bloodborne viruses.

Cord blood (CB) isolation. Under aseptic conditions, cord blood was collected into heparinized tubes and peripheral blood mononuclear cells (PBMC) were prepared as follows: the blood was centrifuged at 2700 rpm for 10 minutes, and the buffy coat placed in 5 mls of media (defined as IMDM plus 0.2% penicillin/gentamycin). The mixture was layered onto Ficoll-Paque (Pharmacia #17-0840-03) in a ratio of 1/3 Ficoll to blood suspension. The tubes were centrifuged 30 minutes at 1600 rpm. The PBMC band at the interface was removed to a sterile 15 ml tube and washed 3 times with media. Cell counts were performed with Eosin Y (1/10 dilution) and the PBMC was suspended at one million cells per ml of media with 10% FCS.

Culture conditions for screening for virus-associated morphological changes. All cultures were incubated at 37° C. in 5% $CO_2$. IMDM media with 0.2% penicillin/gentamycin supplemented with 10% FCS, was used as the basic media. In all cases, cells were re-suspended to $1 \times 10^6$ CB PBMCs per ml of media. Four different culture conditions were employed during the initial screen for morphological changes, and only 2 of 4 culture conditions supported vacuolation and expression of HERV-K102. The media control consisted of $1 \times 10^6$ CB PBMCs per ml in basic media and this supported vacuolation. For the Mixed Lymphocyte Reaction (MLR), PBMCs were isolated from two unrelated CB donors and mixed 1:1 to give $1 \times 10^6$ cells per ml of basic media. This also supported vacuolation and HERV-K102 activation. The third culture condition consisted of basic media supplemented with 1% PHA (or 5 μmg/ml of PHA). After 2 days, the cells were pelleted, the supernatant removed, and the cells re-suspended in basic media supplemented with 20 U/ml ft-2. This culture condition did not support vacuolation. The fourth condition was the addition of PHA at 0.00250 g/ml with 32 U/ml of IL-2, 0.01 mg/ml hydrocortisone and 0.29 mg/ml glutamine at culture initiation. This condition also did not support vacuolation. We found all adult PBMC tested also supported vacuolation when cultured as a single donor or as a MLR in the basic culture media.

Electron Microscopy. Cultures were harvested, washed three times in PBS (no FCS), and then placed in 4% paraformaldehyde fixative, pH 7.4 for 1 to 2 hours to fix. The samples then went to the EM processing laboratory at CHEO.

Cytospins. $1 \times 10^6$ cells were resuspended in 100 ul 5%-PBS and then applied to the cytospin holders. The samples were centrifuged at 600 rpm for 10 minutes. After air drying, the slides were stained with Haematoxylin and Eosin, mounted and viewed.

Haematoxylin and Eosin staining of cytospins. Air dried cytospins were fixed for 10 seconds in absolute ethanol. The slides were then immersed in Harris Haematoxylin for 3 minutes. The slides were washed in water (until it runs clear), and decolorized in 0.5% acid alcohol for 40 seconds. After washing in water for 5 minutes, the slides were stained in 1% Eosin for one minute, washed in cold water for 1 minute, then dehydrated (dipped sequentially in 3 alcohol containers, cleared by dipping the slides in 3 changes of toluene, and mounted.

Immunoprecipitation and western blotting. CB cells cultured for 7 days (Day 7) or not cultured (Day 0) were harvested and $5 \times 10^7$ cells were extracted in 0.5 mls lysis buffer (1% NP40, 100 mM NaCl, 10 mM EDTA in 100 mM TRIS-HCl pH 7.6, for 30 to 60 minutes at room temperature. The lysate is vortexed and centrifuged for 10 minutes at 250×g to remove nuclei. Supernatant is retained. The supernatant is clarified by centrifugation for 30 minutes at 10,000×g (microfuge). The lysates are first pretreated to remove non-specific binding by adding 10 ul of goat anti-rabbit lg agarose (RDI Research, product #941-9136) per 200 ul of lysate. After a one hour incubation at 4° C. with shaking, the tubes are centrifuged briefly at 200×g (5 seconds) in a microfuge, and supernatants harvested. To 200 ul of treated lysates, 800 ul of TBS is added and then purified ML4, ML5 or control rabbit antibody is added (10 ul of 1 mg/ml stock), and is incubated overnight at 4° C. or hour on ice. Then 50 ul of 1 mg/ml solution of agarose conjugated with goat anti-rabbit antibody is added and the tubes mixed with gentle shaking for one hour at 4° C. The agarose is then washed three times with 1 ml Tris-buffered saline (TBS) by pelleting in a microfuge at 200×g for 5 seconds with a final wash in 0.5 M TRIS, pH 6.8. The agarose is again pelleted, all the supernatant carefully removed and discarded, and 50 ul of Sample Buffer is added (25% glycerol, 2% SDS, 0.01% Bromophenol Blue in 62.5 mM TRIS-HCl pH 6.87). The sample are mixed and then heated at 100° C. for 5 minutes. The tubes are microfuged briefly (5 seconds at 200×g) to pellet the agarose, and 1 ul of the supernatant is loaded onto 10-15% SDS-PAGE gradient gels (Amersham BioSciences, pre-cast gels, Cat. #170-0516-01) and the samples run on the Phast-Gel System (Pharmacia) according to manufacturer's instructions. In order to validate proper transfer and to determine the molecular weight of bands revealed in the western blotting step, Coomassie Blue, pre-stained molecular weight standards (Biorad, 7 to 207 kilodaltons, Cat. #161-0318) are also loaded onto the gradient gels after boiling. As soon as the separation is complete, pre-wetted nitrocellulose (Biorad) is placed onto the gels, and the positions of the molecular weight standards are pencilled in. Care is taken to avoid transblotting the stacking gel. The transblot is assembled according to manufacturer's instructions with filter papers pre-wetted with transblot buffer (21.25 g of $Na_2HPO_4$-$7H_2O$ and 5.52 g of $NaH_2PO_4$ was added to 4 litres of $ddH_2O$, pH 7.4), and the transblot console placed onto the separation bed of the Phast-gel system. The transblot is run for 17 minutes. After completion of the transblot, the nitrocellulose is removed, washed in one change of dd $H_2O$, then TBS and then incubated with primary antibody diluted 1/1000 usually overnight at 4° C. with gentle shaking. After washing once in $ddH_2O$, and two changes of TBS, the blot is developed using the Amplified Alkaline Phosphatase Immu-Blot Kit of Biorad (Cat. #170-6412) which can detect up to 10 pg on a blot.

Immunohistology. CB cultured for 7 days (Day 7) or freshly isolated CB cells (Day 0) were washed three times in PBS, pelleted, then fixed in 4% paraformaldehyde pH 7.4 for 1 to 2 hours. The cells were centrifuged, and the fixative replaced with PBS. Standard paraffin embedding for cell block preparation used agar in PBS (0.1M pH 7.4) as a pre-supporting material for the cells. The cells were processed as usual in an automatic tissue processor (ATPtissue Processor from TBS Inc. (Triagle Biomedical Systems Inc.)). Paraffin blocs were cut at 4 microns, deparaffinized, hydrated and stained with the Vectastain ABC Kit Immuno-peroxidase (Rabbit IgG) (Catalog # PK-4001, Vector Laboratories) following manufacturer's instructions.

Collection of plasma, serum and PBMC for the archived sample bank. Upon written informed consent and interview for a short medical history, a serum tube (10 ml red-stoppered vacutainer tubes, BD), and four sodium citrate vacutainer tubes (4.5 ml, BD 369704, siliconized) were collected. Plasma and serum were aliquoted into 4 and 2, sterile cryo tubes respectively, and stored at −80° C. PBMC was isolated from the sodium citrate tubes and frozen down in 10% DMSO with 20% FCS in media at $1 \times 10^7$ cells/ml, and stored at −140° C. in liquid nitrogen.

Tri-Reagent extraction of DNA and mRNA from cells and reverse transcription. Washed PBMC (at least $1 \times 10^7$ total) were lysed in Tri-Reagent and DNA and RNA were prepared according to manufacturer's instructions. Samples for RT-PCR were first DNase digested according to manufacturer's instructions (Promega Technical Bulletin #518) for 30 minutes at 37° C., after which 1 µl of RQ1 DNase stop solution was added to the 10 solution. The tubes were then incubated 65° C. for 10 minutes to inactivate the DNase. Reverse transcription using random hexamers followed manufacturer's instructions (Promega-Reverse Transcription System Technical Bulletin #99.) and was performed with and without MuLV reverse transcriptase. Reverse transcription occurred at 42° C. for 15 minutes, followed by extension at 25° C. for 10 minutes. The products were denatured at 99° C. for 5 minutes then held on ice for the RT-PCR or PCR.

Extraction of presumptive particles from plasma. Plasma samples were thawed, mixed and then 1050 ul were microfuged 10 minutes at 3000 rpm to remove any cellular debris. One ml of plasma was then extracted with the QIAamp UltraSens Virus Method according to manufacturer's instructions (Qiagen). This kit isolates both DNA and RNA virus particles. For analysis of RNA, the DNA was digested (see above) and reverse transcription to generate cDNA by random hexamers was done as above.

β-actin PCR. 50 µl of PCR amplification reaction mix was made by combining 0.2 mM dNTP mixture, 1.5 mM $MgCl_2$, Taq PCR buffer, 0.1 µM β-actin primers (Forward primer=5'-TGA CGG GGT CAC CCA CAC TGT GCC CAT CTA-3' (SEQ ID No. 8) and reverse primer=5'-CTA GM GCA TTT GCG GTG GAC GAT GGA GGG-3' (SEQ ID No. 9)), 5 µl template and nuclease-free water. The reaction mixture was heated to 94° C. for 5 minutes then placed on ice wherein 2.5 µl of a 1/10 dilution of AmpliTaq polymerase were added per tube. The cycling parameters were: 95° C. for 1 minute, 60° C. for 1 minute, and 72° C. for 1 minute, for 35 cycles. Then the tubes were held at 72° C. for 7 minutes and then held indefinitely at 4° C. The PCR product is 661 bp.

HERV-K102 poi PCR. New primers were designed by us, and had the sequences: forward 5'-TGG CAG AGC AGG ATT GTG AA-3' (position 4272 to 4291 in AF164610) (SEQ ID No. 3) and reverse 5'-CAG ATG CTA TTG CCA GTC CA-3' (in reverse orientation, 4565 to 4546 in AF 164610) (SEQ ID No. 4). The PCR product which spans 4272 to 4565 is 294 bp. 100 µl of PCR amplification reaction mix was made by combining 50 µmol of forward and reverse primers, 50 µM-dNTPs, 2.8 U/100 µl total reaction buffer AmpliTaq Gold polymerase, 2 mM $MgCl_2$, PCR buffer II, 5% DMSO, DNA template and nuclease-free water. The AmpliTaq Gold polymerase was activated 12 minutes at 95° C. The cycling parameters were denaturation for 30 seconds at 95° C., annealing for 30 seconds at 50° C., and strand extension for 30 seconds at 72° C., and the number of cycles totalled 35. At the end of the cycling, the tubes were held at 72° C. for 10 minutes and then held indefinitely at 4° C. The band product is 294 by on 1% agarose gels. A 100 by ladder (catalogue # G210)1 from Promega was used to judge molecular weight.

Selection of HERV-K HML-2 Env antigenic peptides, ML4 and ML5, and manufacturing of ML4 and ML5 rabbit antisera. At the time of our investigation, it had already been reported that Type II HERV-K HML-2 was constitutively expressed in human lymphocytes (Armbruester et al, 2002) and thus, unlikely to be relevant to the vacuolation we were observing in vitro. On the other hand, Wang-Johanning et al, 2001, had already shown tumor specific HERV-K102 Env expression in breast cancer. Furthermore they identified HERV-K102 transcripts as existing as a quasi-species (transcripts 97% identifical to HERV-K102) where interestingly, stop codons were absent in most of the transcripts sequenced. Thus, we wanted to develop antisera which could distinguish HERV-K102 Env from other HERV-K Type I HML-2 Env, and not cross-react with HERV-K Type II HML-2 Envs. Through a contract with Washington Biotechnology (Baltimore, Md.), and using their algorithms to predict antigenic peptides, two peptides corresponding to the outer surface unit of HERV-K102 Env were selected. The first one called ML4, corresponds to nt 6473 to 6520 of HERV-K102 and has the amino acid sequence of KRASTEMVTPVTWMDN (SEQ ID No. 5). The first half of this peptide is not found in Type II HERV-K HML-2 sequences. The full sequence is however, identical to K101, K103, K10 and K (II). For HERV-K107, the first M residue is substituted with R, and for HERV-K18 and IDDMK the R is substituted by S. The second peptide called ML5 is specific to HERV-K102, corresponds to nt positions 7229-7279, and has the sequence LETRDCKP-FYTIDLNSS (SEQ ID No. 6). After 4 immunizations, the rabbit antibodies were cross-absorbed, affinity purified and tested by peptide ELISA. These preparations had titres greater than 1/100,000. Washington Biotechnology manufactured both the peptides and the purified antisera.

Peptide ELISAs. One mg of peptide is dissolved in 50 ml of double-distilled, de-ionized water. The peptide is aliquoted to a 96 well plate (at 100 ul/well) and the plate is sealed with film. The plate is either incubated overnight in the refrigerator or for 2 hours at 37° C. Excess peptide is washed off by rinsing 6 times with 350 ul of 0.05% Tween-20/PBS. The plate is blotted to remove excess fluid and then blocked by the addition of 150 ul/well of 1% BSA (BioRad) in PBS. The plate is resealed and incubated for 1 hour at 37° C. or stored for up to one week at 4-8° C. Dilutions of serum at 1/100 made in 1% BSA/PBS are added to plates in duplicate or triplicate (100 ul/well) and incubated overnight in the refrigerator or at 37° C. for 2 hours. Unbound primary antibodies are removed with 6 washes in 0.05% Tween-20/PBS, and excess fluid is blotted off. The secondary antibody, horseradish peroxidase conjugated goat anti-human (heavy and light chain, IgG from BioRad) is diluted 1/2000 in 1% BSA-PBS and 100 ul added per well. This is then incubated for 1.5 to 2 hours at 37° C. Following 6 washes with Tween/PBS, the plates are blotted to remove excess liquid, and 100 ul of OPD substrate is added. For this 1 OPD tablet (4 mg) from Sigma is added to 10 ml of citrate phosphate buffer pH 5.0 plus 4 ul of $H_2O_2$. At 30 minutes the plate is stopped with 50 ul/well 1 N HCl and the absorbance is read at 490 nm.

Infectivity studies of CB lysates onto fibroblasts. All fibroblasts were cultured in flasks in IMDM media with 10% FCS and 0.2% Penicillin/Streptomycin and were seeded at about 0.3 million cells per ml. For the infectivity studies, 2 mls per well of Vero cells were plated at $2.5 \times 10^4$/ml in 12 well plates and incubated at 37° C. in 5% $CO_2$ overnight to let cells adhere. For HFL-1 cells, $3 \times 10^4$ cells per ml were used. For MRC-5 cells, $3 \times 10^4$ cells per ml were added to plates and then incubated for 4 hours to let the cells adhere. All infectivity studies were performed in duplicate and testing of CB lysates was conducted in parallel from single donors or from MLRs which showed no differences. The preparation of the CB lysates was as follows. CB cells freshly prepared (day 0) or cultured for 4 days (day 4) were harvested and adjusted to $1 \times 10^6$/ml in 10% FCS-IMDM media. The cell suspensions were then frozen overnight at −80° C. Then they were thawed at room temperature, and the process repeated twice. After removing the media from the adhered fibroblasts, one ml of the frozen-thawed lysates was added per well, and incubated overnight at 37° C. in 5% $CO_2$. The next morning the lysates were removed and the plates washed an additional 3 times with warmed media. Two mls of warmed media was added to the plates, observed for lack of cytopathic effects, and then incubated for another 6 hours at 37° C. in 5% $CO_2$.

Real Time, Quantitative PCR for HERV-K102 pol. PCR reactions were run on the Applied Biosystems 7500 Real Time PCR system using standarized conditions and buffers for all PCR reactions according to manufacturer's instructions. We commonly employed the one-step master-mix buffers (4309169) and quantitation program (4310299) which also uses the specific primers for reverse transcription. We designed our own primers and probe and had them custom manufactured by Applied Biosystems Inc. The sequence for the forward primer for HERV-K102 pol (4414 to 4441 on AF164610) was 5'-TCT TCA ACC AGT TAG AGA AAA GTT TTC A-3' (SEQ ID No. 13) The reverse primer (4541-4524 on AF164610) was 5'-TGG CM CCT CTG CTT GCA-3' (SEQ ID No. 14). Our TaqMan probe was 6Fam-5'-gca gca cat aaa ata tca tca at-3' (SEQ ID No. 15) which corresponds in the reverse orientation to 4485 to 4463 in AF164610). Thus the sequence being detected was 4414 to 4541 or 128 bps and is a sequence contained within the products amplified with our regular PCR method. We use the 18sRNA as a control for both DNA and RNA (18 S rRNA Hs999 999 01_s1 where the "s1" denotes kits able to prime both DNA and RNA.

All quantitative PCRs used the following program; 9600 emulation mode, absolute quantification, 25 ul volume, with the following thermal profile: Stage 1 48.0° C. for 30 minutes (the reverse transcription step with and without added reverse transcriptase), Stage 2 95° C. for 10 minutes (to activate the Taq) and then 40 cycles of 95° C. for 15 seconds (denature) and 60° C. for one minute (annealing and elongation combined). Under these conditions the PCR product must be short, optimally about 125 bp. Longer PCR products if amplified will appear as drift on the Ct scans. If the primers span on either side of introns, most likely only mRNA but not DNA will be amplified.

For our studies reported here, standard curves using 4 different concentrations (2500, 250, 25 and 2.5 pg per reaction mixture) using standard (male) DNA (TaqMan Control Genomic DNA (Human), product #4312660, 10 ng/µl, Applied Biosystems Inc. product) are assayed in parallel with the 18 S rRNA kit and the custom HERV-K102 pol kit on a single plate. For each side of the 96 well plate, a "reference standard", consisting of 250 pg per reaction mixture is assayed. This allows the software to calculate a test value depending on what each standard is assigned and allows direct comparison of HERV-K102 "genomic equivalents" when compared to 18 s rRNA "genomic equivalents". We assign values which allows us to directly enumerate "genomic equivalents per ml of starting material" depending on the dilution factors, and how much template is used. All testing is performed in triplicate and one can expect coefficients of variation to be under 5%. On average we obtain around 1.91%.

REFERENCES

1. Bieda K et al, J General Virology 82: 591-596, 2001.
2. Patience C et al, J Virology 70: 2654-2657, 1996.
3. Mayer J, Dev Biol (Basel) 106: 439-441, 2001.
4. Turner G et al, Curr Biol 11: 1531-1535, 2001.
5. Ono M et al, J Virology 60: 589-598, 1986.
6. Zsiros J et al, J General Virology 79: 61-70, 1998.
7. Medstrand P & Blomberg J, J Virology 73: 2463-2466, 1993.
8. Tonjes R R et al, J Virology 73: 9187-9195, 1999.
9. Costas J. J Mol Evol 53: 237-243, 2001.
10. Lower R et al, PNAS 90: 4480-4484, 1993.
11. Barbulescu M et al, Curr Biol 9: 861-868, 1999.
12. Armbruester V et al, Clinical Cancer Research 8: 1800-1807, 2002.
13. Megstrand P et al, J Gen Virology 73: 2463-2466, 1992.
14. Brodsky I et al, Blood 81: 2369-2374, 1993.
15. Wang-Johanning F et al, Clinical Cancer Research 7: 1553-1560, 2001.
16. Johnston J B et al, Ann Neurol 50: 434-442, 2001.
17. Herve C A et al, Clin Exp Immunol 128: 75-82, 2002.
18. Hishikawa T et al, Viral Immunology 10: 137-147, 1997.
19. Boller K et al, J Virology 71: 4581-4588, 1997.
20. Yu S F et al, J Virology 73: 1565-1572, 1999.
21. Hur K et al, Mech Ageing Dev 123: 1637-1647, 2002.
22. Lynch W P & Sharpe A H, J Virology 74: 1558-1565, 2000.
23. Zeine R et al, J Neurosci Res 64: 380-391, 2001.
24. Rakowicz-Szulczynska E M et al, Clin Diagn Lab Immunol 6: 115-126, 1999.
25. Hirschl S & Muster T. GenBank entry AY186778 "MERV polymerase", 2002.

26. Tschopp R R, Brandner S, Maino S, et al. Virology 1996; 216: 338-346.
27. Bieniasz P D, Weiss R A,& McClure M O. J Virol 1995; 69: 7295-7299.
28. Mikovits J A, Hoffman P M, Rethwilm A & Ruscetti F W. J Virol 1996; 70: 2774-2780.
29. Armbruester V, Sauter M, Krautkraemer E et al, *Clinical Can Res* 2002; 8:1800-1807.
30. Bannert N, Kurth R. PNAS 2004; 101 Suppl. 2: 14572-14579.
31. Barbulescu M, Turner G, Seaman M I et al. Current Biology 1999; 9:861-868.
32. Belshaw R, Pereira V, Katzourakis A et al. PNAS 2004; 101: 4894-4899.
33. Belshaw R, Dawson A L A, Woolven-Allen J et al. J Virol 2005; 79: 12507-12514.
34. Benit L, Dessen P, Heidmann T. J Virol 2001; 75: 11709-11719.
35. Bieda K, Hoffmann A, Boller K. J Gen Virol 2001; 82: 591-596.
36. Boller K, Janssen O, Schuldes H et al. J Virol 1997; 71: 4581-4588.
37. Cannon P M & Anderson W F. Retroviral vectors for gene therapy, in: Cell and Gene Therapy, eds. N. Smyth Templeton & M Dekker. 2004: 1-16.
38. Christensen T. Rev Med Virol 2005; 15: 179-211.
39. Cordonnier A, Casella J-F, Heidmann T. J Virol 1995; 69: 5890-5897.
40. Delelis O, Lehmann-Che J and Saib A. Current Opinion in Microbiology 2004; 7: 400-406.
41. Etkind P R, Lumb K, Du J & Racevskis J. *Virology* 1997; 234: 304-308.
42. Everts B & van der Poel H G. Cancer Gene Therapy 2005; 12:141-161.
43. Goedert J J, Sauter M E, Jacobson L P et al. Cancer Epi, Biomarkers & Prevention 1999; 8: 293-296.
44. Heinkelein M, Hoffmann U, Lucke M et al. Cancer Gene Thera 2005; 12: 947-953.
45. Hill C L, Bieniasz P D & McClure M O. J Gen Virol 1999; 80: 2003-2009.
46. Juretzek T, Holm T, Gartner K et al, J Virol 2004; 78: 2472-2477.
47. Kleiman A, Senyuta N, Tryakin A et al. *Int J Cancer* 2004; 110:459-461.
48. Kuhelj R, Rizzo C J, Chang C-H et al. J Biol. Chem. 2001; 276:16674-16682.
49. Lecellier C-H & Voinnet O. Immunological Reviews 2004; 198: 285-303.
50. Lecellier C-H, Dunoyer P, Arar K et al. *Science* 2005; 308: 557-560.
51. Linial M L and Eastman S W. Current Topics in Microbiology and Immunology 2003; 277: 89-110.
52. Linial M L. Foamy virus replication: implications for interaction with other retroviruses and host sequences. In Evolving Scientific and Regulatory Perspectives on Cell Substrates for Vaccine Development. (ed) Brown F, Lewis A M, Peden K, Krause P. Dev Biol 2001 volume 106: pp 231-236. Basel Karger.
53. Linial M L. J Virol 1999; 73: 1747-1755.
54. Lower R. *Trends in Microbiology* 1999; 7: 350-356.
55. Lower R, Boller K, Hasenmaier B et al. *Proc Natl Acad Sci, USA* 1993; 90: 4480-4484.
56. Meiering C D & Linial M. Clin Micro Rev 2001; 14: 165-176.
57. Meiering C B, Comstock K E, Linial M L. 2000; 74: 1718-1726.
58. Mergia A & Heinkelein M. *Current Topics in Microbiology and Immunology* 2003; 277: 131-159.
59. Mikovits J A, Hoffman P M, Rethwilm A & Ruscetti F W. J Virol 1996; 70: 2774-2780.
60. Muster T, Waltenberger A, Grassauer A et al. Cancer Res 2003; 63: 8735-8741.
61. Nakamura A, Okazaki Y, Sugimoto J et al. *J Hum Genet* 2003; 48: 575-581.
62. Ono M. J Virol 1986; 58: 937-944.
63. Park J, Nadeau P, Zucali J R et al. Virology 2005; (in press)
64. Patience C, Takeuchi Y, Cosset F-L and Weiss R A. J Virol 1998; 72: 2671-2676.
65. Patience C, Simpson G R, Colletta A A et al, J Virol 1996; 70: 2654-2657.
66. Priet S, Gros N, Navarro J-M et al. Molec Cell 2005; 17: 479-490.
67. Priet S, Sire J & Querat G. Curr HIV Res 2006; 4: 31-42.
68. Rethwilm A. Current Topics in Microbiology and Immunology 2003; 277: 1-26.
69. Seifarth W, Frank O, Zeilfelder U et al. *J Virol* 2005; 79:341-352.
70. Simpson G R, Patience C, Lower R et al. Virology 1996; 222: 451-456.
71. Solly S K, Trajcevski S, Frisen C et al. Cancer Gene Ther 2003; 10: 30-39.
72. Stauffer Y, Theiler G, Sperisen P et al. Cancer Immunity 2004; 4: (18 pages long).
73. Sutkowski N, Chen G, Calderon G, Huber B T. J Virol 2004; 78: 7852-7860.
74. Tai C H, Logg C R, Park J M et al, Human Gene Therapy 2003; 14: 789-802.
75. Tonjes R R, Czauderna F & Kurth R. J Virol 1999; 73: 9187-9195.
76. Tristem M. J Virol 2000; 74: 3715-3730.
77. Trobridge G, Vassilopoulos G, Josephson N & Russell D W. Methods Enzymol 2002; 346: 628-648.
78. Tschopp R R, Brandner S, Maino S, et al. Virology 1996; 216: 338-346.
79. Villesen P, Aagaard L, Wiuf C, Pedersen F S. *Retrovirology* 2004; 1: 32-44.
80. Vogetseder W, Dumtahrt A, Mayersbach P et al. AIDS Res Hum Retroviruses 1993; 9: 687-694.
81. Wang-Johanning F, Frost A R, Jian B et al. Oncogene 2003; 22:1528-1535.
82. Wang-Johanning F, Frost A R, Johanning G L et al. Clin Cancer Res 2001; 7: 1553-1560.
83. Wolkowicz R & Nolan G P. Gene Therapy 2005; 12: 467-476.
84. Yu S F, Sullivan M D & Linial M L. J Virol 1999; 73: 1565-1572.
85. Zawada M, Liwen I, Pernak M et al. *Polish J of Pharmacology* 2003; 55: 869-875.

TABLE 1

HERV-K102 cDNA in Cultured Lymphocytes is INDUCED upon Culture but Requires Monocytes for Initiation

| | HERV-K102 ddCt Ratio | ddCt ratio in presence of UNG | Relative Inhibiton by UNG |
|---|---|---|---|
| CB Day 0 | 0.74 | | |
| CB Day 4 | 3.68 | 1.78 | 52% |
| CB Day 7 * | 2.87 | 2.45 | 15% |
| PBMC # Day 0 | 0.64 | | |
| PBMC # Day 5 | 0.78 | | |
| PBMC # Day 7 | 0.85 | | |

* About 1/3 of the cells apoptose on day 7.
Monocytes were depleted from PBMC prior to cell culture.

TABLE 2

HERV-K102 (DNA) Relative Levels are increased in MS patient's PBMC and increases when cultured in vitro by Real Time (Quantitative) PCR

| Sample PBMC | 18sRNA Ref/HERV-K102 Ref | HERV-K102/18 s RNA (genome equivalents per ml) | Ratio (Proxy gene copy #) | Co-efficient of Variation (%) |
|---|---|---|---|---|
| Healthy Control | 186,957/ 186,441 | 944,889/ 1,330,000 | 0.71 | 1.98% |
| MS Day 0 | 94,225/ 107,264 | 21,300,000/ 8,420,000 | 2.53 | 1.91% |
| MS Day 4 | 94,225/ 107,264 | 25,800,000/ 6,820,000 | 3.78 | 1.91% |
| MS Day 7 | 94,225/ 107,264 | 5,970,000/ 3,580,000 | 1.67* | 1.91% |

*Note about 33% of the cells apoptose on day 7 and these are the cells which are highly vacuolated.

TABLE 3

Summary of HERV-K102 ddCt Ratios in Plasma

| Samples | HERV-K102 ddCt Ratios | % Positive | Range |
|---|---|---|---|
| Normals (24/24) | 0.88 +/- 0.39 | 0% | 0.41-1.42 |
| Cord Blood (2/4) | 2.22 | 50% | 2.04, 2.39 |
| HIV Viremia (26/32) | 14.88 +/- 32.27 | 81% | 1.45-152.2 |
| MS (8/11) | 3.19 +/- 1.71 | 73% | 1.69-6.50 |

TABLE 4

Study of 22 HIV Viremic Samples for HERV-K102 pol ddCt

| BZU ID | UNG digested Ratio | HERV-K102 ddCt Ratio | HIV VL | Samples Taken January 2006 | CD4 (2005) | |
|---|---|---|---|---|---|---|
| 16 | 1.04 | 152.22 | 24,843 | NONE | 32319 | 613 |
| 12 | 0.6 | 77.71 | >500,000 | Not Stated | 32231 | ns |
| 22 | 0.18 | 31.78 | 17,613 | NONE | 32349 | ns |
| 13 | 1.27 | 28.44 | 22,142 | NONE | 32316 | 474 |
| 11 | 0.36 | 15.78 | 30,898 | Combivir, ritonavir, atazanavir | 32345 | 210 |
| 2 | 0.47 | 12.82 | 14,211 | NONE | 32202 | 341 |
| 15 | 0.89 | 11.63 | >500,000 | Abacavir, atazanavir, lamivudine | 32300 | 180 |
| 7 | 1.51 | 7.62 | 332,420 | none | 32328 | 13 |
| 20 | 1.11 | 4.59 | 2,512 | Not stated | 32364 | ns |
| 8 | 2.36 | 4.26 | 37,118 | none | 32295 | ns |
| 21 | 1 | 2.85 | 343,843 | none | 32336 | 610 |
| 4 | 1.92 | 2.77 | 385,195 | none | 32307 | 423 |
| 5 | 0.69 | 2.5 | 38,171 | none | 32212 | 476 |
| 1 | 1.3 | 2.48 | >500,000 | none | 32337 | 7 |
| 10 | 0.84 | 2.08 | 304,581 | Ritonavir, combivir, atazanavir | 32273 | 34 |
| 3 | 1.53 | 1.96 | 1,020 | Not stated | 32179 | ns |
| 14 | 0.96 | 1.47 | 1,240 | Abacavir, efavirenz, combivir | 32335 | 455 |
| 18 | 0.55 | 1.45 | 217,125 | Abacavir, lamivudine, kaletra | 32366 | 120 |
| 9 | NA | 0.83 | 1,410 | Combivir, atazanavir | 32332 | 221 |
| 6 | NA | 0.81 | 2,664 | Tenofovir, ritonavir, trepanovir | 32326 | 52 |
| 19 | 0.33 | 0.67 | 27,717 | None | 32331 | 1010 |
| 17 | 0.29 | 0.49 | 919 | Combivir, kaletra | 32348 | 378 |

TABLE 5

Excess HERV-K102 DNA Templates are Also Detected in Plasma Samples from Patients with Other Bloodborne Viruses

| Bloodborne Pathogen | HERV-K102 ddCT Ratio in PLASMA |
|---|---|
| EBV | 4.56 |
| HHV-7 | 4.00 |
|  | 4.32 |
|  | 1.17 |
|  | 5.78 |
| CMV | $5.79 \times 10^6$ |
|  | Undetected |
|  | 1.80 |
|  | $1.368 \times 10^9$ |
|  | 2.0 |
|  | 0.73 |
|  | 2.01 |
| HCV | Undetected |
|  | $2.7 \times 10^8$ |

TABLE 6

Serology for HERV-K1O2 Envelope Reactivity by ELISA with Synthetic Peptides

| Serum Sample | ML4 Peptide (% positive) | ML5 Peptide (% positive) |
|---|---|---|
| Normal Controls | 1/51 (2%) | 1/51 (2%) |
| MS | 15/24 (62.5%) | 4/24 (17%) |
| HIV Viremia | 8/10 (80%) | 7/10 (70%) |
| Herpes Viremia | 3/17 (17.6%) | 3/17 (17.6%) |

Boller et al (1997) reported 3.9% of normals (Gag and Env tested) but only 2.8% of HIV patients had antibodies. However, for the latter the samples may have been predominately non-viremic patients on anti-viral therapy.

TABLE 7

Screening for Agents able to Modulate HERV-K102 Replication (cDNA Production) in Cultured Cord Blood Cells

| Cord Blood day of Harvest | Condition | HERV-K102 ddCt Ratio | Level of Control Activity (%) | ddCt performed with UNG |
|---|---|---|---|---|
| Day 5 | control | 2.19 | — | |
| Day 5 | St. John's Wort | 1.57 | 71.7% | |
| Day 5 | Tuftsin 1/5000 | 4.14 | 189% | 2.10 (100%) |
| Day 5 | E2 | 2.91 | 133% | |
| Day 5 | Oncolyn | 1.22 | 55.7% | |
| Day 5 | Tuftsin 1/500 | 1.44 | 65.7% | |
| Day 5 | DHEA | 2.60 | 119% | |
| Day 5 | EM652 | 3.07 | 140% | 2.06 (100%) |
| Day 5 | Tamoxifen | 3.43 | 157% | 2.64 (63%) |
| Day 0 | Control | 0.77 | N/A | |

TABLE 8

Increase in HERV-K102 cDNA Induced in Cultured Cord Blood (CB) But not in PBMC Depleted of Monocytes

|  | HERV-K102 ddCt Ratio | ddCt ratio in presence of UNG | Relative Inhibiton by UNG |
|---|---|---|---|
| CB Day 0 | 0.74 | | |
| CB Day 4 | 3.68 | 1.78 | 52% |
| CB Day 7 * | 2.87 | 2.45 | 15% |
| PBMC # Day 0 | 0.64 | | |
| PBMC # Day 5 | 0.78 | | |
| PBMC # Day 7 | 0.85 | | |

* About ⅓ of the cells apoptose on day 7.
Monocytes were depleted from PBMC prior to cell culture.

These results show the CB cultures start out with normal genomic levels of HERV-K102 (normal is 0.88+/−0.39, n=24). Then HERV-K102 is expressed and reverse transcribed inside particles. Thus, there is now an excess of HERV-K102 DNA detected by the ddct method. On day 7 when about ⅓ of the cells apoptose (those with the most amount of vacuolation and particles) the relative ratio drops indicating cells have released their particles and these are washed away when the cells are harvested for DNA extraction. Note that the remaining cells making cDNA have incorporated less UTP suggesting they are not monocytes.

Note when monocytes are completely removed from PBMCs, HERV-K102 cDNA is not detected suggesting the initiating cell may be monocytes which liberate particles which then infect T cells, or monocytes are necessary for HERV-K102 induction and particle formation.

TABLE 9

Summary of Similarities of HERV-K102 with PFV*

| | PFV | HERV-K102 | Comments |
|---|---|---|---|
| Hallmarks of FV | 11 | 9 (did not directly test if infectious genomes are DNA, or if capable of intracellular retrotransposition) | Includes: vacuolation association, particles do not bud from cell surface, immature particles, abundant intracellular particles, can cause lytic infections in some fibroblasts, particles contain DNA and/or RNA genomes, lacks the CXXC motif in the surface unit of Env, non-pathogenic, provirus genome begins with TGTG (asymmetric integration) |
| Distinguishing features from other retroviruses or HERVs | 12 | 10 (did not test directly if HERV-K102 is oncolytic and have not tested in vivo infectivity) | Sequence clusters away from most retroviruses or HERVs, lacks the REV/REX domain in env, lacks the CKS17 immunosuppressive domain in the TM of Env, nuclear staining of Gag, lacks the MHR in the capsid (Gag), no cleavage of Gag into nc and capsid, naturally oncolytic, infects many cell types in vivo, etc. |
| Overall summary of PFV attributes | 23 | 19 (not all properties have been assessed for HERV-K102) | Only 1 other attribute of PFV not found in HERV-K102 (PFV lacks the Cys-His Box in the nucleocapsid of Gag, but is present in both Type I and Type II HERV-K HML-2 members) |

*PFV = Prototypic Foamy Virus = SFV cpz (hu)

The invention claimed is:

1. A method of detecting human endogenous retrovirus (HERV) K102 activation in a human comprising:
   providing a sample from the human suspected of containing activated HERV K102;
   adding a peptide consisting of the amino acid sequence as set forth in SEQ ID NO:5 or SEQ ID NO:6 to the sample;
   incubating the sample and the peptide under conditions promoting interaction between the peptide and the antibodies to HERV K102 Env if present;
   detecting an interaction between the peptide and the antibodies, wherein a positive signal indicates that the antibodies are present in the sample and a negative signal indicates that the antibodies are not present in the sample, wherein the presence of the antibodies indicates HERV K102 activation.

2. The method according to claim 1 wherein the peptide is a peptide consisting of the amino acid sequence as set forth in SEQ ID No. 5.

3. The method according to claim 1 wherein the peptide is a peptide consisting of the amino acid sequence as set forth in SEQ ID No. 6.

* * * * *